United States Patent
Nguyen et al.

(10) Patent No.: US 9,127,017 B2
(45) Date of Patent: Sep. 8, 2015

(54) COMPOUNDS WITH OXIME ESTER AND/OR ACYL GROUPS

(75) Inventors: My T. Nguyen, Ho Chi Minh (VN); Jean-Philippe Tremblay-Morin, Vaudreuil-Dorion (CA); Philippe Gaudreault, Brossard (CA)

(73) Assignee: American Dye Source, Inc., Quebec (CA)

( * ) Notice: Subject to any disclaimer, the term of this patent is extended or adjusted under 35 U.S.C. 154(b) by 0 days.

(21) Appl. No.: 14/122,126

(22) PCT Filed: May 24, 2012

(86) PCT No.: PCT/CA2012/050340
§ 371 (c)(1),
(2), (4) Date: Mar. 24, 2014

(87) PCT Pub. No.: WO2012/159213
PCT Pub. Date: Nov. 29, 2012

(65) Prior Publication Data
US 2014/0200350 A1    Jul. 17, 2014

Related U.S. Application Data

(60) Provisional application No. 61/489,892, filed on May 25, 2011, provisional application No. 61/489,910, filed on May 25, 2011.

(51) Int. Cl.
| | | |
|---|---|---|
| *C07D 487/12* | (2006.01) | |
| *C07D 209/82* | (2006.01) | |
| *C07C 69/00* | (2006.01) | |
| *C07D 495/04* | (2006.01) | |
| *C08F 2/50* | (2006.01) | |
| *C08F 4/00* | (2006.01) | |
| *C07D 487/14* | (2006.01) | |
| *C07D 221/18* | (2006.01) | |
| *C07D 333/78* | (2006.01) | |
| *C07D 409/10* | (2006.01) | |
| *C07C 323/47* | (2006.01) | |
| *C07C 251/66* | (2006.01) | |
| *C07D 209/86* | (2006.01) | |
| *C07C 13/62* | (2006.01) | |
| *C07D 307/92* | (2006.01) | |
| *C07C 49/665* | (2006.01) | |
| *C07C 49/792* | (2006.01) | |
| *C07C 251/48* | (2006.01) | |
| *C07C 251/64* | (2006.01) | |

(Continued)

(52) U.S. Cl.
CPC .............. *C07D 495/04* (2013.01); *C07C 13/62* (2013.01); *C07C 49/665* (2013.01); *C07C 49/792* (2013.01); *C07C 251/48* (2013.01); *C07C 251/64* (2013.01); *C07C 251/66* (2013.01); *C07C 323/47* (2013.01); *C07D 209/56* (2013.01); *C07D 209/86* (2013.01); *C07D 221/18* (2013.01); *C07D 307/91* (2013.01); *C07D 307/92* (2013.01); *C07D 333/78* (2013.01); *C07D 409/10* (2013.01); *C07D 487/14* (2013.01); *C08F 2/50* (2013.01); *C08F 4/00* (2013.01); *C07C 2103/54* (2013.01)

(58) Field of Classification Search
USPC .................... 548/416, 418, 441; 549/41, 456; 560/129
See application file for complete search history.

(56) References Cited

U.S. PATENT DOCUMENTS

| | | |
|---|---|---|
| 3,558,309 A | 1/1971 | Laridon et al. |
| 4,255,513 A | 3/1981 | Laridon et al. |
| 4,575,330 A | 3/1986 | Hull |

(Continued)

FOREIGN PATENT DOCUMENTS

| | | |
|---|---|---|
| CN | 1934114 A | 3/2007 |
| CN | 101341172 A | 1/2009 |

(Continued)

OTHER PUBLICATIONS

Drager, et al., "New Potential DNA Intercalators of the Carbazole Series from Indole-2,3-quinodimethanes: Synthesis, Crystal Structure, and Molecular Modeling with a Watson-Crick Mini-Helix," Monatshefte fur Chemie, vol. 24, 1993 (pp. 559-576).

(Continued)

*Primary Examiner* — Charanjit Aulakh
(74) *Attorney, Agent, or Firm* — Wilmer Cutler Pickering Hale and Dorr LLP

(57) ABSTRACT

There are provided compounds comprising optionally substituted (FORMULA I) fused with one or two optionally substituted (FORMULA II), wherein A and E each independently represent —CH$_2$—, —NH—, —O—, —S—, or —C(=O)— and B represents a bond, —CH$_2$—, —NH—, —O—, —S—, or —C(=O)—, said compound having directly or indirectly attached thereto at least one acyl and/or oxime ester group. Such compounds are useful inter alias as photoinitiators.

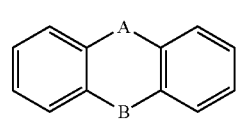

(FORMULA I)

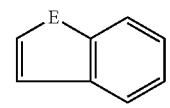

(FORMULA II)

16 Claims, 9 Drawing Sheets

(51) Int. Cl.
*C07D 209/56* (2006.01)
*C07D 307/91* (2006.01)

(56) References Cited

U.S. PATENT DOCUMENTS

| | | | |
|---|---|---|---|
| 4,766,152 | A | 8/1988 | Karrer |
| 5,840,465 | A | 11/1998 | Kakinuma et al. |
| 5,853,446 | A | 12/1998 | Carre et al. |
| 6,051,367 | A | 4/2000 | Kunita et al. |
| 6,949,678 | B2 | 9/2005 | Kunimoto et al. |
| 7,449,574 | B2 | 11/2008 | Kim et al. |
| 7,556,910 | B2 | 7/2009 | Kim et al. |
| 7,632,954 | B2 | 12/2009 | Hiyoshi et al. |
| 8,524,425 | B2 | 9/2013 | Matsumoto et al. |
| 8,846,277 | B2 | 9/2014 | Makino et al. |
| 8,911,921 | B2 | 12/2014 | Matsumoto et al. |
| 2009/0023085 | A1 | 1/2009 | Tsuchimura |
| 2009/0122234 | A1 | 5/2009 | Ito |
| 2010/0136467 | A1 | 6/2010 | Matsumoto et al. |
| 2010/0136491 | A1 | 6/2010 | Matsumoto et al. |
| 2010/0188765 | A1 | 7/2010 | Matsumoto et al. |
| 2010/0210749 | A1 | 8/2010 | Taguchi |
| 2011/0037027 | A1 | 2/2011 | Stoessel et al. |

FOREIGN PATENT DOCUMENTS

| | | |
|---|---|---|
| CN | 101679394 A | 3/2010 |
| CN | 101687794 A | 3/2010 |
| CN | 102250115 A | 11/2011 |
| DE | 19700064 A1 | 7/1997 |
| EP | 320264 A2 | 6/1989 |
| EP | 678534 A1 | 10/1995 |
| EP | 855731 A1 | 7/1998 |
| EP | 863534 A2 | 9/1998 |
| EP | 1717239 A1 | 11/2006 |
| EP | 2141206 A1 | 1/2010 |
| JP | 2005271576 A | 10/2005 |
| JP | 2006251337 A | 9/2006 |
| JP | 2008-171863 A | 7/2008 |
| JP | 2009-079150 A | 4/2009 |
| JP | 2009244230 A | 10/2009 |
| JP | 2010-032985 A | 2/2010 |
| JP | 2010-062980 A | 3/2010 |
| JP | 2010-185072 A | 8/2010 |
| JP | 2010-526846 A | 8/2010 |
| JP | 2010-527338 A | 8/2010 |
| JP | 2011244230 A | 12/2011 |
| TW | 200906821 A | 2/2009 |
| TW | 201004904 A | 2/2010 |
| WO | WO-9705141 A1 | 2/1997 |
| WO | WO-02100903 A1 | 12/2002 |
| WO | WO-2006018405 A1 | 2/2006 |
| WO | WO-2006108497 A1 | 10/2006 |
| WO | WO-2006122630 A1 | 11/2006 |
| WO | WO-2008138724 A1 | 11/2008 |
| WO | WO-2008138732 A1 | 11/2008 |
| WO | WO-2009019173 A1 | 2/2009 |
| WO | WO-2009-041253 A1 | 4/2009 |
| WO | WO-2010083872 A2 | 7/2010 |
| WO | WO-2010136109 A1 | 12/2010 |
| WO | WO-2011016648 A1 | 2/2011 |

OTHER PUBLICATIONS

Haber, et al., "N-Benzoylindole-2, 3-Quinodimethane: Diels-Alder Reactivity and Synthetic Applications for [b]Annellated Indoles," Tetrahedron, vol. 47, 1990 (pp. 1925-1936).

International Search Report and Written Opinion issued by the Canadian Intellectual Property Office as International Searching Authority for International Application No. PCT/CA2012/050340 mailed Aug. 13, 2012 (15 pgs.).

Kura, et al., "New Oxime Ester Photoinitiators for Color Filter Resists," RadTech Report, May/Jun. 2004 (pp. 30-35).

Levesque, et al., "Synthesis and Thermoelectric Properties of Polycarbazole, Polyindolocarbazole, and Polydiindolocarbazole Derivative," Chem Mater, vol. 19, 2007 (pp. 2128-2138).

Minabe, et al., "Syntheses and Some Properties of 9, 2',:7', 9"-, 9,2':9',9"-, and 9,4':9',9"-Terfluorene," Bulletin of the Chemical Society of Japan, vol. 51, No. 11, 1978 (pp. 3373-3376).

Odian, G., "Principles of Polymerization, Fourth Edition," Table of Contents, Wiley Interscience, A John Wiley & Sons, Inc., Publication, 2004 (20 pgs.).

Robinson, B., "The Fischer Indolisation of Cyclohexane-1, 4-dione Bis-phenylhydrazone," Department of Chemistry, The University of Nottingham, 1962 (3 pgs.).

Hiyoshi, et al., "Donor-Π-acceptor type Symmetry Cyclic Triindoles: Synthesis and Properties," Heterccycles, vol. 72, p. 231-238, Abstract for Database Reaxys, Elseview Information Systems GmbH, Database Accession No. 11216248 (XRN) (1 pg. total) (2007).

Supplementary European Search Report issued by the European Patent Office for European Patent Application No. 12789315.4 dated Oct. 9, 2014 (9 pgs.).

Yilmaz, G. et al., "Thioxanthone-Carbazole as a Visible Light Photoinitiator for Free Radical Polymerization," Journal of Polymer Science: Part A: Polymer Chemistry, vol. 48, pp. 5120-5125 (2010).

COMPOUNDS WITH OXIME ESTER AND/OR ACYL GROUPS

CROSS REFERENCE TO RELATED APPLICATIONS

This application claims benefit, under 35 U.S.C. §119(e), of U.S. provisional application Ser. No. 61/489,910 and 61/489,892, both filed on May 25, 2011.

FIELD OF THE INVENTION

The present invention is concerned with compounds comprising at least one oxime ester and/or acyl group. More specifically, present invention is concerned with compounds based on indene fused with fluorene or 9,10-dihydroanthracene and derivatives thereof.

BACKGROUND OF THE INVENTION

Photosensitive or photopolymerizable compositions typically include, for example, an ethylenic unsaturated bond-containing polymerizable compound and a photopolymerization initiator. Such photosensitive or photopolymerizable compositions polymerize and cure when irradiated with light, and are therefore used, for example, in photosetting or photocuring inks, photosensitive printing plates, color filter resists, black matrix resins, and a variety of photoresists, including dry film resists.

In recent years, demand has arisen for photosensitive or photopolymerizable compositions sensitive to shorter wavelength (365 nm or 405 nm) light sources, and consequently the demand for photopolymerization initiators sensitive to such light sources has also increased.

Photopolymerization initiators are also called free radical photoinitiators. Upon exposure to light of a wavelength to which they are sensitive, they generate free radicals and thus initiate free radical polymerization of surrounding polymerizable compounds.

It is typically desired that such photoinitiators exhibit good sensitivity to light, especially in the UV region of the spectrum, low discoloration upon use, and good thermal stability (for storage and processing).

Some organic compounds comprising acyl and/or oxime ester groups are known as free radical photoinitiators. They have found use in color filter resists due to their absorption in the ultra-violet radiation region (between 300 and 450 nm). Irgacure OXE-01™ and OXE-02™ (available from BASF, Germany) are known photoinitiators for some applications, including color filter resists. Some triazine-based compounds are also known as useful photoinitiators.

The present description refers to a number of documents, the content of which is herein incorporated by reference in their entirety.

SUMMARY OF THE INVENTION

In accordance with the present invention, there is provided:
1. A compound comprising optionally substituted

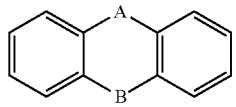

(FORMULA I) fused with one or two optionally substituted

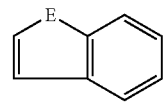

(FORMULA II), wherein A and E each independently represent —$CH_2$—, —NH—, —O—, —S—, or —C(=O)— and B represents a bond, —$CH_2$—, —NH—, —O—, —S—, or —C(=O)—, said compound having directly or indirectly attached thereto at least one oxime ester and/or acyl group.

2. The compound of item 1, wherein the oxime ester group is —$CR_6$=N—O—(C=O)—$R_7$ or =N—O—(C=O)—$R_7$, wherein $R_6$ and $R_7$ are the same or different substituents.

3. The compound of item 2, wherein $R_6$ represents:
   hydrogen;
   $C_1$-$C_{12}$ alkyl optionally substituted with one or more:
      phenyl,
      halogen,
      —$NR_9R_{10}$,
      —O-L, and/or
      —S-L;
   $C_4$-$C_{10}$ cycloalkyl, $C_2$-$C_{12}$ alkenyl, $C_4$-$C_{10}$ cycloalkenyl, $C_2$-$C_{12}$ alkynyl, or $C_4$-$C_{10}$ cycloalkenyl, each of which being optionally substituted by alkyl and/or —O-L; or
   phenyl optionally substituted with one or more:
      $C_1$-$C_6$ alkyl,
      halogen,
      nitrile,
      alkyloxy,
      —$COOR_{10}$, and/or
      $C_2$-$C_{12}$ alkylcarboxyl,
   wherein L is hydrogen or $C_1$-$C_6$ alkyl and wherein each of $R_5$, $R_9$ and $R_{10}$ is independently hydrogen, $C_1$-$C_{12}$ alkyl; $C_4$-$C_{10}$ cycloalkyl; $C_1$-$C_{12}$ alkenyl; $C_4$-$C_{10}$ cycloalkenyl; $C_2$-$C_{12}$ alkynyl; $C_4$-$C_{10}$ cycloalkynyl; $C_1$-$C_{12}$ haloalkyl; or optionally substituted aryl.

4. The compound of item 3, wherein $R_6$ is alkyl optionally substituted with —O—$C_1$-6 alkyl.

5. The compound of item 4, wherein $R_6$ is methyl or butyl.

6. The compound of item 5, wherein $R_6$ is methyl.

7. The compound of any one of items 2 to 6, wherein $R_7$ represents alkyl, cycloalkyl, alkenyl, or cycloalkenyl, each of which being optionally substituted with aryl or halogen, or $R_7$ is aryl optionally substituted with alkyl or halogen.

8. The compound of item 7, wherein $R_7$ represents $C_1$-$C_{12}$ alkyl optionally substituted with phenyl; $C_4$-$C_{10}$ cycloalkyl; or phenyl optionally substituted with $C_1$-$C_6$ alkyl.

9. The compound of item 8, wherein $R_7$ is $C_1$-$C_{12}$ alkyl; $C_4$-$C_{10}$ cycloalkyl; or phenyl.

10. The compound of item 9, wherein $R_7$ is methyl.

11. The compound of any one of items 1 to 10, wherein the acyl group is —C(=O)—$R_{30}$, wherein $R_{30}$ is optionally substituted alkyl, cycloalkyl, alkenyl, cycloalkenyl, alkynyl, cycloalkynyl, or aryl, each of which optionally comprising one or more oxygen atom, sulfur atom, nitrogen atom, carbonyl group, carbamate group, carbamide group, and/or ester group.

12. The compound of item 11, wherein said alkyl, cycloalkyl, alkenyl, cycloalkenyl, alkynyl, cycloalkynyl, and aryl in $R_{30}$ is substituted with one or more polyethylene glycol chain, $C_1$-$C_{12}$ alkyl optionally substituted with one or more:
—$NR_8R_9$,
—O-L,
—S-L, and/or
phenyl optionally substituted with one or more: $C_1$-$C_6$ alkyl, halogen, nitrile, alkyloxy, $COOR_{10}$, and/or $C_2$-$C_{12}$ alkylcarboxyl;
$C_4$-$C_{10}$ cycloalkyl, $C_2$-$C_{12}$ alkenyl, $C_4$-$C_{10}$ cycloalkenyl, $C_2$-$C_{12}$ alkynyl, $C_4$-$C_{10}$ cycloalkynyl, each of which being optionally substituted by alkyl and/or —O-L, and/or
aryl, such as phenyl, thiophenyl, biphenyl and naphthyl, each of which being optionally substituted with one or more:
$C_1$-$C_6$ alkyl,
halogen,
nitrile,
alkyloxy,
—$COOR_{10}$, and/or
$C_2$-$C_{12}$ alkylcarboxyl.
wherein L, $R_5$, $R_5$ and $R_{10}$ are as defined in item 3.

13. The compound of item 12, wherein $R_{30}$ is linear alkyl, phenyl or thiophenyl, all of which being optionally substituted with a linear alkyl or with —O-L.

14. The compound of item 13, wherein $R_{30}$ is methyl, 2-methylphenyl, phenyl, thiophenyl, or 4-methoxyphenyl.

15. The compound of any one of items 1 to 14, wherein at least one of the oxime ester group and/or acyl groups is attached to the compound through a linker -LK-.

16. The compound of item 15, wherein -LK- is optionally substituted alkylene, cycloalkylene, alkenylene, cycloalkenylene, alkynylene, cycloalkynylene, arylene, —S-arylene, —NH-arylene, or —N(aryl)-arylene, each of which optionally comprising one or more oxygen atom, sulfur atom, nitrogen atom, carbonyl group, carbamate group, carbamide group, and/or ester group.

17. The compound of item 16, wherein the alkylene, cycloalkylene, alkenylene, cycloalkenylene, alkynylene, cycloalkynylene, arylene, —S-arylene, —NH-arylene, and —N(aryl)-arylene are substituted with one or more:
polyethylene glycol chain,
$C_1$-$C_{12}$ alkyl optionally substituted with one or more:
—$NR_8R_9$,
—O-L,
—S-L, and/or
phenyl optionally substituted with one or more: $C_1$-$C_6$ alkyl, halogen, nitrile, alkyloxy, $COOR_{10}$, and/or $C_2$-$C_{12}$ alkylcarboxyl;
$C_4$-$C_{10}$ cycloalkyl, $C_2$-$C_{12}$ alkenyl, $C_4$-$C_{10}$ cycloalkenyl, $C_2$-$C_{12}$ alkynyl, $C_4$-$C_{10}$ cycloalkynyl, each of which being optionally substituted by alkyl and/or —O-L, and/or
aryl, such as phenyl, biphenyl and naphthyl, or aryloyl, such as benzoyl, each of which being optionally substituted with one or more:
$C_1$-$C_6$ alkyl,
halogen,
nitrile,
alkyloxy,
—$COOR_{10}$, and/or
$C_2$-$C_{12}$ alkylcarboxyl.
wherein L, $R_5$, $R_5$ and $R_{10}$ are as defined in item 3.

18. The compound of any one of items 1 to 17, wherein FORMULA I and/or either or both FORMULA II are independently substituted by one or more of the following substituents:
$C_1$-$C_{12}$ alkyl, $C_1$-$C_{12}$ alkyloxy, $C_4$-$C_{10}$ cycloalkyl, $C_1$-$C_{12}$ alkenyl, $C_4$-$C_{10}$ cycloalkenyl, cycloalkenyl, $C_2$-$C_{12}$ alkynyl, and/or $C_4$-$C_{10}$ cycloalkynyl, each of which being optionally substituted with one or more:
$NR_8R_9$,
—O-L,
—S-L, and/or
phenyl optionally substituted with one or more $C_1$-$C_6$ alkyl, halogen atom, nitrile, alkyloxy, $COOR_{10}$, and/or $C_2$-$C_{12}$ alkylcarboxyl; and/or
phenyl, biphenyl and/or naphthyl, each of which being optionally substituted with one or more:
$C_1$-$C_6$ alkyl,
halogen atom,
nitrile,
alkyloxy,
—$COOR_{10}$, and/or
$C_2$-$C_{12}$ alkylcarboxyl,
wherein L, $R_8$, $R_9$ and $R_{10}$ are as defined in item 3.

19. The compound of any one of items 1 to 18 comprising one optionally substituted FORMULA II.

20. The compound of item 19 comprising optionally substituted

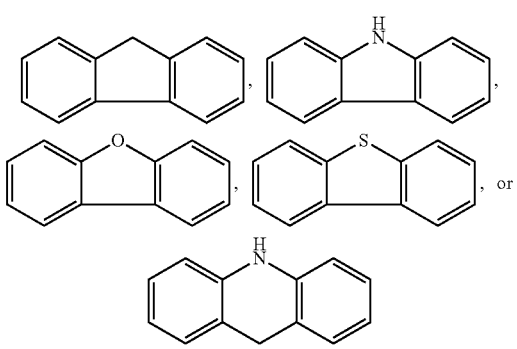

fused with optionally substituted

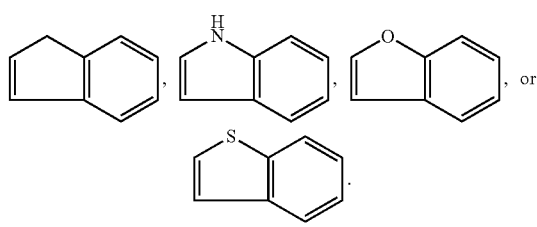

21. The compound of item 20 comprising optionally substituted

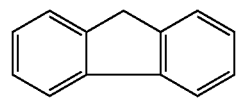 [SMILES: c1ccc2c(c1)Cc1ccccc1-2]

fused with optionally substituted

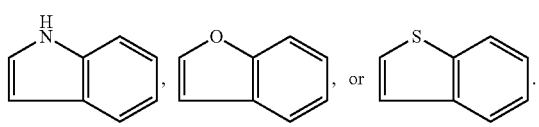

22. The compound of item 20 comprising optionally substituted

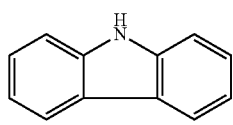

fused with optionally substituted

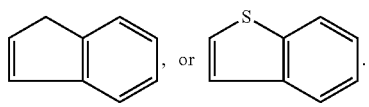

23. The compound of item 20 comprising optionally substituted

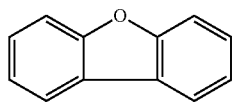

fused with optionally substituted

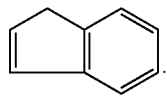

24. The compound of item 20 comprising optionally substituted

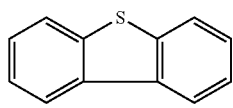 [SMILES: c1ccc2c(c1)sc1ccccc12]

fused with optionally substituted

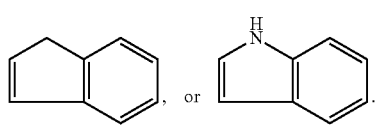 [SMILES: C1=Cc2ccccc2C1 ; c1ccc2[nH]ccc2c1]

25. The compound of item 20 comprising optionally substituted

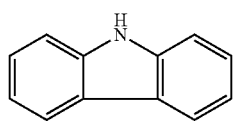 [SMILES: c1ccc2c(c1)[nH]c1ccccc12]

fused with optionally substituted

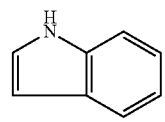

26. The compound of any one of items 1 to 18 comprising two optionally substituted FORMULA II.

27. The compound of item 26 comprising optionally substituted

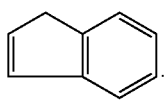

fused with optionally substituted

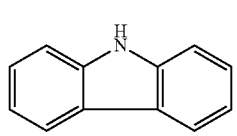

and with optionally substituted

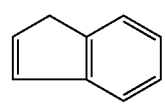

28. The compound of item 26 comprising optionally substituted

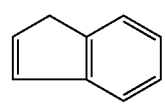

fused with optionally substituted

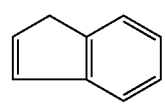

and with optionally substituted

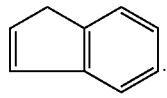

29. The compound of any one of items 1 to 18 being:

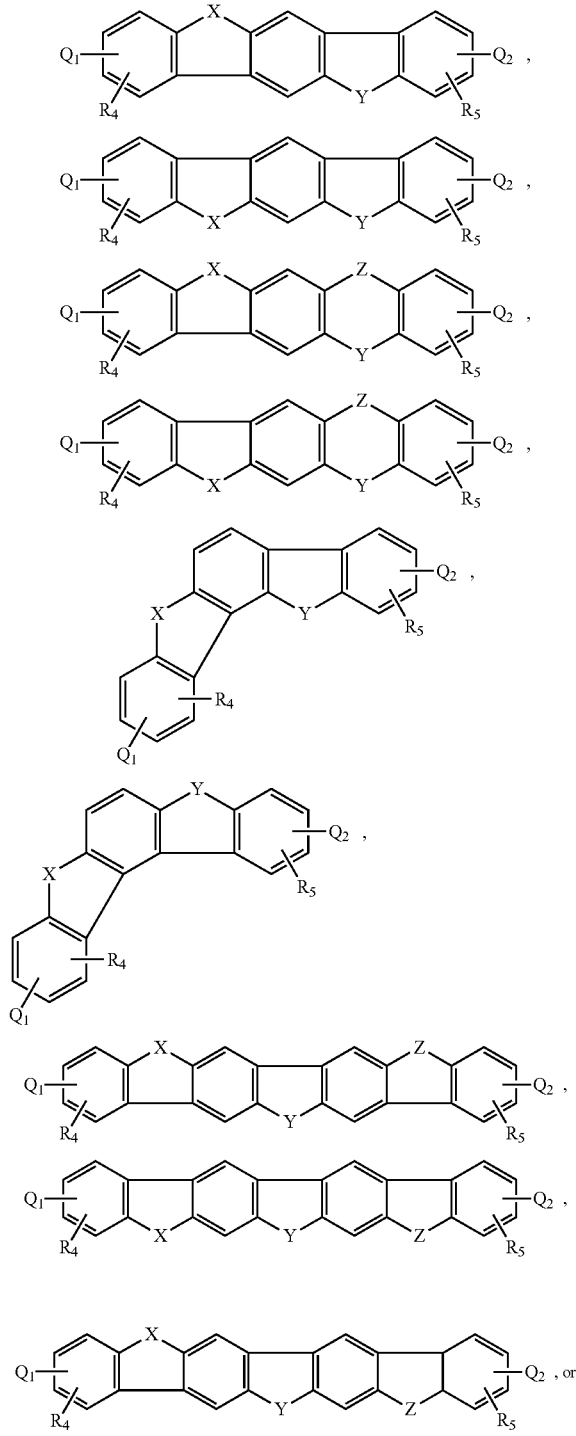

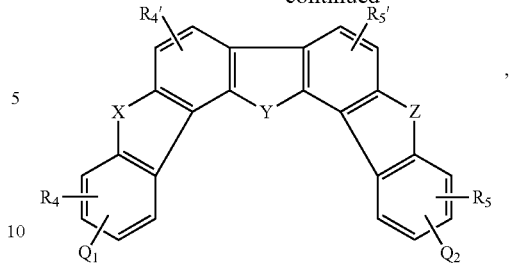

wherein:
R$_4$, R$_5$, R$_4$' and R$_5$' are optional and independently represent, in the case of R$_4$ and R$_5$, one to four and, in the case of R$_4$' and R$_5$', one or two:
  C$_1$-C$_{12}$ alkyl or alkyloxy, said alkyl and alkyloxy being optionally substituted with one or more:
    —NR$_8$R$_9$,
    —O-L or —S-L, and/or
    phenyl optionally substituted with one or more:
      C$_1$-C$_6$ alkyl, halogen atom, nitrile, alkyloxy, —COOR$_{10}$, and/or C$_2$ to C$_{12}$ alkylcarboxyl;
  C$_4$-C$_{10}$ cycloalkyl, C$_2$-C$_{12}$ alkenyl, C$_4$-C$_{10}$ cycloalkenyl, C$_2$-C$_{12}$ alkynyl, C$_4$-C$_{10}$ cycloalkynyl, each of which being optionally substituted by alkyl and/or —O-L, and/or
  phenyl, biphenyl and naphthyl, each of which being optionally substituted with one or more:
    C$_1$-C$_6$ alkyl,
    halogen,
    nitrile,
    alkyloxy,
    —COOR$_{10}$, and/or
    C$_2$-C$_{12}$ alkylcarboxyl,
Q$_1$ and Q$_2$ are optional and independently represent one to four acyl groups and/or oxime ester groups of formula

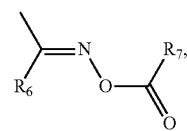

each of X, Y and Z independently represent

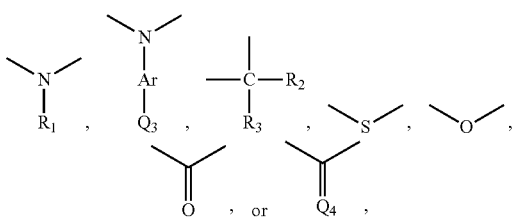

wherein:
R$_1$, R$_2$, and R$_3$ each independently represent:
  a hydrogen atom;
  C$_1$-C$_{12}$ alkyl optionally substituted with one or more:
    —NR$_8$R$_9$,
    —O-L,
    —S-L, and/or phenyl optionally substituted with one or more $C_1$-$C_6$ alkyl, halogen, nitrile, alkyloxy, —$COOR_{10}$, and/or $C_2$-$C_{12}$ alkylcarboxyl;

$C_4$-$C_{10}$ cycloalkyl, $C_2$-$C_{12}$ alkenyl, $C_4$-$C_{10}$ cycloalkenyl, $C_2$-$C_{12}$ alkynyl, $C_4$-$C_{10}$ cycloalkynyl, each of which being optionally substituted by alkyl and/or —O-L, and/or phenyl, biphenyl or naphthyl, each of which being optionally substituted with one or more:
$C_1$-$C_6$ alkyl,
halogen,
nitrile,
alkyloxy,
—$COOR_{10}$, and/or
$C_2$-$C_{12}$ alkylcarboxyl, $Q_3$ represents a hydrogen atom, an acyl group, or an oxime ester group of formula:

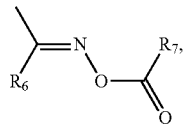

$Q_4$ represents an oxime ester of formula:

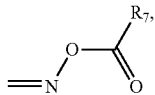

and

Ar is a linker -LK- as defined in any one of items 15 to 17, wherein L, $R_5$, $R_5$ and $R_{10}$ are as defined in item 3, and wherein $R_6$ and $R_7$ are as defined in any one of items 2 to 10.

30. The compound of item 29 being:

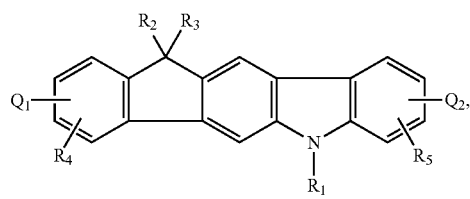

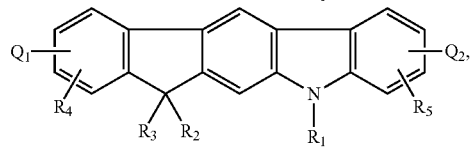

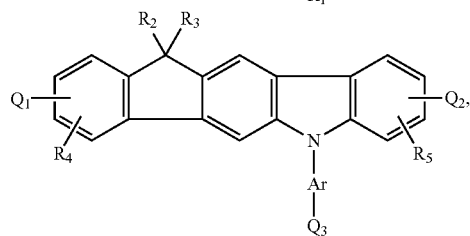

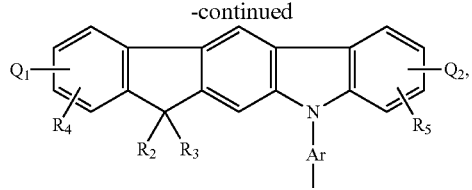

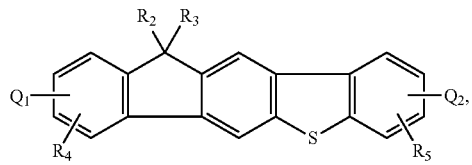

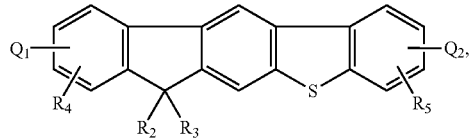

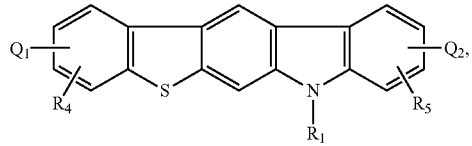

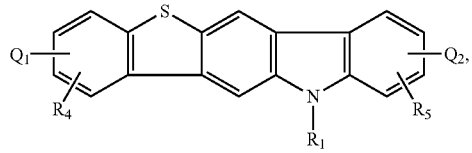

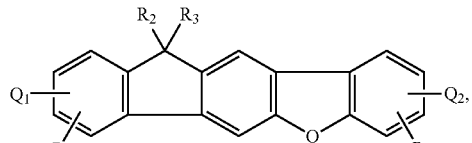

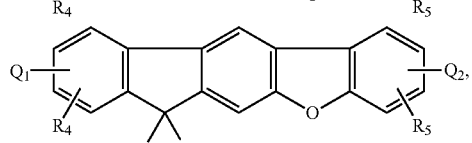

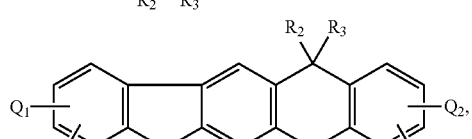

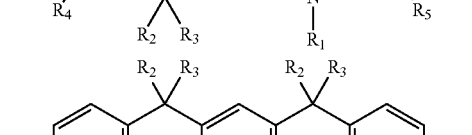

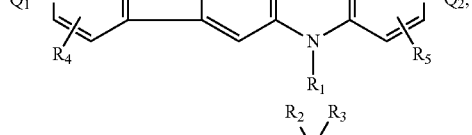

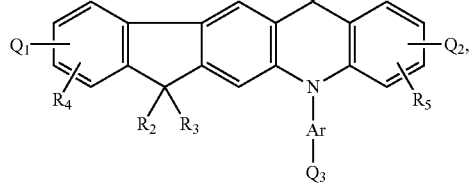

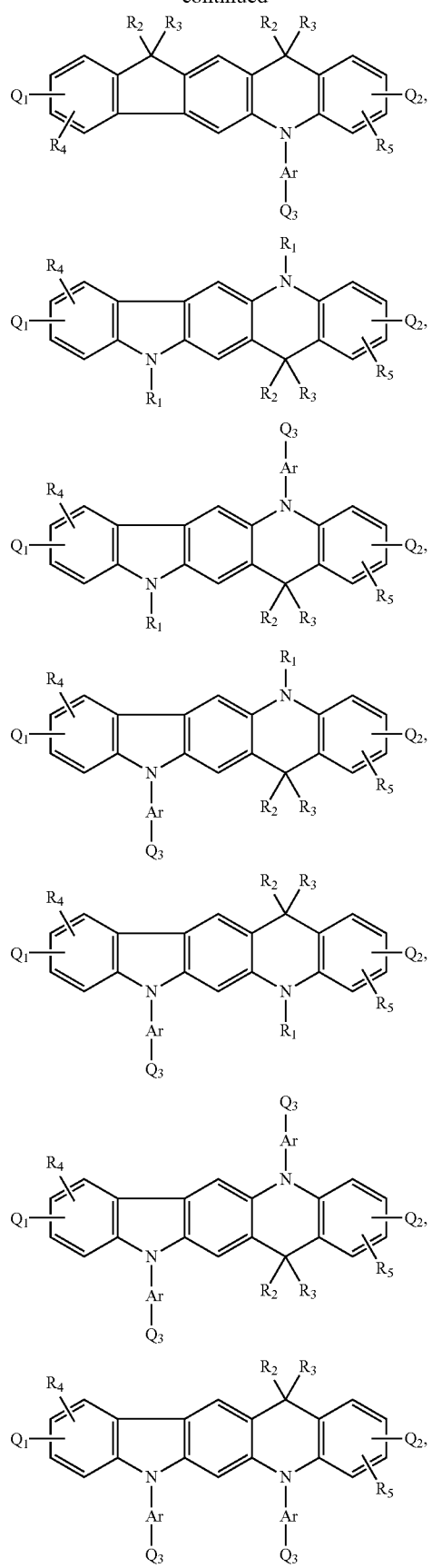
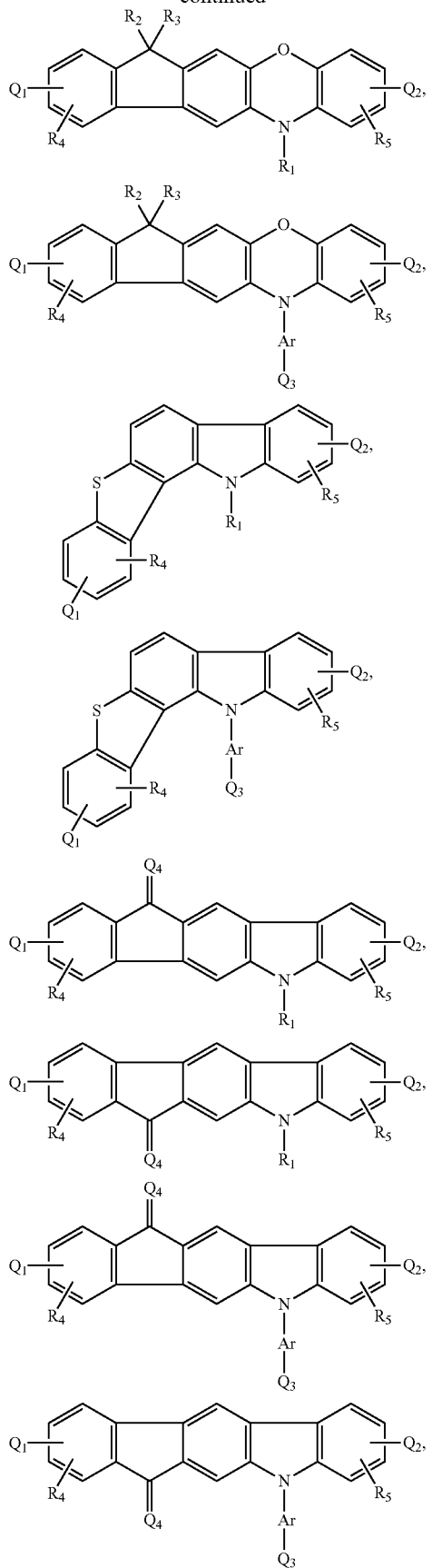

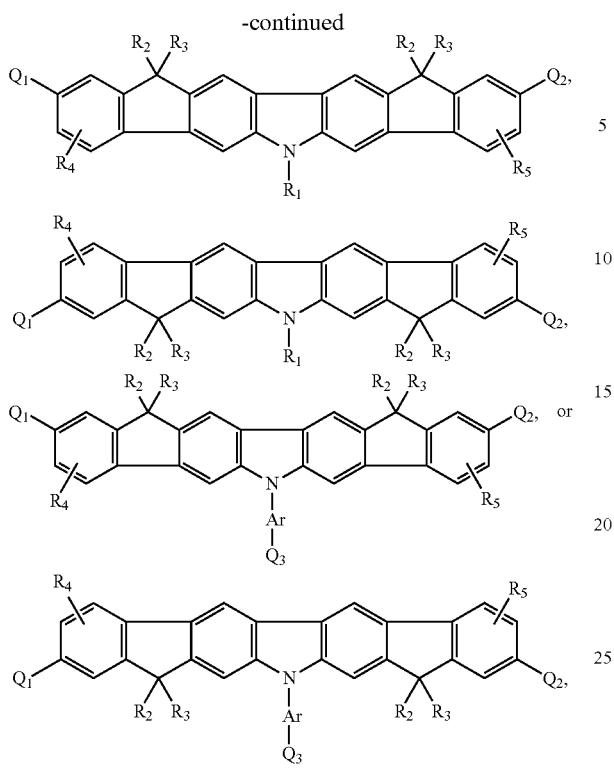

wherein $Q_1$, $Q_2$, $Q_3$, $Q_4$, $R_1$, $R_2$, $R_3$, $R_4$, $R_5$, and Ar are as defined in item 29.

31. The compound of item 29 or 30, wherein —Ar— is optionally substituted arylene, said arylene optionally comprising one or more oxygen atom, sulfur atom, nitrogen atom, carbonyl group, carbamate group, carbamide group, and/or ester group.

32. The compound of item 31, wherein the substituents of the arylene are one or more:
  $C_1$-$C_{12}$ alkyl optionally substituted with one or more:
    —$NR_8R_9$,
    —O-L,
    —S-L,
    phenyl optionally substituted with one or more: $C_1$-$C_6$ alkyl, halogen, nitrile, alkyloxy, $COOR_{10}$, and/or $C_2$-$C_{12}$ alkylcarboxyl;
  $C_4$-$C_{10}$ cycloalkyl, $C_2$-$C_{12}$ alkenyl, $C_4$-$C_{10}$ cycloalkenyl, $C_2$-$C_{12}$ alkynyl, $C_4$-$C_{10}$ cycloalkynyl, each of which being optionally substituted by alkyl and/or —O-L, and/or
  phenyl, biphenyl and naphthyl, each of which being optionally substituted with one or more:
    $C_1$-$C_6$ alkyl,
    halogen,
    nitrile,
    alkyloxy,
    —$COOR_{10}$, and/or
    $C_2$-$C_{12}$ alkylcarboxyl.
  wherein L, $R_8$, $R_9$ and $R_{10}$ are as defined in item 3.

33. The compound of any one of items 29 to 32, wherein each —Ar-$Q_3$ independently represents

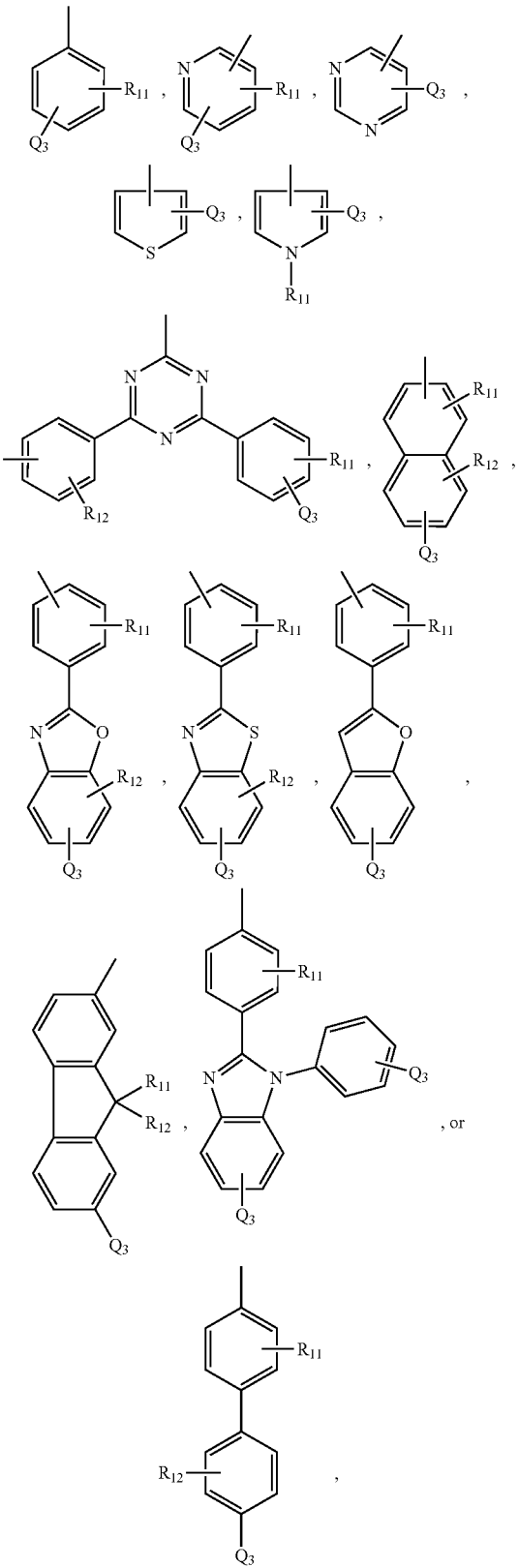

wherein $R_{11}$ and $R_{12}$ are optional and independently represent one or more:
- $C_1$-$C_{12}$ alkyl optionally substituted with one or more:
  - $-NR_8R_9$,
  - $-O-L$,
  - $-S-L$, and/or
  - phenyl optionally substituted with one or more: $C_1$-$C_6$ alkyl, halogen, nitrile, alkyloxy, $COOR_{10}$, and/or $C_2$-$C_{12}$ alkylcarboxyl;
- $C_4$-$C_{10}$ cycloalkyl, $C_2$-$C_{12}$ alkenyl, $C_4$-$C_{10}$ cycloalkenyl, $C_2$-$C_{12}$ alkynyl, and/or $C_4$-$C_{10}$ cycloalkynyl, each of which being optionally substituted by alkyl and/or $-O-L$; and/or
- phenyl, biphenyl and naphthyl, each of which being optionally substituted with one or more:
  - $C_1$-$C_6$ alkyl,
  - halogen,
  - nitrile,
  - alkyloxy,
  - $-COOR_{10}$, and/or
  - $C_2$-$C_{12}$ alkylcarboxyl.

wherein L, $R_5$, $R_9$ and $R_{10}$ are as defined in item 3.

34. The compound of any one of items 29 to 33 being:

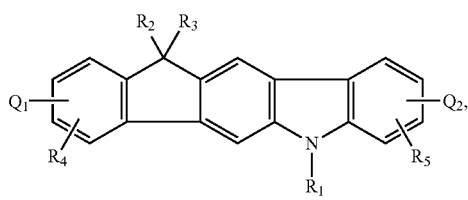

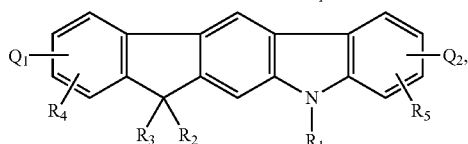

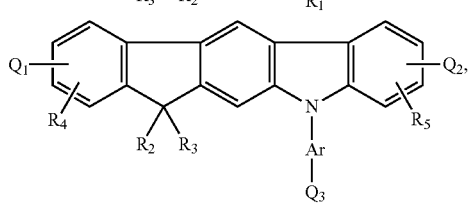

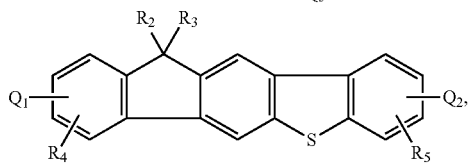

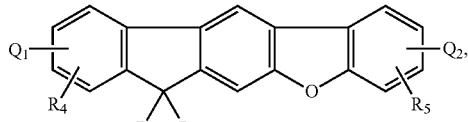

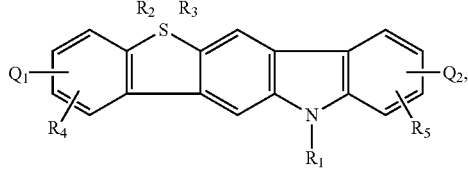

-continued

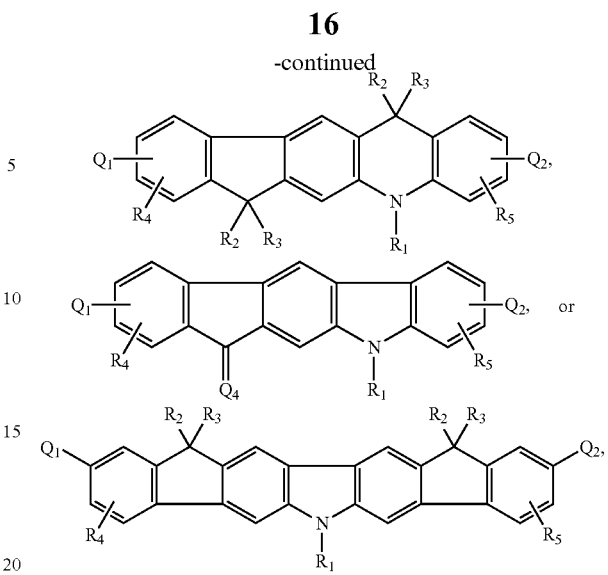

wherein:
- $R_4$ and $R_5$ are optional and independently represent one $C_1$-$C_{12}$ alkyl or $C_1$-$C_{12}$ alkyloxy,
- $Q_1$ and $Q_2$ are optional and independently represent one oxime ester group of formula

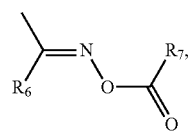

- $R_1$, $R_2$, and $R_3$ each independently represent a hydrogen atom or $C_1$-$C_{12}$ alkyl,
- $Q_3$ represents a hydrogen atom or an oxime ester group of formula:

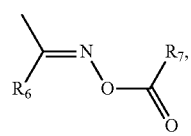

- $Q_4$ represents an oxime ester of formula:

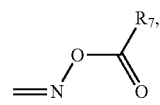

- Ar represents

and
- $R_6$ and $R_7$ independently represents alkyl.

35. The compound of item 34 being:
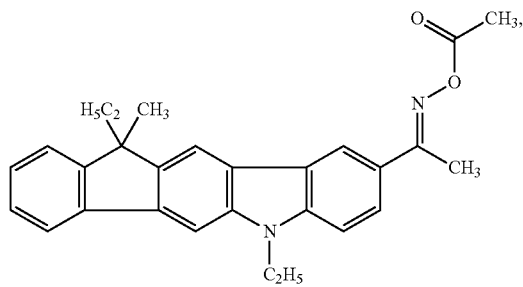
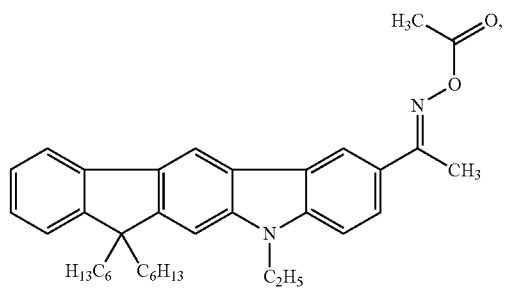
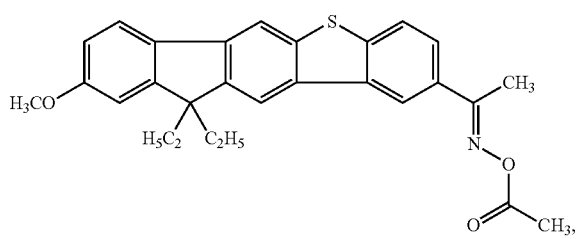
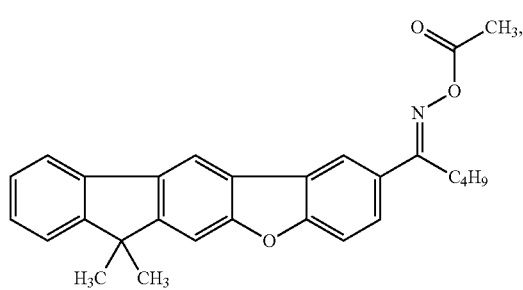
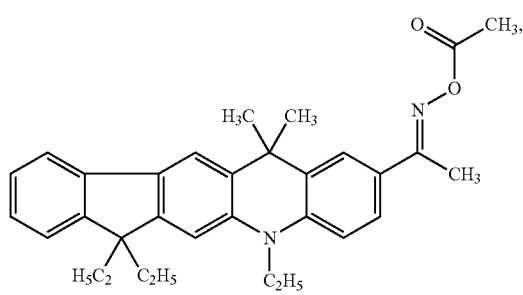
-continued
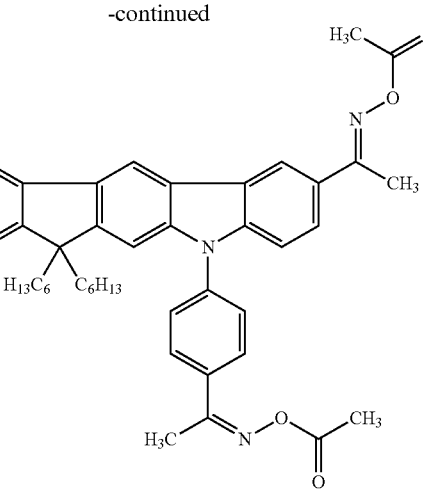
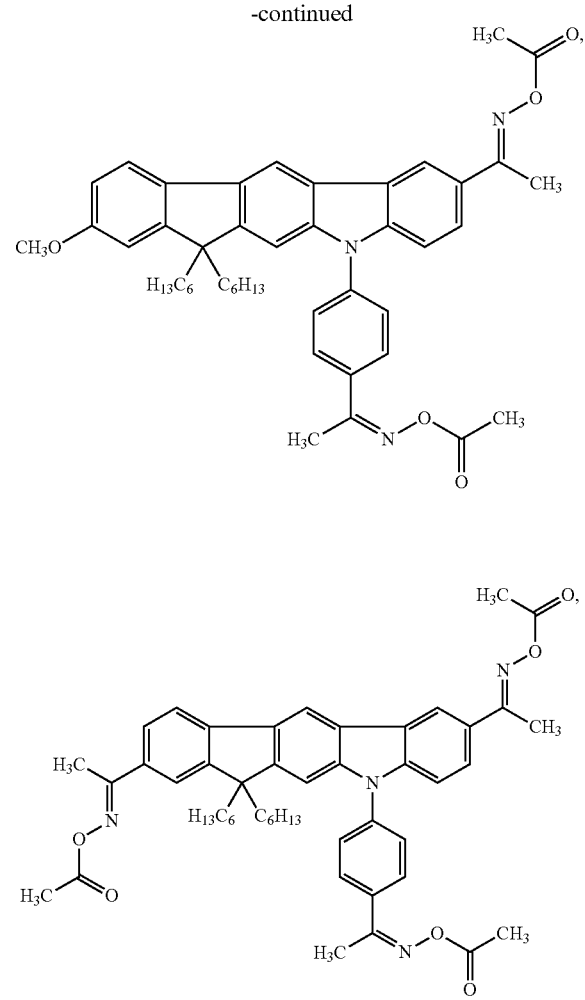
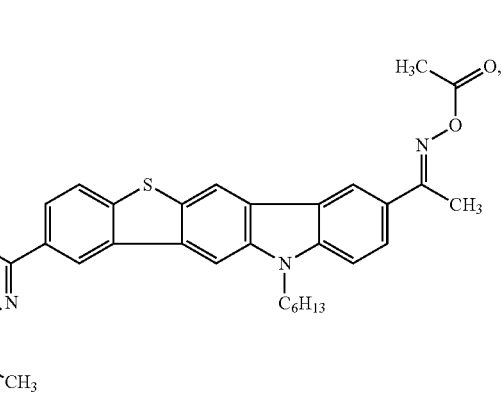
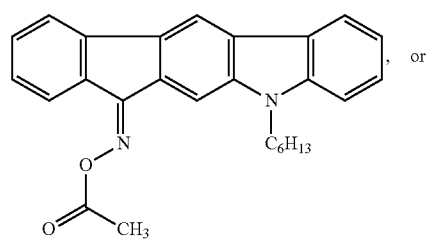

-continued

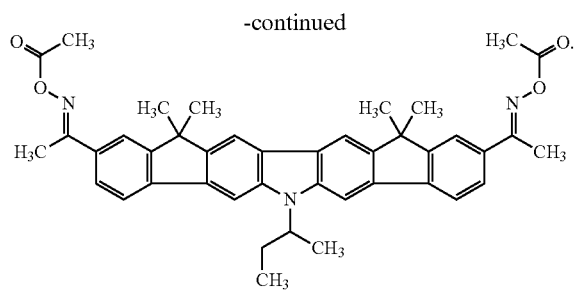

36. The compound item 26, being truxene, truxenone, triazatruxene or a derivative thereof, said truxene, truxenone, triazatruxene or derivative thereof having attached thereto, directly or indirectly, at least one acyl and/or oxime ester group.

37. The compound of item 36 being:

truxene:

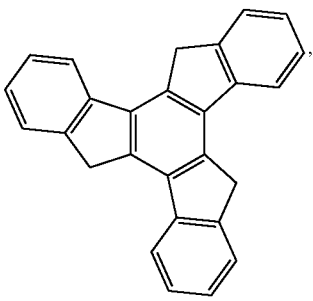

truxenone:

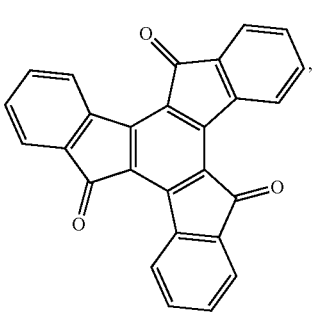

triazatruxene:

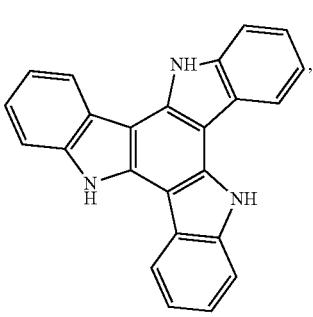

or a derivative thereof,
the truxene, truxenone, triazatruxene, or derivative thereof having attached thereto at least one of $-E_1$, $-LK-E_1$, $-LK-(E_1)_2$ or $=E_2$,
$-E_1$ representing an acyl group of formula $—C(=O)—R_{30}$ or an oxime ester group of formula $—CR_6=N—O—(C=O)—R_7$, and $=E_2$ representing an oxime ester group of formula $=N—O—(C=O)—R_7$, wherein LK is as defined in any one of items 15 to 17, $R_6$ and $R_7$ are as defined in any one of items 2 to 10 and $R_{30}$ is as defined in any one of items 11 to 14.

38. The compound of items 36 or 37 being of formula:

Formula 1

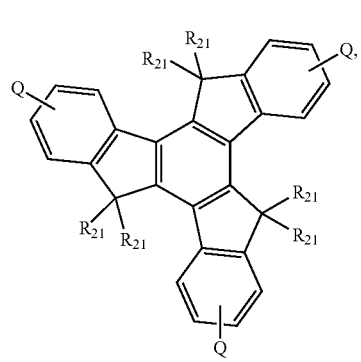

Formula 2

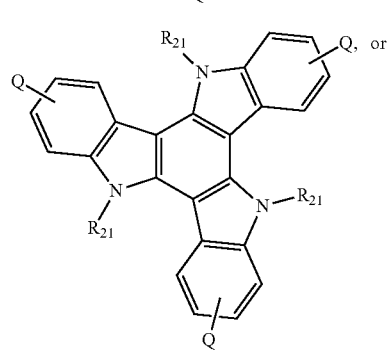

Formula 3

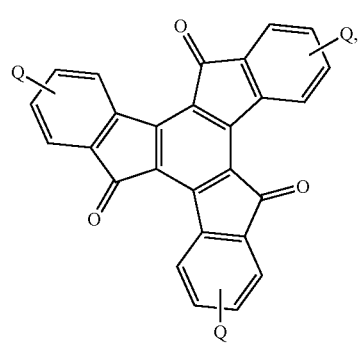

wherein:
each Q independently represents 1 to 4:
  hydrogen;
  $-E_1$;
  $-LK-E_1$;
  $-LK-(E_1)_2$;
  $C_1-C_{12}$ alkyl optionally substituted with one or more $—NR_{19}R_{20}$, $—O-L$ and/or $—S-L$;
  $C_1-C_{12}$ haloalkyl;
  $C_4-C_8$ cycloalkenyl;
  $C_2-C_{12}$ alkynyl;
  phenyl or $—N(R_{19})$-phenyl, each of which being optionally substituted with one or more $C_1-C_6$ alkyl, halogen, nitrile, alkyloxy, $—COOR_{19}$, and/or $C_2-C_{12}$ alkylcarboxyl;
  benzoyl, naphthoyl, phenyloxycarbonyl, or naphtyloxycarbonyl, each of which being optionally substituted by one or more $C_1-C_{20}$ alkyl, $C_1-C_4$ haloalkyl, $—SR_{19}$, $—OR_{19}$, $—NR_{19}R_{20}$, halogen, phenyl, $—COOR_{19}$, $—CONR_{19}R_{20}$, $—CN$, $—NO_2$ and/or $C_3$-$C_{10}$ cycloalkyl, wherein the $C_3$-$C_{10}$ cycloalkyl may be interrupted by —O—, —(C=O)— or —N($R_{19}$)—;

—$NR_{16}R_{17}$; and/or thiophene carbonyl or pyrrolidinyl, each of which being optionally substituted with one or more $C_1$-$C_6$ alkyl, halogen, nitrile, alkyloxy, —$COOR_{19}$, and/or $C_2$-$C_{12}$ alkylcarboxyl, and each $R_{21}$ independently represents:

hydrogen;

-$E_1$;

-LK-$E_1$;

-LK-$(E_1)_2$ $C_1$-$C_{12}$ alkyl optionally substituted with one or more —$NR_{19}R_{20}$, —O-L and/or —S-L;

$C_4$-$C_8$ cycloalkenyl;

$C_2$-$C_{12}$ alkynyl; or phenyl optionally substituted with one or more $C_1$-$C_6$ alkyl, nitrile, alkyloxy, —$COOR_{16}$, and/or $C_2$-$C_{12}$ alkylcarboxyl, and/or two $R_{21}$ attached to the same carbon atom represent =O or =$E_2$, wherein:

L represents a hydrogen atom or $C_1$-$C_6$ alkyl, $R_{16}$ and $R_{17}$ independently represent:

hydrogen, $C_1$-$C_{12}$ alkyl optionally substituted with one or more —$NR_{19}R_{20}$, —O-L and/or —S-L;

$C_4$-$C_{10}$ cycloalkyl;

$C_4$-$C_{10}$ cycloalkenyl;

$C_2$-$C_{12}$ alkynyl;

$C_1$-$C_{12}$ haloalkyl; or phenyl or benzoyl, each of which optionally substituted with one or more $C_1$-$C_6$ alkyl, halogen, nitrile, alkyloxy, —$COOR_{19}$, and/or $C_2$-$C_{12}$ alkylcarboxyl group, and $R_{19}$ and $R_{20}$ independently represent hydrogen, $C_1$-$C_{12}$ alkyl; $C_1$-$C_{12}$ haloalkyl; $C_4$-$C_8$ cycloalkenyl; or $C_2$-$C_{12}$ alkynyl, provided that the compound comprises at least one oxime ester or acyl group, and provided that when $R_{21}$ is attached to a nitrogen atom and $R_{21}$ is -$E_1$, -$E_1$ is not —$CR_6$=N—O—(C=O)—$R_7$.

39. The compound of item 38 being of formula:

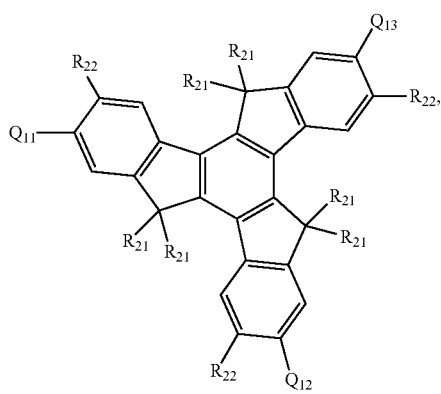

Formula 1'

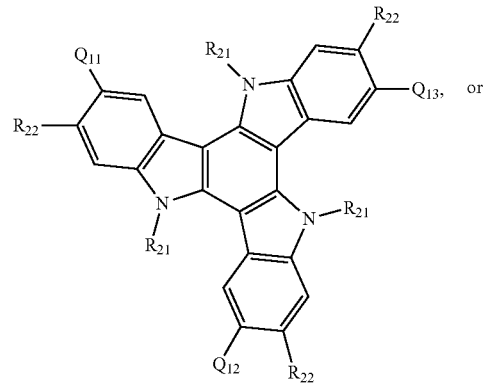

Formula 2'

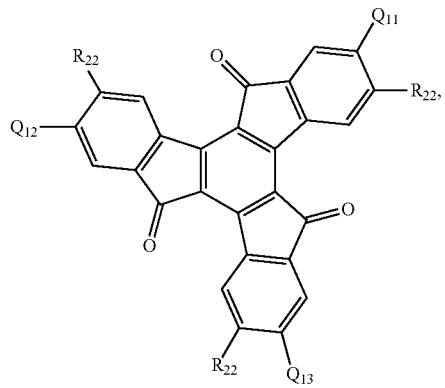

Formula 3' wherein:

each of $Q_{11}$, $Q_{12}$ and $Q_{13}$ independently represent:

hydrogen;

-$E_1$;

-LK-$E_1$;

-LK-$(E_1)_2$;

$C_1$-$C_{12}$ alkyl optionally substituted with one or more —$NR_{19}R_{20}$, —O-L and/or —S-L;

$C_1$-$C_{12}$ haloalkyl;

$C_4$-$C_8$ cycloalkenyl;

$C_2$-$C_{12}$ alkynyl;

phenyl or —N($R_{19}$)-phenyl, each of which being optionally substituted with one or more $C_1$-$C_6$ alkyl, halogen, nitrile, alkyloxy, —$COOR_{19}$, and/or $C_2$-$C_{12}$ alkylcarboxyl;

benzoyl, naphthoyl, phenyloxycarbonyl, or naphtyloxycarbonyl, each of which being optionally substituted by one or more $C_1$-$C_{20}$ alkyl, $C_1$-$C_4$ haloalkyl, —$SR_{19}$, —$OR_{19}$, —$NR_{19}R_{20}$, halogen, phenyl, —$COOR_{19}$, —$CONR_{19}R_{20}$, —CN, —$NO_2$ and/or $C_3$-$C_{10}$ cycloalkyl, wherein the $C_3$-$C_{10}$ cycloalkyl may be interrupted by —O—, —(C=O)— or —N($R_{19}$)—;

—$NR_{16}R_{17}$; or thiophene carbonyl or pyrrolidinyl, each of which being optionally substituted with one or more $C_1$-$C_6$ alkyl, halogen, nitrile, alkyloxy, —$COOR_{19}$, and/or $C_2$-$C_{12}$ alkylcarboxyl, each $R_{22}$ independently represents:

hydrogen;

$C_1$-$C_{12}$ alkyl optionally substituted with one or more —$NR_{19}R_{20}$, —O-L and/or —S-L;

$C_1$-$C_{12}$ haloalkyl;

$C_4$-$C_8$ cycloalkenyl;

$C_2$-$C_{12}$ alkynyl;

phenyl or —N($R_{19}$)-phenyl, each of which being optionally substituted with one or more $C_1$-$C_6$ alkyl, halogen, nitrile, alkyloxy, —COOR$_{19}$, and/or $C_2$-$C_{12}$ alkylcarboxyl; or benzoyl, naphthoyl, phenyloxycarbonyl, or naphtyloxycarbonyl, each of which being optionally substituted by one or more $C_1$-$C_{20}$ alkyl, $C_1$-$C_4$ haloalkyl, —SR$_{19}$, —OR$_{19}$, —NR$_{19}$R$_{20}$, halogen, phenyl, —COOR$_9$, —CONR$_{19}$R$_{20}$, —CN, —NO$_2$ and/or $C_3$-$C_{10}$ cycloalkyl, wherein the $C_3$-$C_{10}$ cycloalkyl is interrupted by —O—, —(C=O)— or —N(R$_{19}$)—, wherein $R_{16}$, $R_{17}$, $R_{19}$, $R_{20}$, $R_{21}$, and L are as defined in item 38, provided that the compound comprises at least one oxime ester or acyl group, and provided that when $R_{21}$ is attached to a nitrogen atom and $R_{21}$ is -E$_1$, -E$_1$ is not —CR$_6$=N—O—(C=O)—R$_7$.

40. The compound according to item 38 or 39, wherein -LK-E$_1$ represents:

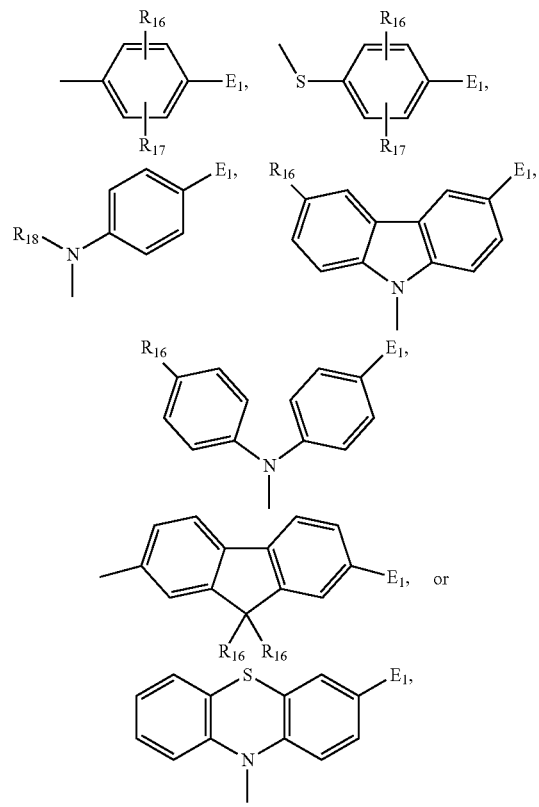

and -LK-(E$_1$)$_2$ represents:

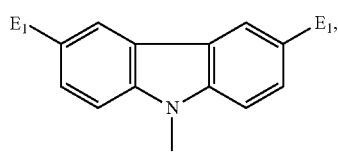

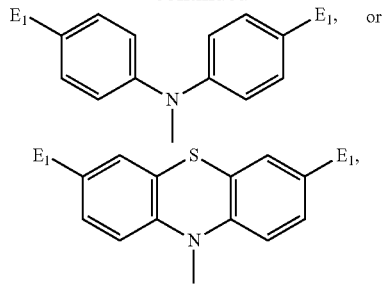

wherein $R_{18}$ is hydrogen or $C_1$-$C_{12}$ alkyl optionally substituted with one or more —O-L and/or —S-L, and wherein L, $R_{16}$ and $R_{17}$ are as defined in item 38.

41. The compound of any one of items 38 to 40, wherein each Q, $Q_1$, $Q_2$, and $Q_3$, when present, represents one -E$_1$ of formula —CR$_6$=N—O—(C=O)—R$_7$, wherein $R_6$ represents $C_1$-$C_{12}$ alkyl optionally substituted with —O-L, wherein L is $C_1$-$C_6$ alkyl, and $R_7$ represents $C_1$-$C_{12}$ alkyl;

all $R_{22}$, when present, represent hydrogen; and all $R_{21}$, when present, represent hydrogen or $C_1$-$C_{12}$ alkyl.

42. The compound of any one of items 38 to 40, wherein:

each Q, $Q_{11}$, $Q_{12}$, and $Q_{13}$, when present, represents one -LK-E$_1$, wherein E$_1$ is of formula —CR$_6$=N—O—(C=O)—R$_7$, wherein $R_6$ represents $C_1$-$C_{12}$ alkyl optionally substituted with —O-L, wherein L is $C_1$-$C_6$ alkyl, and $R_7$ represents $C_1$-$C_{12}$ alkyl;

all $R_{22}$, when present, represent hydrogen;

all $R_{21}$, when present, represents hydrogen or $C_1$-$C_{12}$ alkyl; and

LK represents

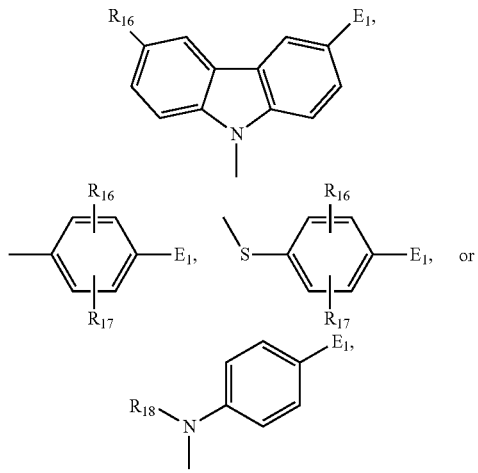

wherein $R_{16}$ is hydrogen or benzoyl substituted with $C_1$-$C_6$ alkyl, $R_{17}$ represents hydrogen and $R_{18}$ represents $C_1$-$C_{12}$ alkyl.

43. The compound of any one of items 38 to 40, wherein each of $Q_{11}$, $Q_{12}$, and $Q_{13}$, when present, represents hydrogen, each of Q and $R_{22}$, when present, represents one —N($R_{19}$)-phenyl wherein $R_{19}$ represents $C_1$-$C_{12}$ alkyl, and every pair of $R_{21}$ attached to a common carbon atom represent =E$_2$ wherein $R_7$ represents $C_1$-$C_{12}$ alkyl.

44. The compound of any one of items 38 to 40, wherein each Q, $Q_1$, $Q_2$, and $Q_3$, when present, represents one -LK-$E_1$ or -$E_1$, wherein $E_1$ is of formula —C(=O)—$R_{30}$, wherein $R_{30}$ represents $C_1$-$C_{12}$ linear alkyl, phenyl, phenyl substituted with alkyl or alkyloxy, or thiophenyl;

all $R_{22}$, when present, represent hydrogen;
all $R_{21}$, when present, represent $C_1$-$C_{12}$ alkyl, and
-LK- represents 2-phenylene or 4-phenylene.

45. The compound of any one of items 36 to 40, being of formula:

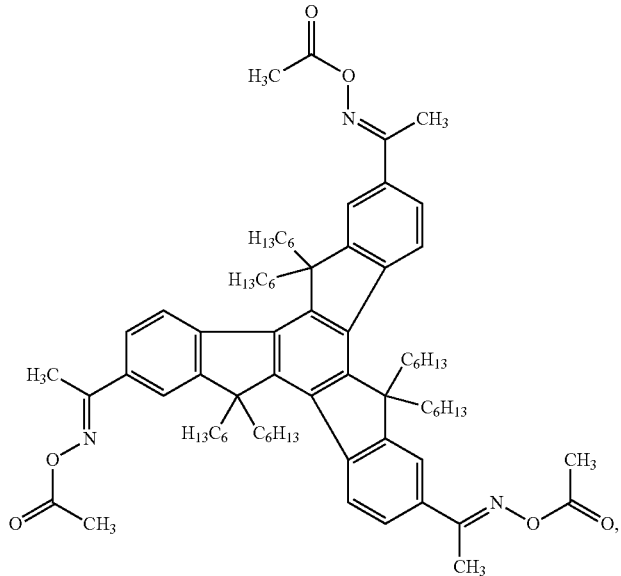

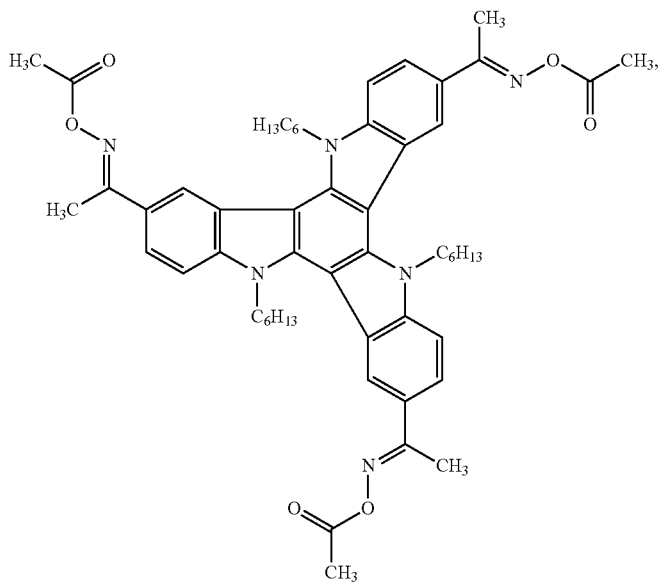

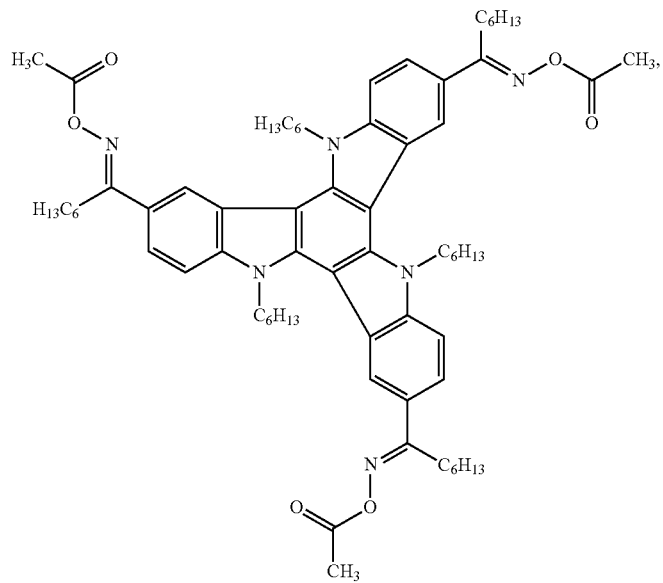
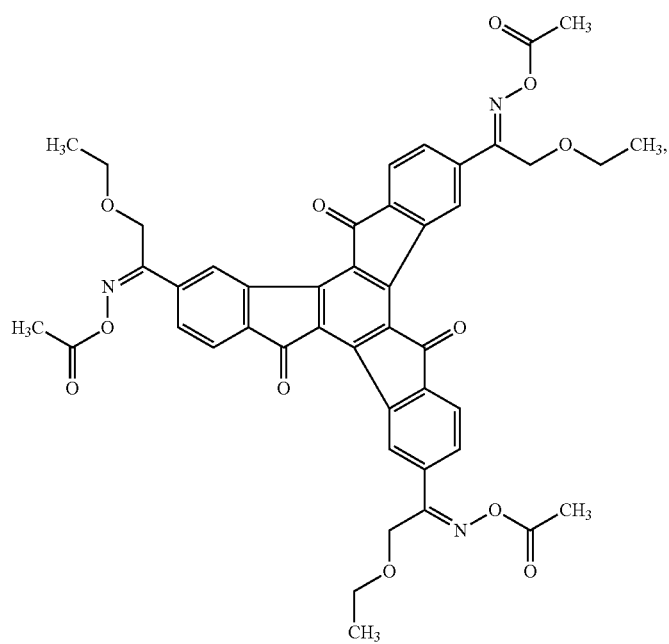

-continued
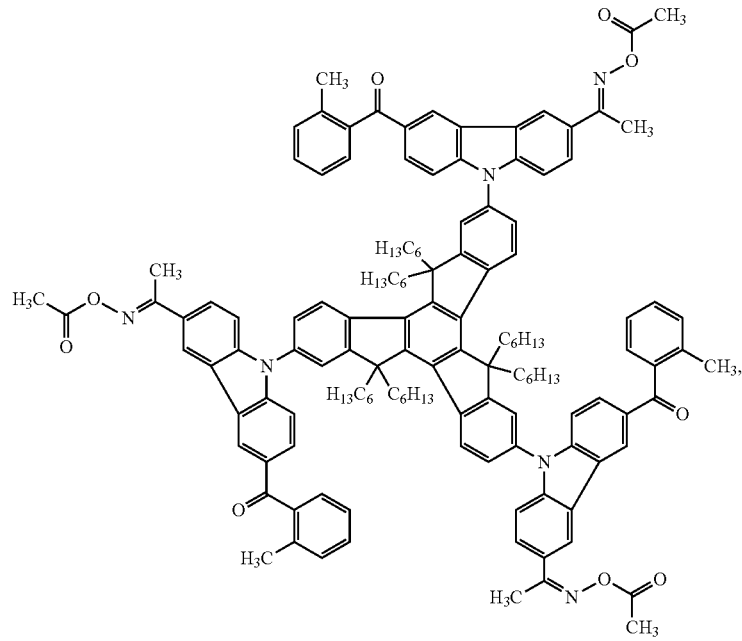
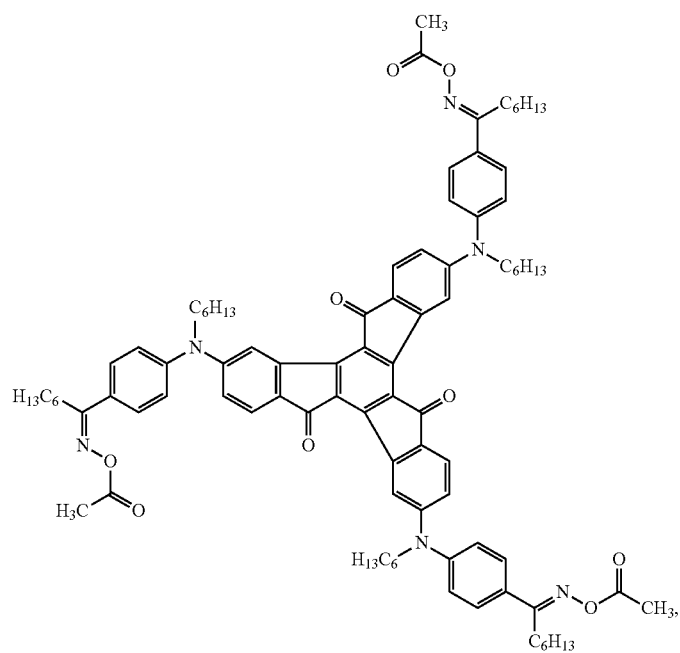

-continued
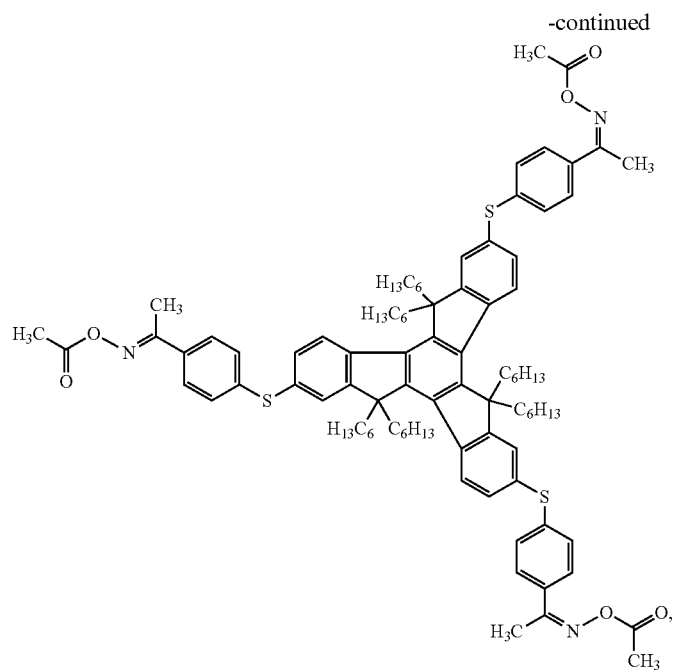
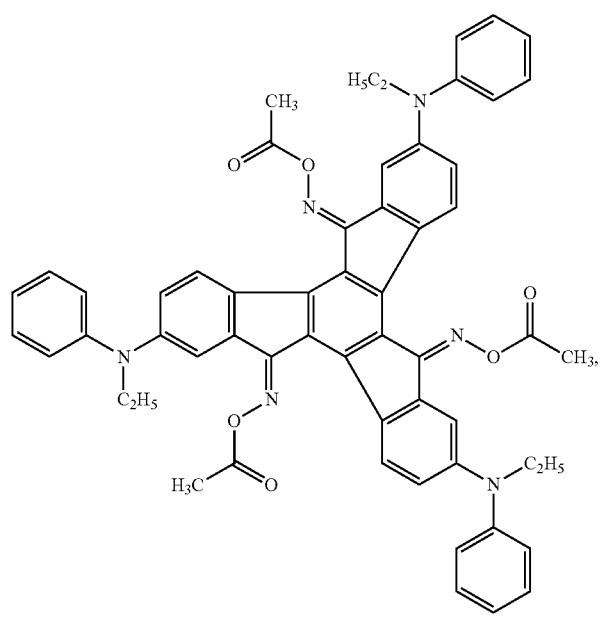

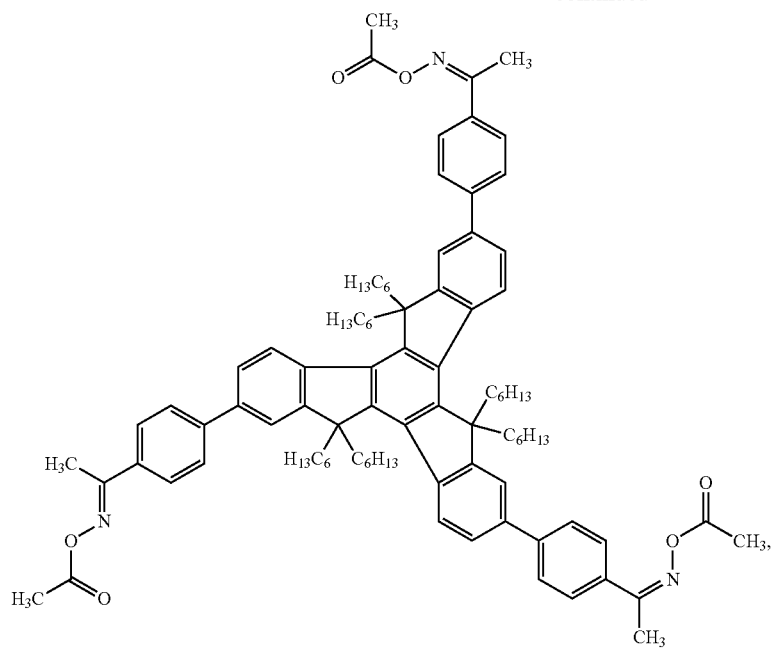
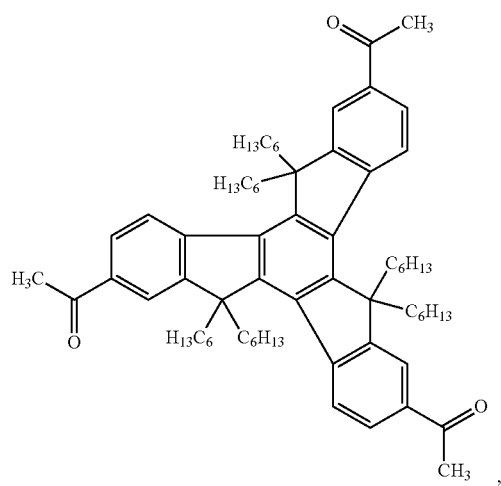
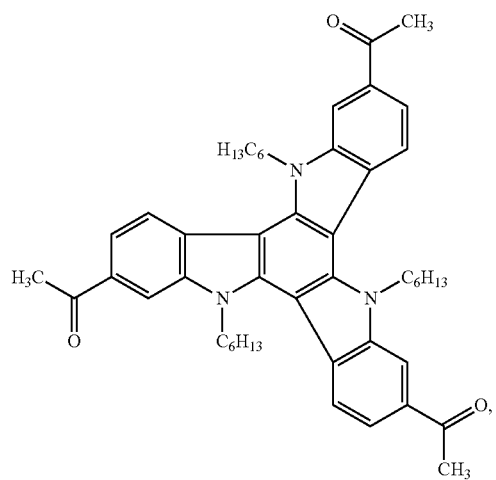

-continued
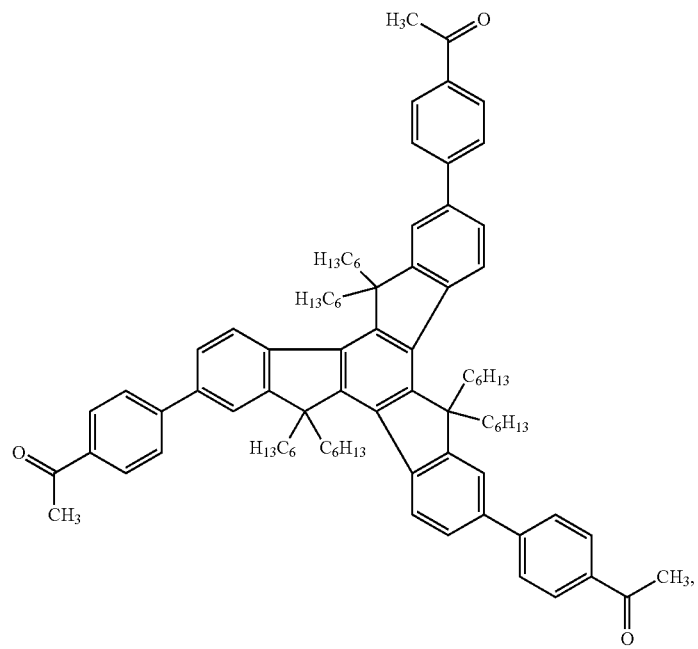
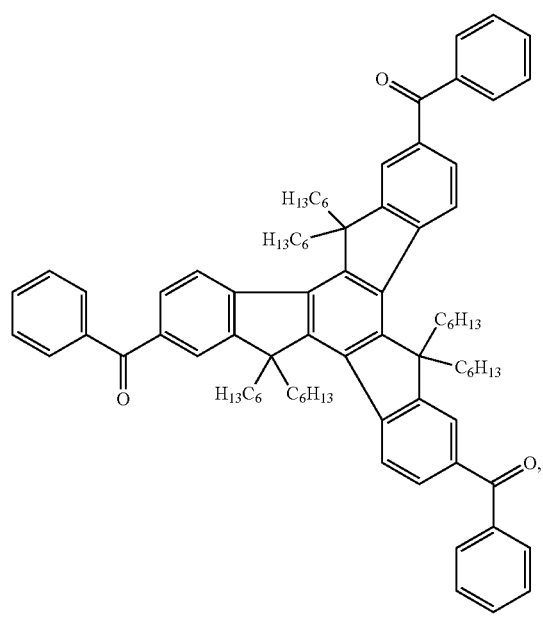

-continued
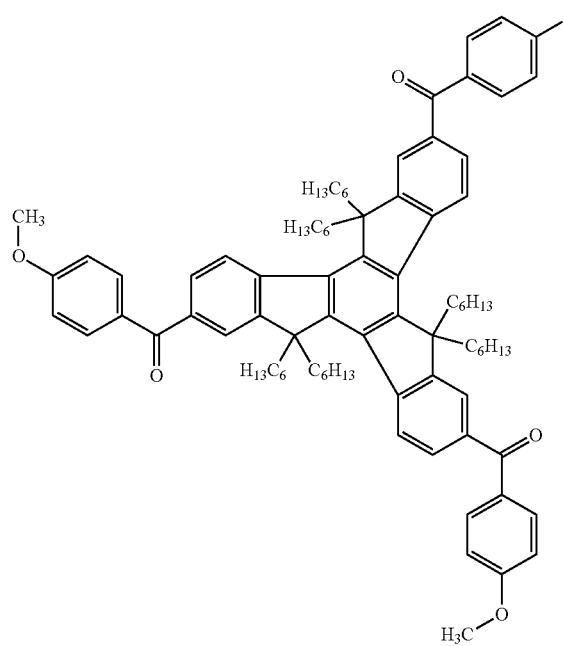
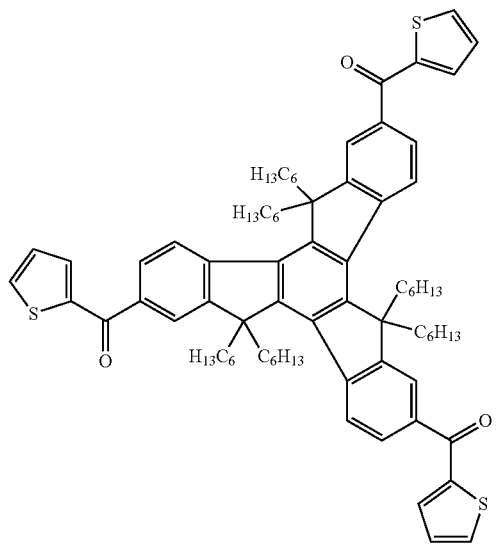
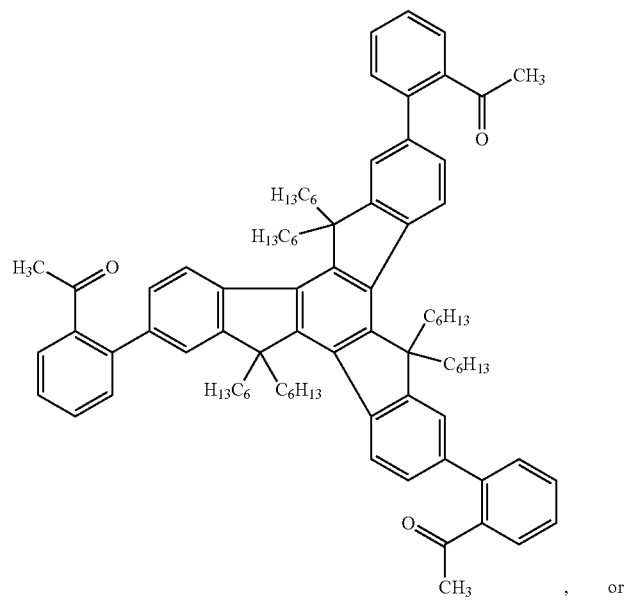, or

-continued

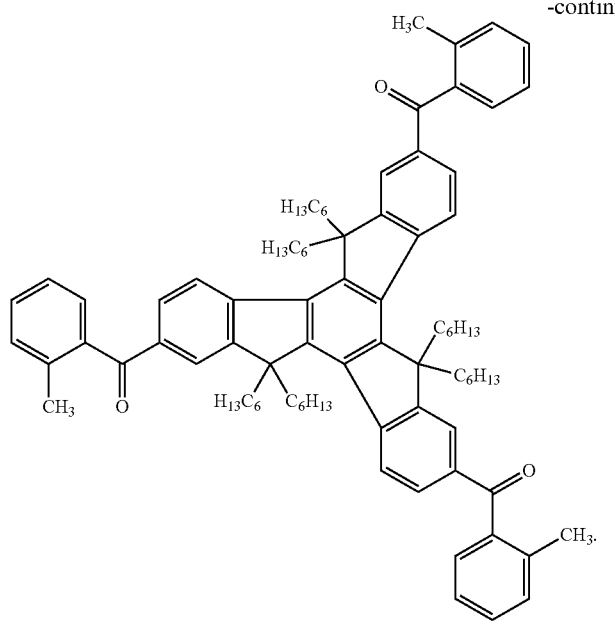

46. The compound of any one of items 1 to 45 for use as a photoinitiator in a photopolymerizable composition.
47. The compound of any one of items 1 to 45 being comprised in a photopolymerizable composition.
48. The compound of item 46 or 47, wherein the photopolymerizable composition is a lithographic printing plate composition.
49. The compound of item 46 or 47, wherein the photopolymerizable composition is a color filter resist composition.
50. The compound of item 46 or 47, wherein the photopolymerizable composition is a black matrix resin composition.
51. The compound of item 46 or 47, wherein the photopolymerizable composition is a photosetting or photocuring ink.
52. The compound of item 46 or 47, wherein the photopolymerizable composition is an oxygen scavenging film composition.
53. A photopolymerizable composition comprising a compound according to any one of items 1 to 45.
54. The photopolymerizable composition of item 53 being a lithographic printing plate composition.
55. The photopolymerizable composition of item 53 being a color filter resist composition.
56. The photopolymerizable composition of item 53 being a black matrix resin composition.
57. The photopolymerizable composition of item 53 being a photosetting or photocuring ink.
58. The photopolymerizable composition of item 53 being an oxygen scavenging film composition.

DETAILED DESCRIPTION OF THE INVENTION

The Compounds of the Invention

Turning now to the invention in more details, there is provided a compound comprising optionally substituted

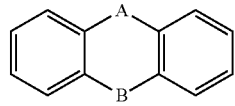
(FORMULA I)

fused with one or two optionally substituted

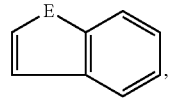
(FORMULA II)

wherein A and E each independently represent —CH$_2$—, —NH—, —O—, —S—, or —C(=O)— and B represents a bond, —CH$_2$—, —NH—, —O—, —S—, or —C(=O)—, said compound having directly or indirectly attached thereto at least one oxime ester and/or acyl group.

In FORMULA I, B can represent a bond, so this formula also represents compounds of formula

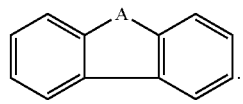

In this formula and in FORMULA I, A and B (when it is not a bond) independently represent —CH$_2$—, —NH—, —O—, —S—, or —C(=O)—. Therefore, FORMULA I includes:

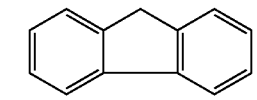, 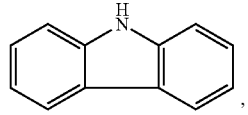, (fluorene, also called 9H-fluorene)   (9H-carbazole)

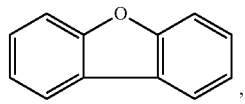, 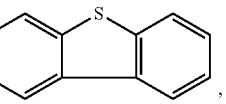, (dibenzo[b,d]furan)   (dibenzo[b,d]thiophene)

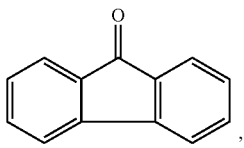, 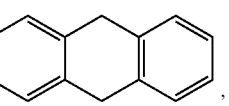, (9H-fluoren-9-one)   (9,10-dihydroanthracene)

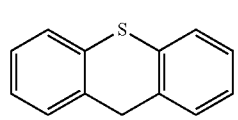, 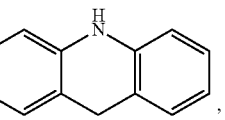, (9H-thioxanthene)   (9,10-dihydroacridine)

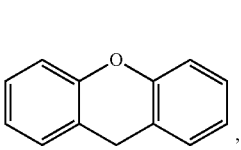, 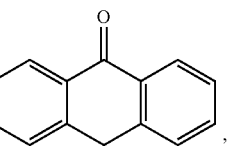, (9H-xanthene)   (anthracen-9(10H)-one)

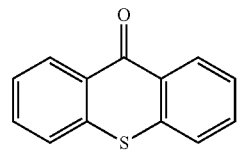, 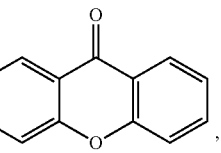, (9H-thioxanthen-9-one)   (9H-xanthen-9-one)

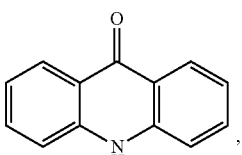, 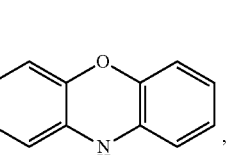, (acridin-9(10H)-one)   (10H-phenoxazine)

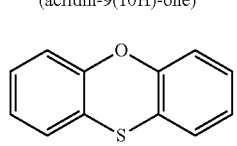, 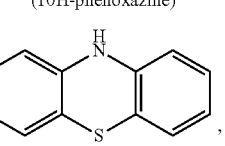, (phenoxathiin)   (10H-phenothiazine)

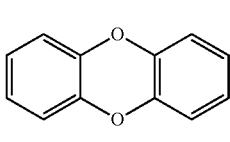, 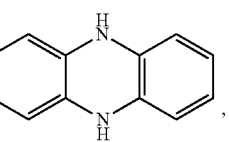, (oxanthrene)   (5,10-dihydrophenazine)

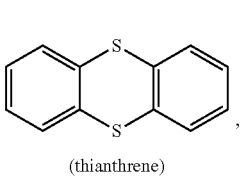, and 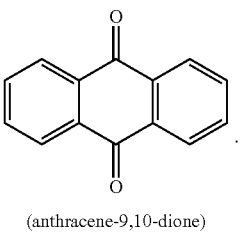.

(thianthrene)   (anthracene-9,10-dione)

Similarly, FORMULA II includes:

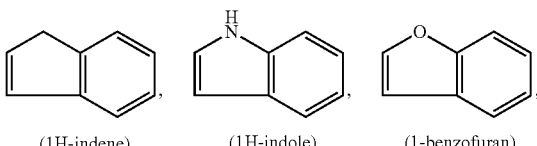

(1H-indene)   (1H-indole)   (1-benzofuran)

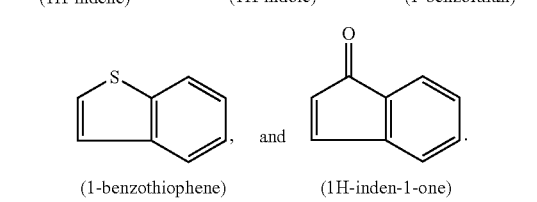

(1-benzothiophene)   (1H-inden-1-one)

In the compound of the invention, FORMULA I is fused with one or two FORMULA II. Herein, FORMULA I being fused with FORMULA II means that one ring of FORMULA I will share a bond with one ring of FORMULA II so as to form a phenyl/5-membered ring/phenyl structure as, for example, in the following compound:

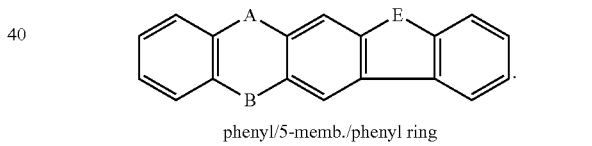

phenyl/5-memb./phenyl ring

The bonds that participate in the fusion of a FORMULA I with a first FORMULA II are those marked with stars in the following formulas:

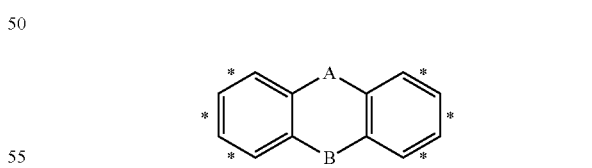

(i.e. all the bonds between carbon atoms that bear at least one hydrogen atom each) and

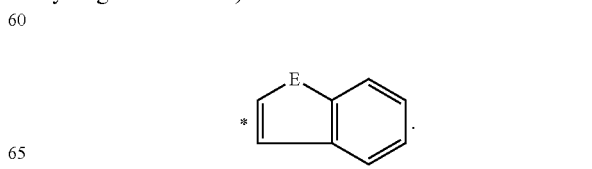.

Therefore, FORMULA I fused with FORMULA II includes:

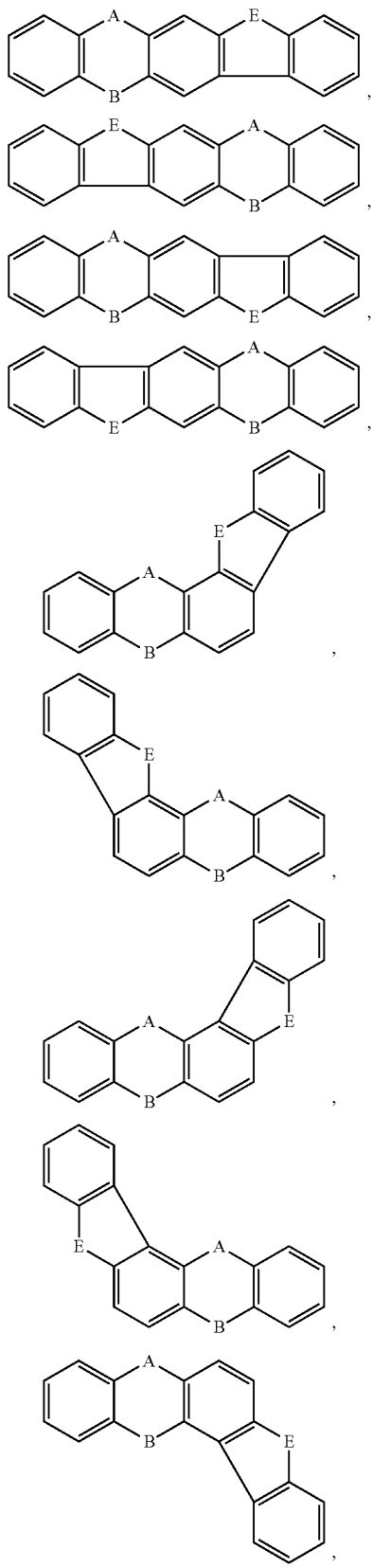

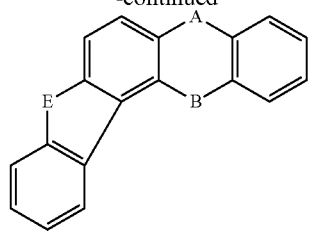

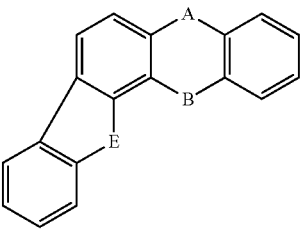

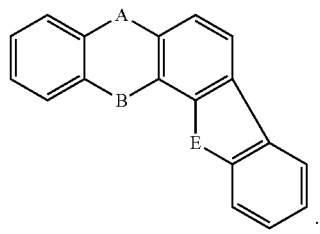

, and

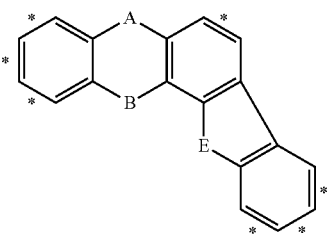

When a second FORMULA II is present, it may be the same or different from the first FORMULA II. Also, it may be fused with either phenyl group of FORMULA I or with the phenyl group of the first FORMULA II. For example, for the last FORMULA I-FORMULA II structure shown in the previous paragraph, the second FORMULA II can be fused at the following location:

(i.e. again all the bonds between carbon atoms that bear at least one hydrogen atom each).

Again, the second FORMULA II is fused so as to form a phenyl/5-membered ring/phenyl structure. Therefore, for each of the FORMULA I-FORMULA II structures shown in the previous paragraph, there are 14 different ways of fusing a second FORMULA II. These 14 ways are shown below for the last FORMULA I-FORMULA II structure of the previous paragraph only; the skilled person will understand from this example how to fuse a second FORMULA II on any of the above FORMULA I-FORMULA II structure. These 14 ways are:

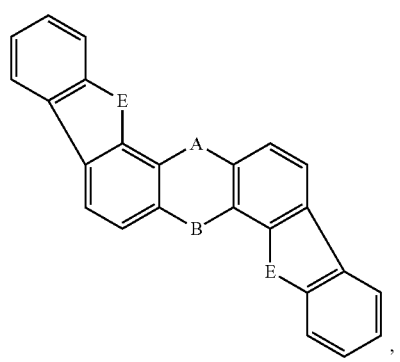
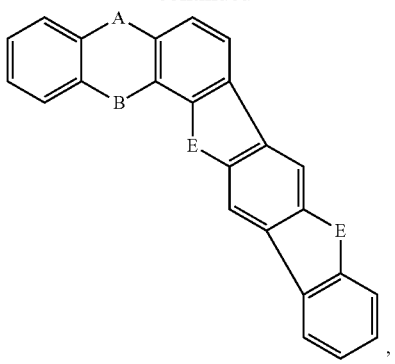
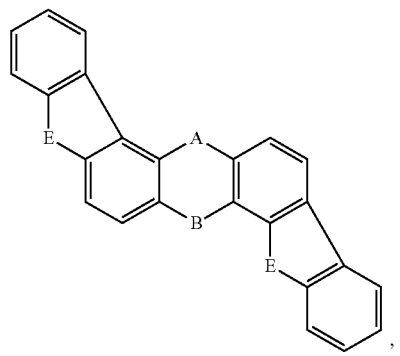
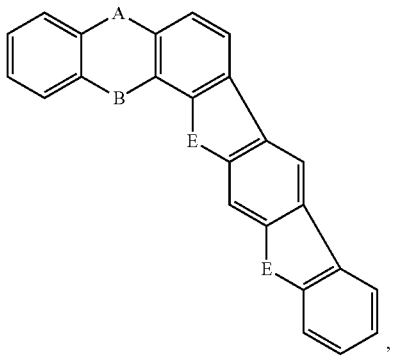
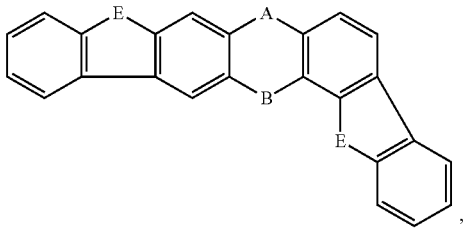
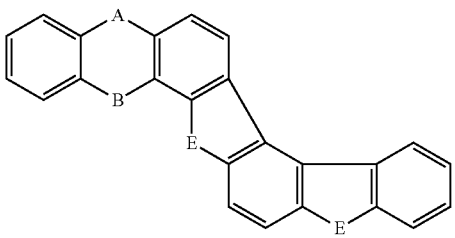
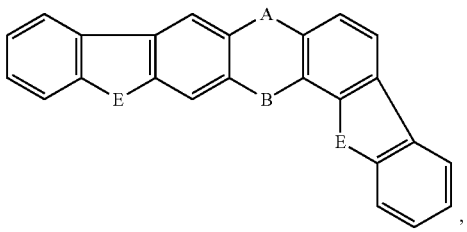
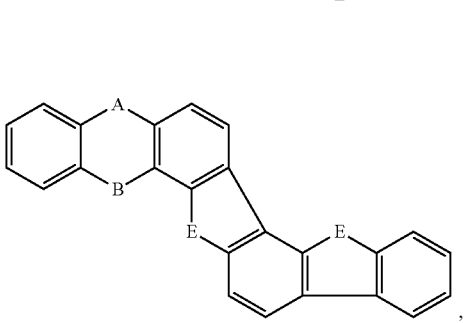
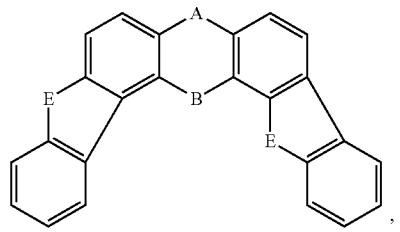
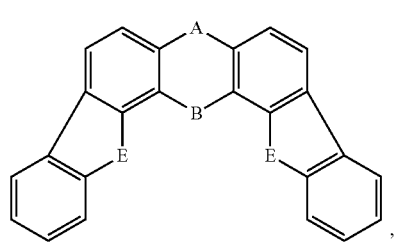
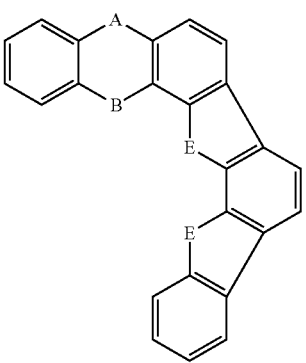

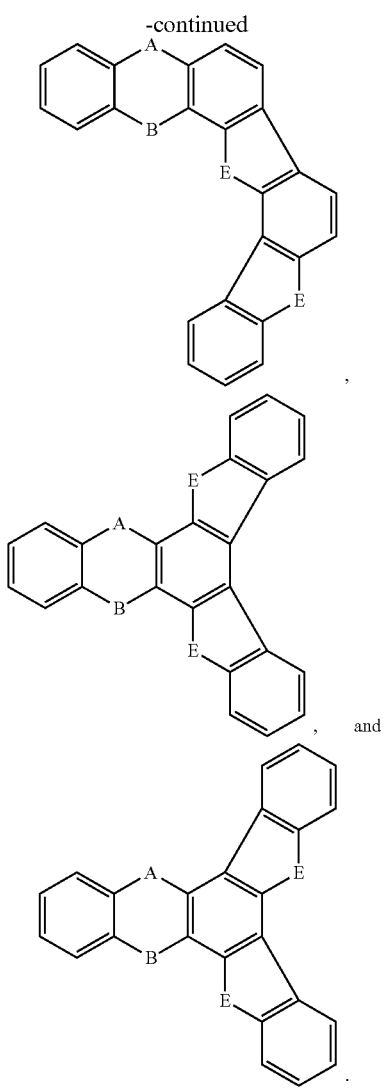

,

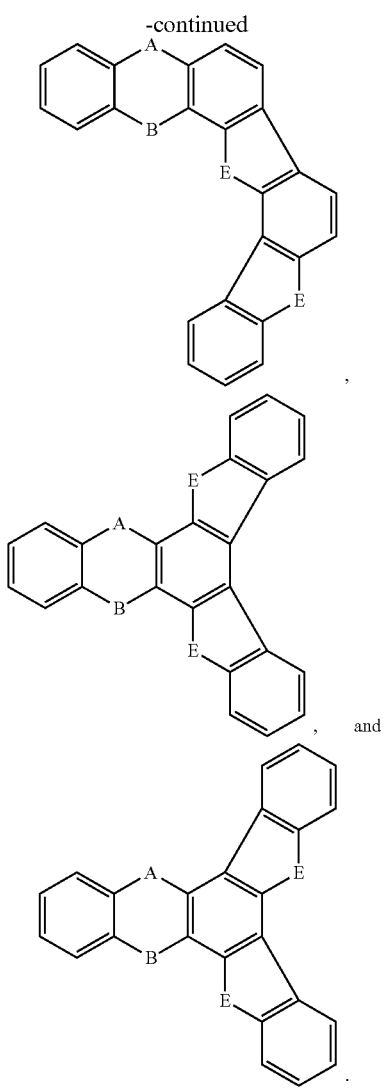

, and

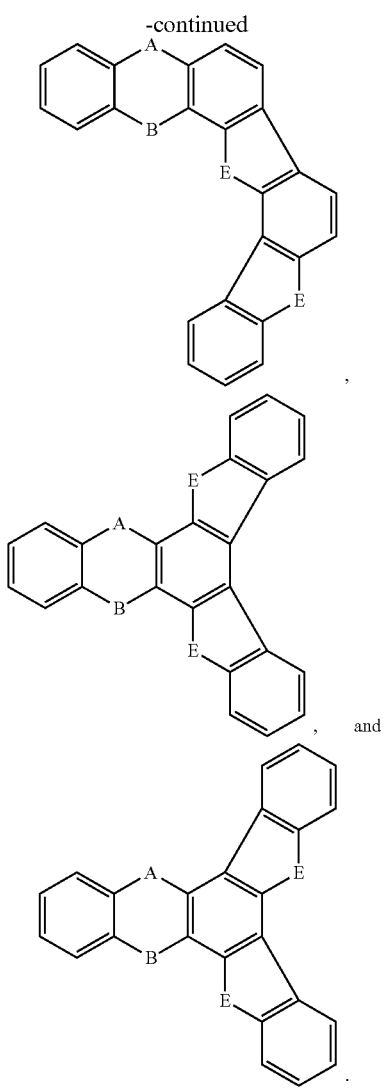

.

It should be noted that when B is a bond, the last structure of the previous paragraph corresponds to truxene-like compounds. In embodiments of the invention, the compound is truxene (i.e. when B is a bond and A and E are —CH₂—), truxenone (i.e. when B is a bond and A and E are —C(=O)—), triazatruxene (i.e. when B is a bond and A and E are —NH—), or a derivative thereof.

For more certainty, herein, "truxene" refers to a compound of formula:

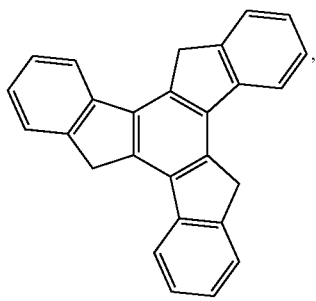 [SMILES: c1ccc2c(c1)Cc1c-2c2c(c3c1-c1ccccc1C3)-c1ccccc1C2]

or with all the hydrogen atoms shown:

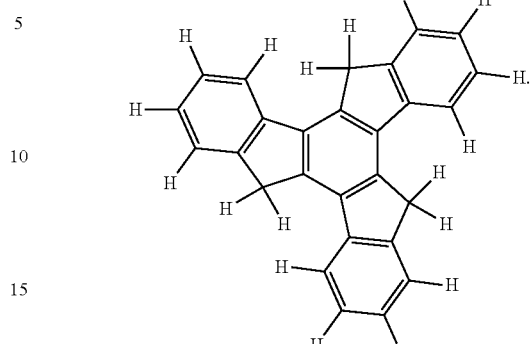

Herein, truxenone refers to a compound of formula:

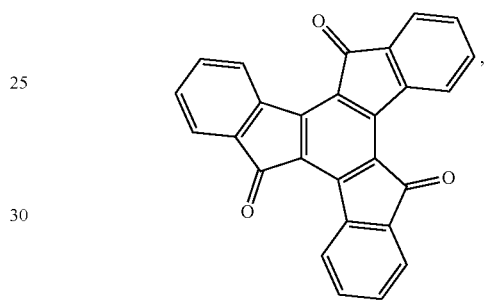

or with all the hydrogen atoms shown:

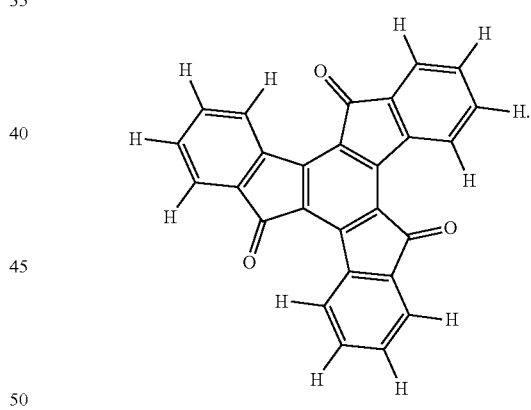

Herein, "triazatruxene" refers to a compound, also known as 5,10,15-triazatruxene, that is of formula:

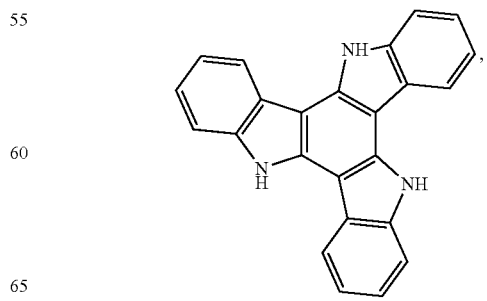

or with all the hydrogen atoms shown:

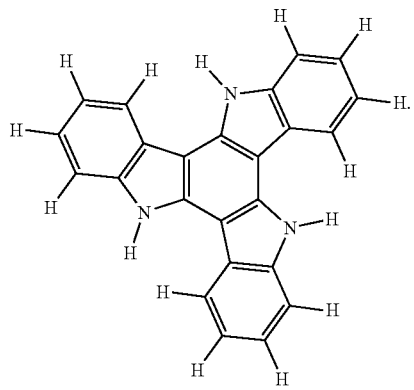

Truxene, truxenone, and triazatruxene bear CAS numbers 548-35-6, 4430-15-3 and 109005-10-9, respectively.

Embodiments in which the fusion of FORMULA I with two FORMULA II produces truxene, truxenone, triazatruxene and derivatives thereof will be discussed further below after the following more general discussion of the compounds of the invention.

In the compounds of the invention, FORMULA I and FORMULA II are "optionally substituted". This means that one or more hydrogen atoms of FORMULA I and/or FORMULA II (including the hydrogen atoms in the A, B and E groups) can be replaced by substituents. The nature of these substituents is not crucial to the invention as long as they do not prevent the compound of the invention to act as a photoinitiator.

In embodiments, FORMULA I and FORMULA II are optionally substituted by one or more:
  $C_1$-$C_{12}$ alkyl, $C_1$-$C_{12}$ alkyloxy, $C_4$-$C_{10}$ cycloalkyl, $C_1$-$C_{12}$ alkenyl, $C_4$-$C_{10}$ cycloalkenyl, $C_4$-$C_{10}$ cycloalkenyl, $C_2$-$C_{12}$ alkynyl, and/or, $C_4$-$C_{10}$ cycloalkynyl, each of which being optionally substituted with one or more:
    $NR_8R_9$,
    —O-L,
    —S-L, and/or
    phenyl optionally substituted with one or more $C_1$-$C_6$ alkyl, halogen atom, nitrile, alkyloxy, $COOR_{10}$, and/or $C_2$-$C_{12}$ alkylcarboxyl; and/or
  phenyl, biphenyl and/or naphthyl, each of which being optionally substituted with one or more:
    $C_1$-$C_6$ alkyl,
    halogen atom,
    nitrile,
    alkyloxy,
    —$COOR_{10}$, and/or
    $C_2$-$C_{12}$ alkylcarboxyl,
wherein L is a hydrogen atom or $C_1$-$C_6$ alkyl, and wherein each of $R_8$, $R_9$ and $R_{10}$ is independently an hydrogen atom, $C_1$-$C_{12}$ alkyl; $C_4$-$C_{10}$ cycloalkyl; $C_1$-$C_{12}$ alkenyl; $C_4$-$C_{10}$ cycloalkenyl; $C_2$-$C_{12}$ alkynyl; $C_4$-$C_{10}$ cycloalkynyl; $C_1$-$C_{12}$ haloalkyl; or optionally substituted aryl, such as unsubstituted or substituted phenyl and naphthyl. In embodiments, the optionally substituted aryl is substituted with alkyl or alkyloxy.

In more specific embodiments, one or more of these substituents are located on the phenyl rings of FORMULA I and FORMULA II that are not involved in a fusion between FORMULA I and FORMULA II. For example, this would be the phenyl rings circled in the following formula:

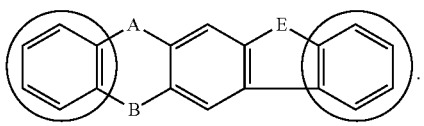

There may be from zero to four substituents on such a phenyl ring.

In the same or other embodiments, one or more of these substituents are located on the carbon and nitrogen atoms of the A, B and E groups. Therefore, one or both of the hydrogen atoms of —$CH_2$— in A, B and E can independently be replaced by such a substituent. Similarly, the hydrogen atom of —NH— in A, B and E can be replaced by such a substituent.

In the same or other embodiments, one or more of the above substituents are located on the phenyl rings that are involved in a fusion between FORMULA I and FORMULA II (this would be the phenyl ring that is not circled in the above example). There may be from zero to two substituents on such a phenyl ring.

The compounds of the invention have attached thereto, directly or indirectly, at least one oxime ester and/or acyl group. Herein, "having attached thereto" means that one or two hydrogen atoms on a carbon or nitrogen atom of the compound (including the hydrogen atoms in the A, B and E groups) are replaced by an oxime ester or acyl group.

The oxime ester groups and the acyl groups can be directly or indirectly attached. Herein, "directly or indirectly attached" means that there can be a linker (-LK-) between the group and FORMULA I or FORMULA II. When such a linker is present, the group is said to be indirectly attached, otherwise it is directly attached.

In embodiments, -LK- is optionally substituted alkylene, cycloalkylene, alkenylene, cycloalkenylene, alkynylene, cycloalkynylene, arylene, —S-arylene, —NH-arylene, or —N(aryl)-arylene, each of which optionally comprising one or more oxygen atom, sulfur atom, nitrogen atom, carbonyl group, carbamate group, carbamide group, and/or ester group. The nature of the substituents of these radicals is not crucial to the invention as long as they do not prevent the compound of the invention to act as a photoinitiator. These substituents may replace any hydrogen atoms of these groups, including the hydrogen atom attached to the nitrogen atom in —NH-arylene. In embodiments, these substituents are one or more:
  polyethylene glycol chain,
  $C_1$-$C_{12}$ alkyl optionally substituted with one or more:
    —$NR_8R_9$,
    —O-L,
    —S-L, and/or
    phenyl optionally substituted with one or more: $C_1$-$C_6$ alkyl, halogen, nitrile, alkyloxy, $COOR_{10}$, and/or $C_2$-$C_{12}$ alkylcarboxyl;
  $C_4$-$C_{10}$ cycloalkyl, $C_2$-$C_{12}$ alkenyl, $C_4$-$C_{10}$ cycloalkenyl, $C_2$-$C_{12}$ alkynyl, $C_4$-$C_{10}$ cycloalkynyl, each of which being optionally substituted by alkyl and/or —O-L, and/or
  aryl, such as phenyl, biphenyl and naphthyl, or aryloyl, such as benzoyl, each of which being optionally substituted with one or more:
    $C_1$-$C_6$ alkyl,
    halogen,
    nitrile,
    alkyloxy,
    —$COOR_{10}$, and/or
    $C_2$-$C_{12}$ alkylcarboxyl.
wherein L, $R_8$, $R_9$ and $R_{10}$ are as defined above.

In embodiments where the linker -LK- serves to attach an acyl group, -LK- is arylene, such as phenylene.

Herein, an oxime ester group is —$CR_6$═N—O—(C═O)—$R_7$ or ═N—O—(C═O)—$R_7$, wherein $R_6$ and $R_7$ are the same or different substituents.

The nature of the $R_6$ group is not crucial to the invention as long as it does not prevent the compound of the invention to act as a photoinitiator. In embodiments, $R_6$ represents:
hydrogen;
$C_1$-$C_{12}$ alkyl optionally substituted with one or more:
  phenyl,
  halogen,
  —$NR_9R_{10}$,
  —O-L, and/or
  —S-L;
$C_4$-$C_{10}$ cycloalkyl, $C_2$-$C_{12}$ alkenyl, $C_4$-$C_{10}$ cycloalkenyl, $C_2$-$C_{12}$ alkynyl, or $C_4$-$C_{10}$ cycloalkenyl, each of which being optionally substituted by alkyl and/or —O-L; or
phenyl optionally substituted with one or more:
  $C_1$-$C_6$ alkyl,
  halogen,
  nitrile,
  alkyloxy,
  —$COOR_{10}$, and/or
  $C_2$-$C_{12}$ alkylcarboxyl,
wherein L, $R_8$, $R_9$ and $R_{10}$ are as defined above.

In embodiments, $R_6$ is alkyl optionally substituted with —O—$C_1$-$C_6$ alkyl. In more specific embodiments $R_6$ is methyl or butyl. In embodiments, $R_6$ is methyl.

In oxime ester groups, the $R_7$ group is related to the production of free radicals. Therefore, it should not comprise oxygen, nitrogen or sulfur atoms as such atoms could quench the free radicals. Also, smaller $R_7$ groups, although not essential, are preferred as they have higher rates of diffusion and therefore lead to faster polymerization.

In embodiments, $R_7$ is alkyl, cycloalkyl, alkenyl, or cycloalkenyl, each of which being optionally substituted with aryl or halogen, or $R_7$ is aryl optionally substituted with alkyl or halogen. In specific embodiments, $R_7$ represents $C_1$-$C_{12}$ alkyl optionally substituted with phenyl; $C_4$-$C_{10}$ cycloalkyl; or phenyl optionally substituted with $C_1$-$C_6$ alkyl. In embodiments, $R_7$ is $C_1$-$C_{12}$ alkyl; $C_4$-$C_{10}$ cycloalkyl; or phenyl. In embodiments, $R_7$ is methyl.

There are two ways in which the oxime ester group can be attached to FORMULA I or FORMULA II. First, if the oxime ester group replaces two hydrogen atoms attached to the same carbon atom in FORMULA I or FORMULA II, the oxime ester group may be ═N—O—(C═O)—$R_7$, in which the nitrogen atom (═N) is directly attached though a double bond to the carbon atom (of FORMULA I or FORMULA II) that was bearing the two hydrogen atoms. Secondly, if the oxime ester group replaces only one hydrogen atom on a nitrogen or carbon atom in FORMULA I or FORMULA II, the oxime ester group will be —$CR_6$═N—O—(C═O)—$R_7$. In this case, the oxime ester group can be attached directly to the atom that was bearing the hydrogen atom, or it may be attached to a linker (-LK-) that is itself attached to the that atom (i.e. it can be indirectly attached).

It is to be noted that the first carbon atom of the oxime ester group (i.e. the carbon atom bearing the $R_6$ group and that which is underlined in the following —$\underline{C}R_6$═N—O—(C═O)—$R_7$) should preferably be attached to a carbon atom of FORMULA I or FORMULA II, rather than an oxygen, nitrogen or sulfur atom, in order to increase the thermal stability of the compound. Therefore, when the oxime ester group replaces a hydrogen atom on a nitrogen atom, a linker should optimally be used. Also, in all cases where a linker is used, the atom of this linker that is bonding with the first carbon atom of the oxime ester group as defined above should optimally be a carbon atom. Otherwise, the nature of the linker is not crucial to the invention.

Herein, an acyl group is a group of formula —C(═O)—$R_{30}$, wherein $R_{30}$ is a substituent. The nature of $R_{30}$ is not crucial to the invention as long as it does not prevent the compound of the invention to act as a photoinitiator.

In embodiments, $R_{30}$ is optionally substituted alkyl, cycloalkyl, alkenyl, cycloalkenyl, alkynyl, cycloalkynyl, or aryl, each of which optionally comprising one or more oxygen atom, sulfur atom, nitrogen atom, carbonyl group, carbamate group, carbamide group, and/or ester group. The nature of the substituents of these radicals is not crucial to the invention as long as they do not prevent the compound of the invention to act as a photoinitiator. In embodiments, these substituents are one or more:
polyethylene glycol chain,
$C_1$-$C_{12}$ alkyl optionally substituted with one or more:
  —$NR_8R_9$,
  —O-L,
  —S-L, and/or
  phenyl optionally substituted with one or more: $C_1$-$C_6$ alkyl, halogen, nitrile, alkyloxy, $COOR_{10}$, and/or $C_2$-$C_{12}$ alkylcarboxyl;
$C_4$-$C_{10}$ cycloalkyl, $C_2$-$C_{12}$ alkenyl, $C_4$-$C_{10}$ cycloalkenyl, $C_2$-$C_{12}$ alkynyl, $C_4$-$C_{10}$ cycloalkynyl, each of which being optionally substituted by alkyl and/or —O-L, and/or
aryl, such as phenyl, thiophenyl, biphenyl and naphthyl, each of which being optionally substituted with one or more:
  $C_1$-$C_6$ alkyl,
  halogen,
  nitrile,
  alkyloxy,
  —$COOR_{10}$, and/or
  $C_2$-$C_{12}$ alkylcarboxyl.
wherein L, $R_8$, $R_9$ and $R_{10}$ are as defined above.

In embodiment, $R_{30}$ is linear alkyl, phenyl or thiophenyl, all of which being optionally substituted with a linear alkyl or with —O-L.

In embodiment, $R_{30}$ is methyl, 2-methylphenyl, phenyl, thiophenyl, or 4-methoxyphenyl.

Herein, "at least one oxime ester and/or acyl group" means that several hydrogen atoms in FORMULA I and/or FORMULA II can be replaced by several oxime ester groups, several acyl groups, or a combination of oxime ester and acyl groups (each being either directly or indirectly attached). When the FORMULA I and/or FORMULA II have attached thereto more than one oxime ester and/or acyl group, some of these groups can be directly attached, while others are indirectly attached. In addition, various indirectly attached groups do not need to be attached using identical linkers (-LK-).

In embodiments, a compound of the invention has attached thereto, directly or indirectly, one, two, or three oxime ester groups or one, two, or three acyl groups. In embodiments, a compound of the invention has attached thereto, directly or indirectly, two or more oxime ester groups or two or more acyl groups. In embodiments, a compound of the invention has attached thereto, directly or indirectly, three oxime ester groups or three acyl groups.

In more specific embodiments, the oxime ester and acyl groups are located on the phenyl rings of FORMULA I and FORMULA II that are not involved in a fusion between FORMULA I and FORMULA II. For example, this would be the phenyl rings circled in the following formula:

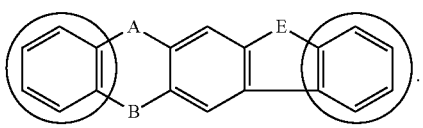

In embodiments, there may be from zero to two oxime ester and/or acyl groups on such a phenyl ring.

In the same or other embodiments, one or more oxime ester or acyl groups are located on the phenyl rings that are involved in a fusion between FORMULA I and FORMULA II (this would be the phenyl ring that is not circled in the above example).

In these and other embodiments, oxime ester and/or acyl groups may be located on the carbon and nitrogen atoms of the A, B and E groups. Therefore, one or both of the hydrogen atoms of —CH$_2$— in A, B and E can independently be replaced by such a group. Also, the hydrogen atom of —NH— in A, B and E can be replaced by an oxime ester or acyl group.

In embodiments, FORMULA 1 is optionally substituted

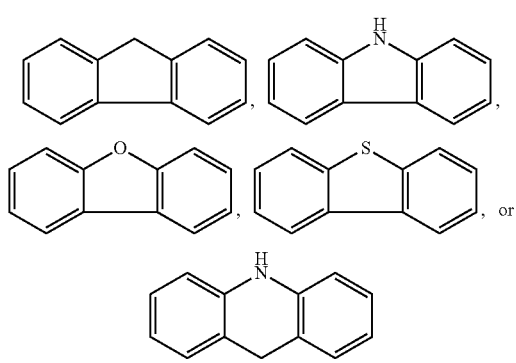

and FORMULA II is optionally substituted

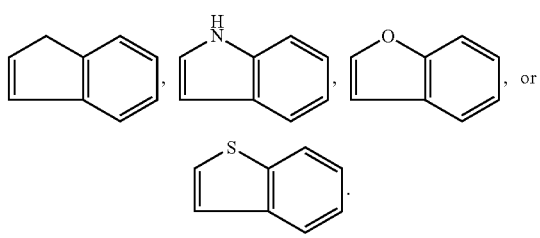

In embodiments, FORMULA 1 is optionally substituted

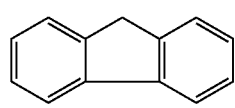 [SMILES: c1ccc2c(c1)Cc1ccccc1-2]

and FORMULA II is optionally substituted

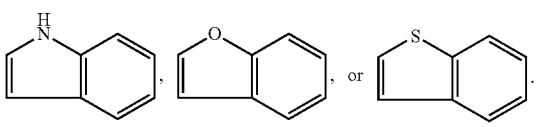

In embodiments, FORMULA 1 is optionally substituted

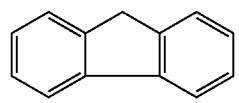

and FORMULA II is optionally substituted

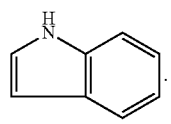

In embodiments, FORMULA 1 is optionally substituted

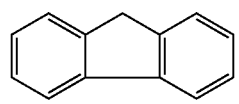 [SMILES: c1ccc2c(c1)Cc1ccccc1-2]

and FORMULA II is optionally substituted

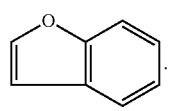

In embodiments, FORMULA 1 is optionally substituted

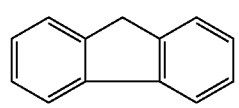

and FORMULA II is optionally substituted

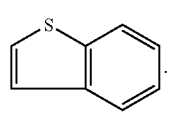

In embodiments, FORMULA 1 is optionally substituted

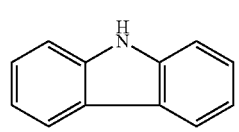 [SMILES: c1ccc2c(c1)[nH]c1ccccc12]

and FORMULA II is optionally substituted

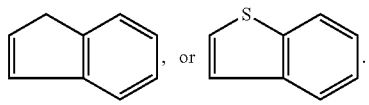

In embodiments, FORMULA 1 is optionally substituted

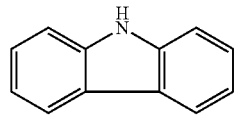 [SMILES: c1ccc2c(c1)[nH]c1ccccc12]

and FORMULA II is optionally substituted

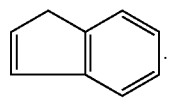

In embodiments, FORMULA 1 is optionally substituted

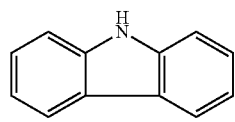 [SMILES: c1ccc2c(c1)[nH]c1ccccc12]

and FORMULA II is optionally substituted

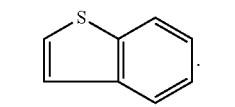

In embodiments, FORMULA 1 is optionally substituted

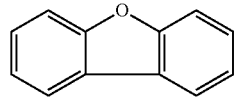

and FORMULA II is optionally substituted

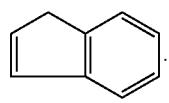

In embodiments, FORMULA 1 is optionally substituted

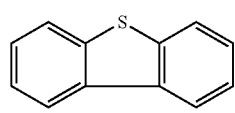 [SMILES: c1ccc2c(c1)sc1ccccc12]

and FORMULA II is optionally substituted

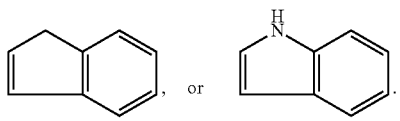 [SMILES: C1=Cc2ccccc2C1 ; c1ccc2[nH]ccc2c1]

In embodiments, FORMULA 1 is optionally substituted

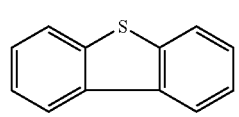 [SMILES: c1ccc2c(c1)sc1ccccc12]

and FORMULA II is optionally substituted

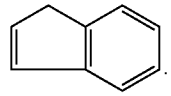

In embodiments, FORMULA 1 is optionally substituted

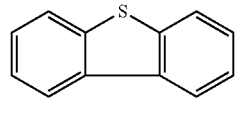

and FORMULA II is optionally substituted

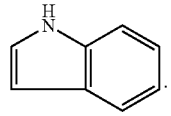

In embodiments, FORMULA 1 is optionally substituted

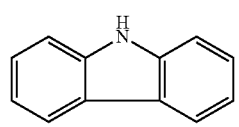 [SMILES: c1ccc2c(c1)[nH]c1ccccc12]

and FORMULA II is optionally substituted

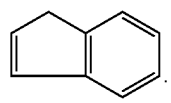

In embodiments, the compound comprises optionally substituted

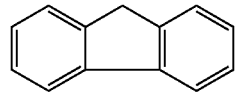 [SMILES: c1ccc2c(c1)Cc1ccccc1-2]

as FORMULA I, optionally substituted

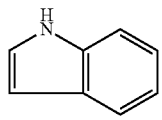

as a first FORMULA II and optionally substituted

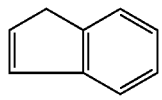

as a second FORMULA II.

In embodiments, the compound comprises optionally substituted

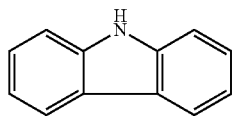 [SMILES: c1ccc2c(c1)[nH]c1ccccc12]

as FORMULA I, optionally substituted

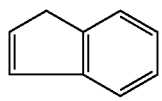

as a first FORMULA II and optionally substituted

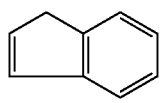

as a second FORMULA II.

In embodiments, the compound is:

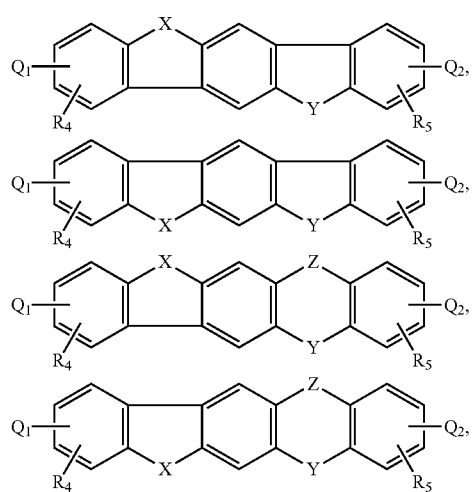

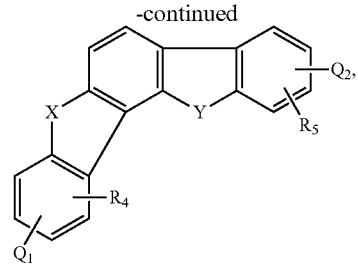

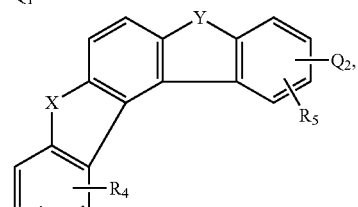

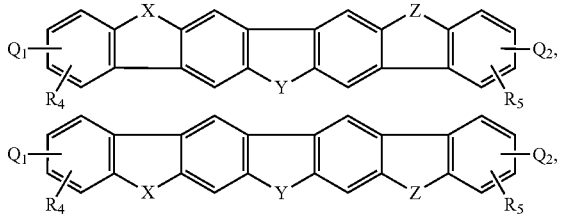

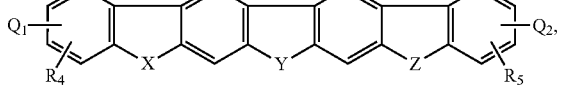

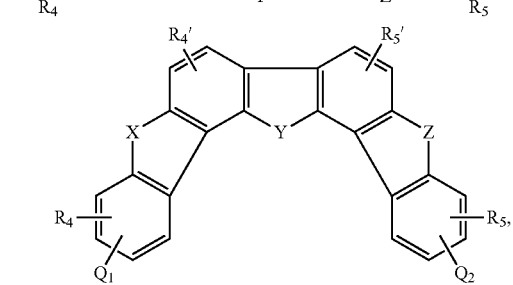

wherein:
$R_4$, $R_5$, $R_4'$ and $R_5'$ are optional and independently represent, in the case of $R_4$ and $R_5$, one to four and, in the case of $R_4'$ and $R_5'$, one or two:
  $C_1$-$C_{12}$ alkyl or alkyloxy, said alkyl and alkyloxy being optionally substituted with one or more:
    —$NR_8R_9$,
    —O-L or —S-L, and/or
    phenyl optionally substituted with one or more: $C_1$-$C_6$ alkyl, halogen atom, nitrile, alkyloxy, $COOR_{10}$, and/or $C_2$ to $C_{12}$ alkylcarboxyl;
  $C_4$-$C_{10}$ cycloalkyl, $C_2$-$C_{12}$ alkenyl, $C_4$-$C_{10}$ cycloalkenyl, $C_2$-$C_{12}$ alkynyl, $C_4$-$C_{10}$ cycloalkynyl, each of which being optionally substituted by alkyl and/or —O-L, and/or
  phenyl, biphenyl and naphthyl, each of which being optionally substituted with one or more:
    $C_1$-$C_6$ alkyl,
    halogen,
    nitrile,
    alkyloxy,
    —$COOR_{10}$, and/or
    $C_2$-$C_{12}$ alkylcarboxyl,
wherein L, $R_8$, $R_9$ and $R_{10}$ are as defined above, $Q_1$ and $Q_2$ are optional and independently represent one to four acyl groups and/or oxime ester groups of formula

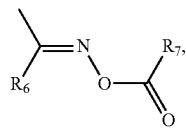

wherein $R_6$ and $R_7$ are as defined above,
each of X, Y and Z independently represent

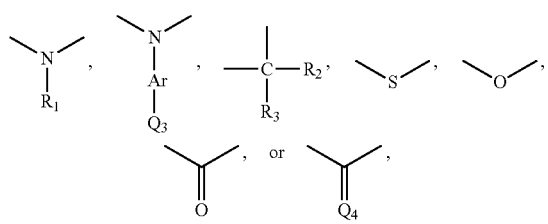

wherein:
$R_1$, $R_2$, and $R_3$ each independently represent:
a hydrogen atom;
$C_1$-$C_{12}$ alkyl optionally substituted with one or more:
—$NR_8R_9$,
—O-L,
—S-L, and/or
phenyl optionally substituted with one or more $C_1$-$C_6$ alkyl, halogen, nitrile, alkyloxy, —$COOR_{10}$, and/or $C_2$-$C_{12}$ alkylcarboxyl;
$C_4$-$C_{10}$ cycloalkyl, $C_2$-$C_{12}$ alkenyl, $C_4$-$C_{10}$ cycloalkenyl, $C_2$-$C_{12}$ alkynyl, cycloalkynyl, each of which being optionally substituted by alkyl and/or —O-L, and/or
phenyl, biphenyl or naphthyl, each of which being optionally substituted with one or more:
$C_1$-$C_6$ alkyl,
halogen,
nitrile,
alkyloxy,
—$COOR_{10}$, and/or
$C_2$-$C_{12}$ alkylcarboxyl,
wherein L, $R_8$, $R_9$ and $R_{10}$ are as defined above,
$Q_3$ represents a hydrogen atom, an acyl group, or an oxime ester group of formula:

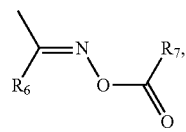

wherein $R_6$ and $R_7$ are as defined above,
$Q_4$ represents an oxime ester of formula:

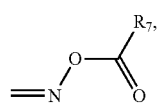

wherein $R_7$ is as defined above, and
—Ar— is a linker -LK- as define above and in more specific embodiments, an optionally substituted arylene as defined above with respect to -LK-,
with the proviso that the compound comprise at least one acyl or oxime ester group.
In more specific embodiments, the compound is:

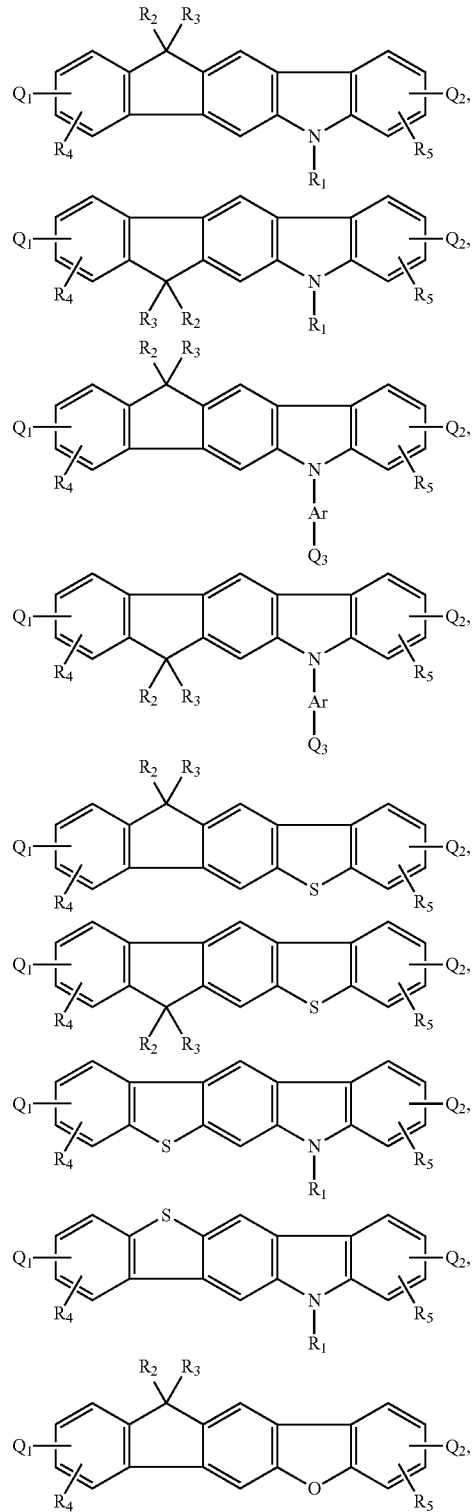

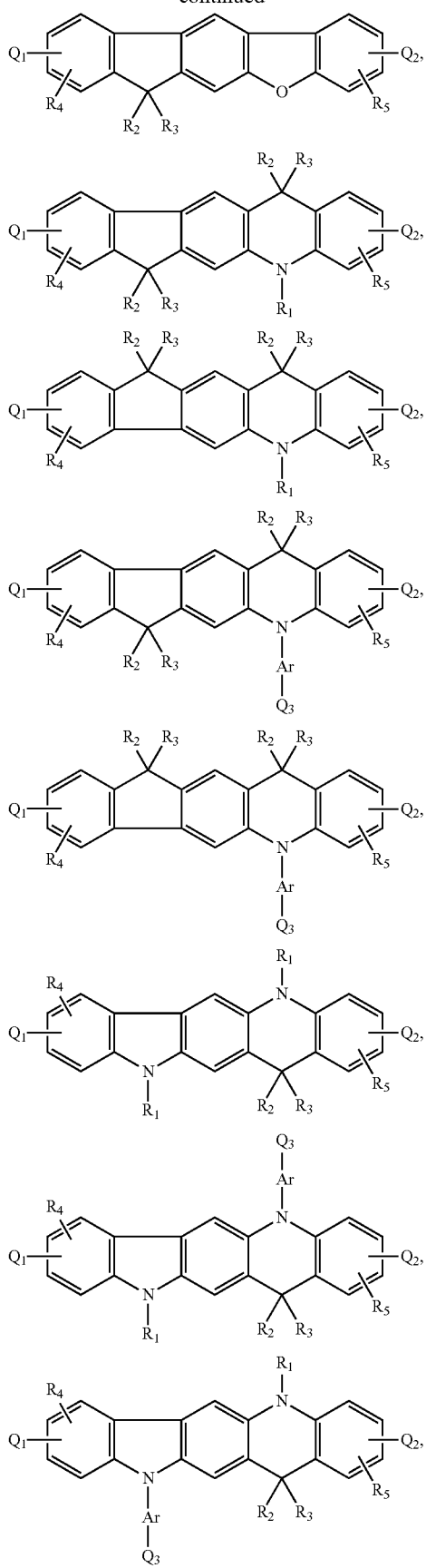
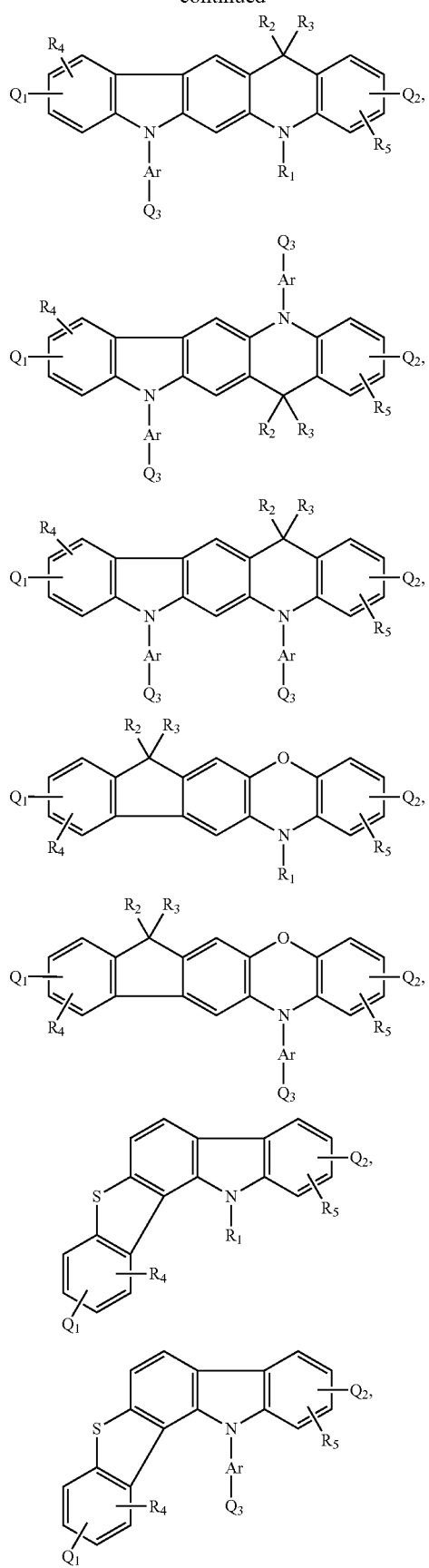

-continued

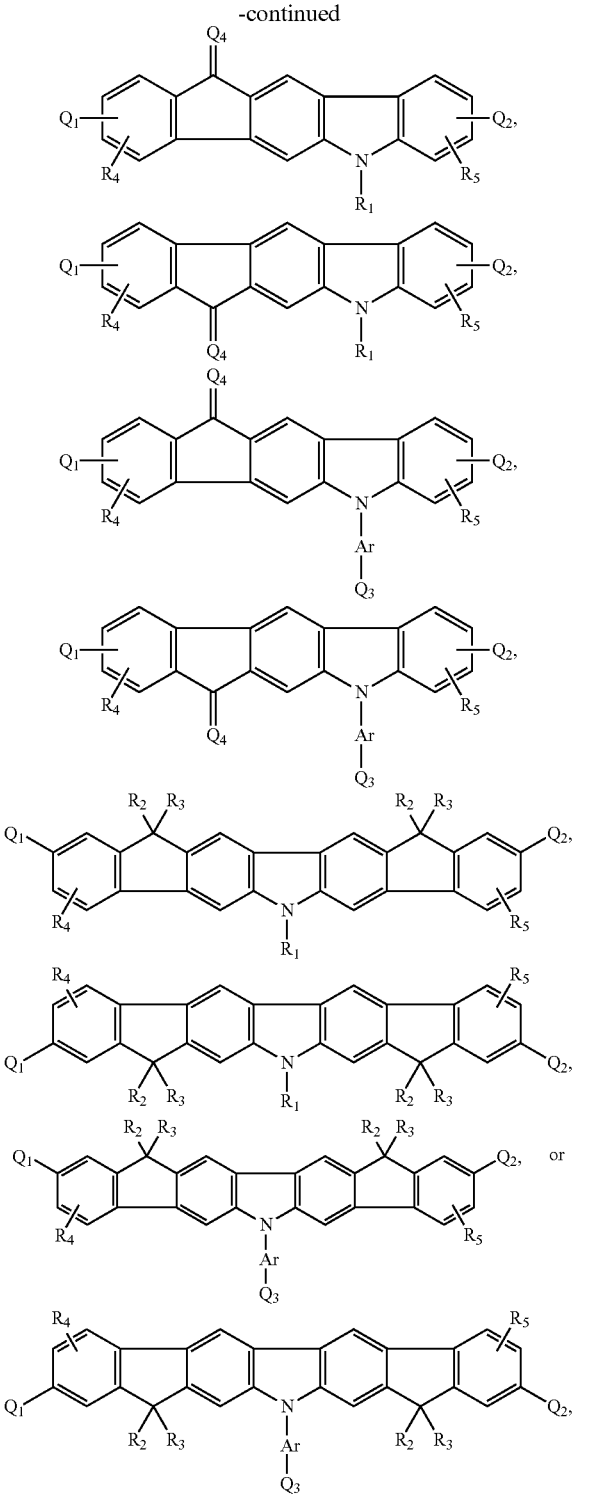

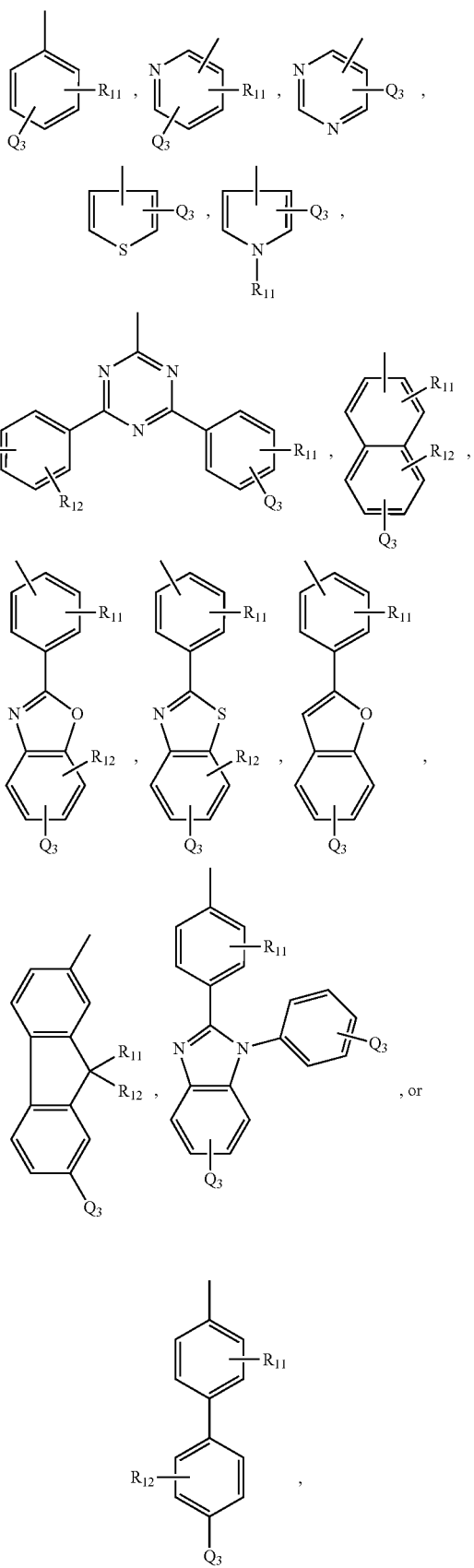

wherein $Q_1$, $Q_2$, $Q_3$, $Q_4$, $R_1$, $R_2$, $R_3$, $R_4$, $R_5$, and Ar are as defined above.

In embodiments, —Ar— (i.e. a linker -LK-) is optionally substituted arylene as defined above with respect to -LK-. It should be noted that although the formulas above and below show only one $Q_3$ attached to —Ar—, there may be more than one such $Q_3$. In embodiments, each —Ar-$Q_3$ independently represents wherein $R_{11}$ and $R_{12}$ are optional and independently represent one or more:
$C_1$-$C_{12}$ alkyl optionally substituted with one or more:
—$NR_8R_9$,
—O-L,
—S-L, and/or
phenyl optionally substituted with one or more: $C_1$-$C_6$ alkyl, halogen, nitrile, alkyloxy, $COOR_{10}$, and/or $C_2$-$C_{12}$ alkylcarboxyl;
$C_4$-$C_{10}$ cycloalkyl, $C_2$-$C_{12}$ alkenyl, $C_4$-$C_{10}$ cycloalkenyl, $C_2$-$C_{12}$ alkynyl, and/or $C_4$-$C_{10}$ cycloalkynyl, each of which being optionally substituted by alkyl and/or —O-L; and/or
phenyl, biphenyl and naphthyl, each of which being optionally substituted with one or more:
$C_1$-$C_6$ alkyl,
halogen,
nitrile,
alkyloxy,
—$COOR_{10}$, and/or
$C_2$-$C_{12}$ alkylcarboxyl.
wherein L, $R_8$, $R_9$ and $R_{10}$ are as defined above.

With regard to the above formulas for Ar, it should also be noted that in other embodiments, the $Q_3$ group(s) may be attached at positions of the Ar group different from that shown above.

In embodiments, the compound is:

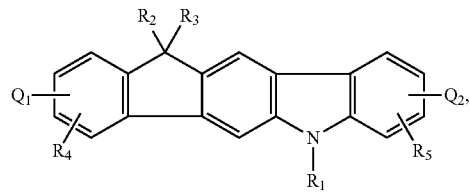

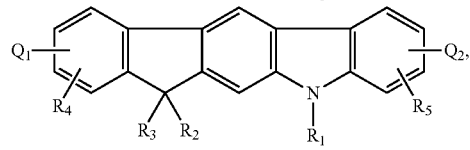

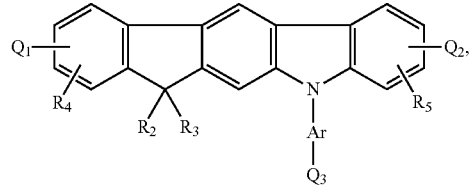

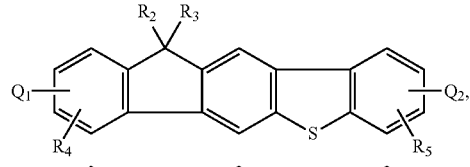

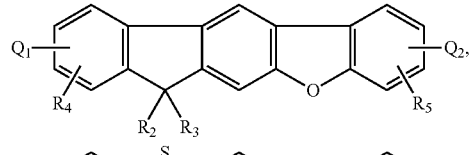

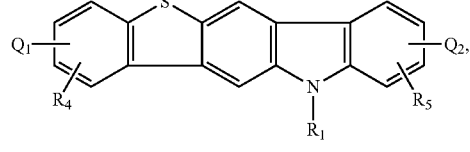

-continued

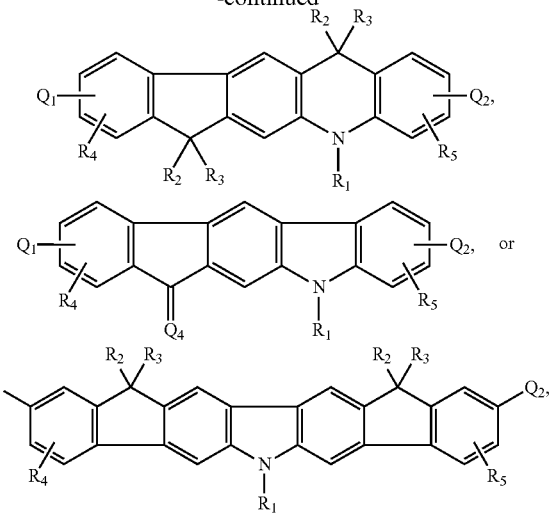

wherein:
$R_4$ and $R_5$ are optional and independently represent one $C_1$-$C_{12}$ alkyl or $C_1$-$C_{12}$ alkyloxy,
$Q_1$ and $Q_2$ are optional and independently represent one acyl group or one oxime ester group of formula

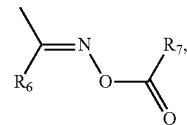

$R_1$, $R_2$, and $R_3$ each independently represent a hydrogen atom or $C_1$-$C_{12}$ alkyl,
$Q_3$ represents a hydrogen atom, an acyl group, or an oxime ester group of formula:

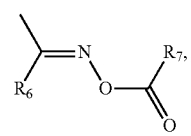

$Q_4$ represents acyl or an oxime ester of formula:

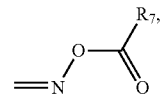

Ar represents

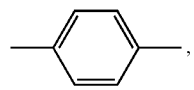

and
$R_6$ and $R_7$ independently represents alkyl,
with the proviso that the compound comprise at least one acyl or oxime ester group.

In embodiments of the above, the compound comprises at least oxime ester group, but no acyl group.
In embodiments, the compound is:
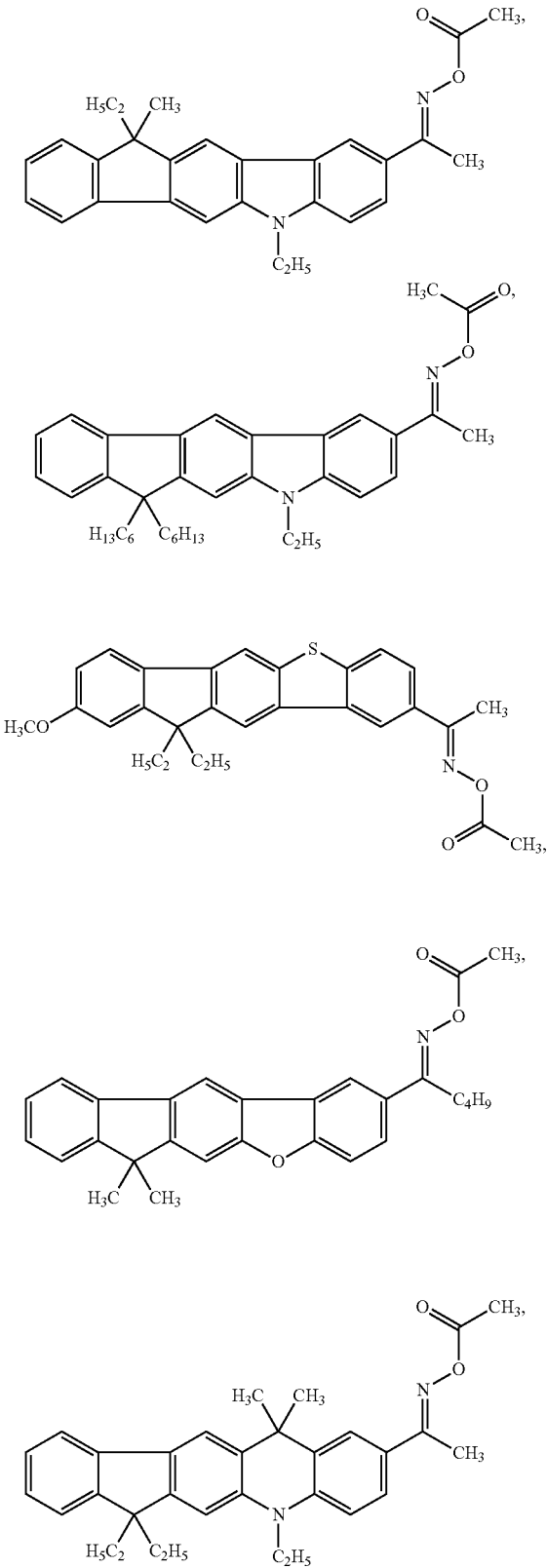
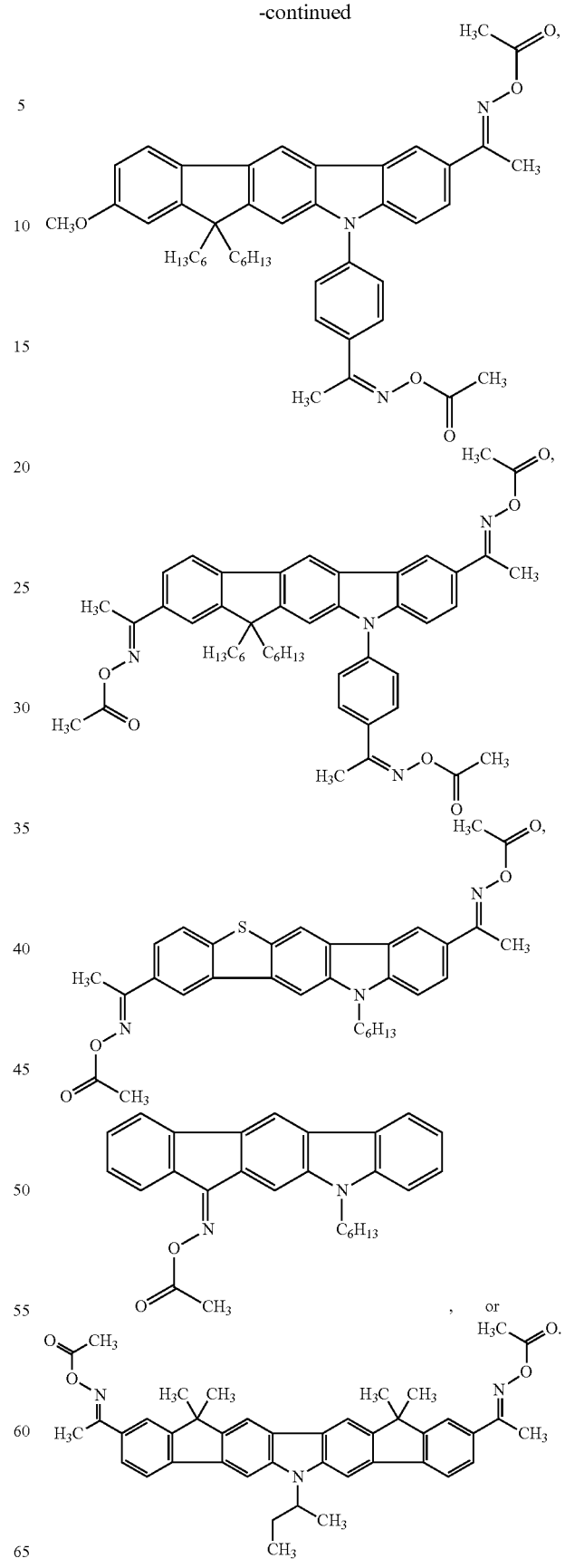

Specific embodiments in which one FORMULA I is fused with two FORMULA II to form truxene, truxenone, triazatruxene, or derivatives thereof will now be discussed. For simplicity, the following numbering will be used when discussing the general structure of these compounds:

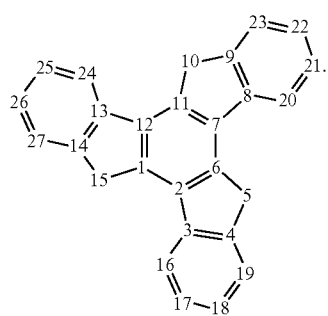

It is to be noted however that numbering according the standard rules of chemical nomenclature will be used when naming specific compounds (for example, in the "Description of Illustrative Embodiments" section below).

Also, the various rings in the compound of the invention will be referred as follows: the central phenyl ring (i.e. the phenyl ring comprising carbon atoms no. 1-2, 6-7, and 11-12), the three intermediate five-membered rings (i.e. the five-membered rings made of carbon atoms no. 2-6, carbon atoms no. 7-11, and carbon atoms no. 1, and 12-15, respectively), and the three outer phenyl rings (i.e. the phenyl rings made of carbon atoms no. 3-4 and 16-19, of carbon atoms no. 8-9 and 20-23, and of carbon atoms no. 13-14 and 24-27, respectively).

In embodiments, the truxene, triazatruxene, truxenone or derivative thereof has attached thereto, directly or indirectly, one, two, three, four, five or six oxime ester groups or one, two, three, four, five or six acyl groups. In embodiments, they comprise one, two, three, four, five oxime ester groups or more and/or six, five, four, three, two oxime ester groups or less. In embodiments, they comprise one, two, three, four, five acyl groups or more and/or six, five, four, three, two acyl groups or less.

In embodiments, some or all of the oxime ester or acyl groups are directly or indirectly attached to the outer phenyl rings of the truxene, truxenone, triazatruxene or derivative thereof. In other words, some or all of the oxime ester or acyl groups are directly or indirectly attached to carbon atoms no. 16-19, 20-23, and 24-27.

In the same or different embodiments, some or all of the oxime ester or acyl groups are directly or indirectly attached to the intermediate five-membered rings of the truxene, triazatruxene or derivative thereof. In other words, some or all of the oxime ester or acyl groups are directly or indirectly attached to carbon or nitrogen atoms no. 5, 10, and 15.

In embodiments, the compound comprises:

truxene:

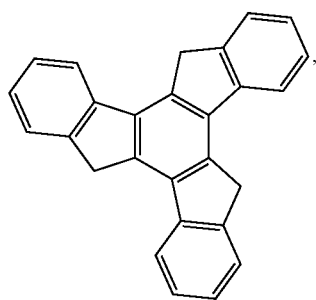

truxenone:

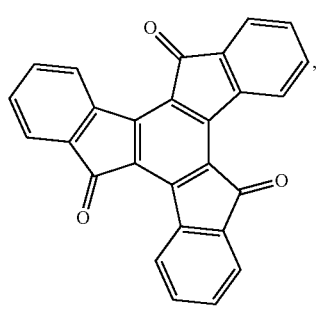

triazatruxene:

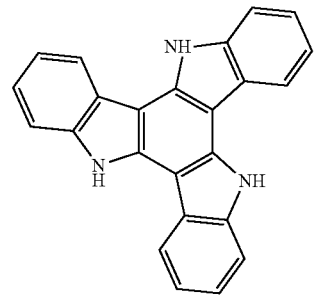

or a derivative thereof, the truxene, truxenone, triazatruxene or derivative thereof having attached thereto, at least one of -$E_1$, -LK-$E_1$, or =$E_2$, wherein -LK- is as defined above, -$E_1$ is —$CR_6$=N—O—(C=O)—$R_7$ or —C(=O)—$R_{30}$, and =$E_2$ is =N—O—(C=O)—$R_7$, wherein $R_5$, $R_7$, and $R_{30}$ are as defined above.

In embodiments, the compound is of formula:

Formula 1

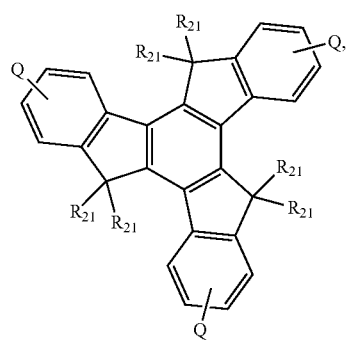

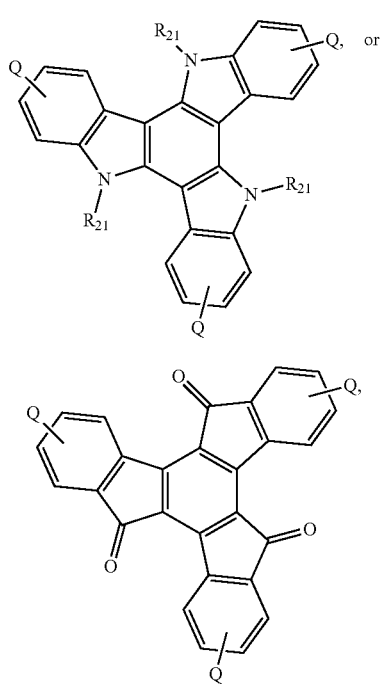

Formula 2

Formula 3 wherein:

each Q independently represents 1 to 4:
- hydrogen;
- $-E_1$;
- $-LK-E_1$;
- $-LK-(E_1)_2$;
- $C_1-C_{12}$ alkyl optionally substituted with one or more $-NR_{19}R_{20}$, $-O-L$ and/or $-S-L$;
- $C_1-C_{12}$ haloalkyl;
- $C_4-C_8$ cycloalkenyl;
- $C_2-C_{12}$ alkynyl;
- phenyl or $-N(R_{19})$-phenyl, each of which being optionally substituted with one or more $C_1-C_6$ alkyl, halogen, nitrile, alkyloxy, $-COOR_{19}$, and/or $C_2-C_{12}$ alkylcarboxyl;
- benzoyl, naphthoyl, phenyloxycarbonyl, or naphtyloxycarbonyl, each of which being optionally substituted by one or more $C_1-C_{20}$ alkyl, $C_1-C_4$ haloalkyl, $-SR_{19}$, $-OR_{19}$, $-NR_{19}R_{20}$, halogen, phenyl, $-COOR_{19}$, $-CONR_{19}R_{20}$, $-CN$, $-NO_2$ and/or $C_3-C_{10}$ cycloalkyl, wherein the $C_3-C_{10}$ cycloalkyl may be interrupted by $-O-$, $-(C=O)-$ or $-N(R_{19})-$;
- $-NR_{16}R_{17}$; and/or
- thiophene carbonyl or pyrrolidinyl, each of which being optionally substituted with one or more $C_1-C_6$ alkyl, halogen, nitrile, alkyloxy, $-COOR_{19}$, and/or $C_2-C_{12}$ alkylcarboxyl, and each $R_{21}$ independently represents:
- hydrogen;
- $-E_1$;
- $-LK-E_1$;
- $-LK-(E_1)_2$;
- $C_1-C_{12}$ alkyl optionally substituted with one or more phenyl, $-NR_{19}R_{20}$, $-O-L$ and/or $-S-L$;
- $C_4-C_8$ cycloalkenyl;
- $C_2-C_{12}$ alkynyl; or
- phenyl optionally substituted with one or more $C_1-C_6$ alkyl, nitrile, alkyloxy, $-COOR_{16}$, and/or $C_2-C_{12}$ alkylcarboxyl, and/or two $R_{21}$ attached to the same carbon atom represent $=O$ or $=E_2$, wherein:

$R_{16}$ and $R_{17}$ independently represent:
- hydrogen,
- $C_1-C_{12}$ alkyl optionally substituted with one or more $-NR_{19}R_{20}$, $-O-L$ and/or $-S-L$;
- $C_4-C_{10}$ cycloalkyl;
- $C_4-C_{10}$ cycloalkenyl;
- $C_2-C_{12}$ alkynyl;
- $C_1-C_{12}$ haloalkyl; or
- phenyl or benzoyl, each of which optionally substituted with one or more $C_1-C_6$ alkyl, halogen, nitrile, alkyloxy, $-COOR_{19}$, and/or $C_2-C_{12}$ alkylcarboxyl group, $R_{19}$ and $R_{20}$ independently represent hydrogen, $C_1-C_{12}$ alkyl; $C_1-C_{12}$ haloalkyl; $C_4-C_8$ cycloalkenyl; or $C_2-C_{12}$ alkynyl, L, -LK-, $-E_1$, $=E_2$, $-R_4$ and $-R_5$ are as defined above, provided that the compound comprises at least one oxime ester or acyl group, and provided that when $R_{21}$ is attached to a nitrogen atom and $R_{21}$ is $-E_1$, $-E_1$ is not $-CR_6=N-O-(C=O)-R_7$.

Herein, "each $R_{21}$ independently represents [list of substituents] and/or two $R_{21}$ attached to the same carbon atom represent $=O$ or $=E_2$" means that some or all the $R_{21}$ groups may represent the substituents listed while some or all the pairs of $R_{21}$ attached to a common carbon atom can be $=O$ or $=E_2$.

Also, "each Q independently represent 1 to 4 [list of substituents]" means that each Q may represent 1, 2, 3 or 4 substituents, each independently selected from the list. Also, it means that the substituents for each Q are selected independently from those selected for the other Q groups.

In embodiments, when each Q represents one substituent, these substituents are attached to carbon atoms no. 17 or 18, carbon atoms no. 21 or 22, and carbon atoms no. 25 or 26, respectively.

In embodiments, the compound is of formula:

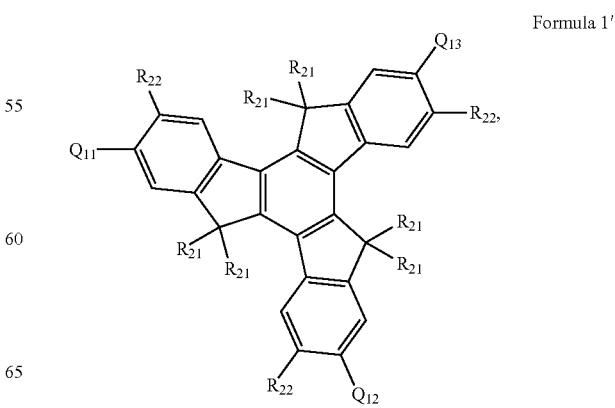

Formula 1'

-continued

Formula 2'

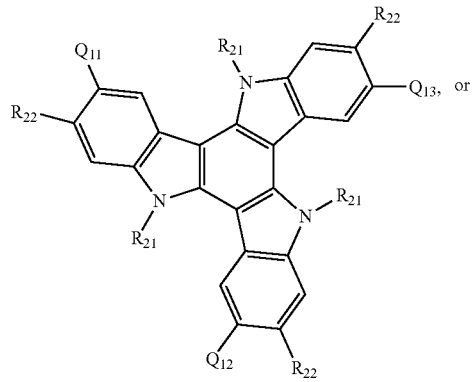

Formula 3'

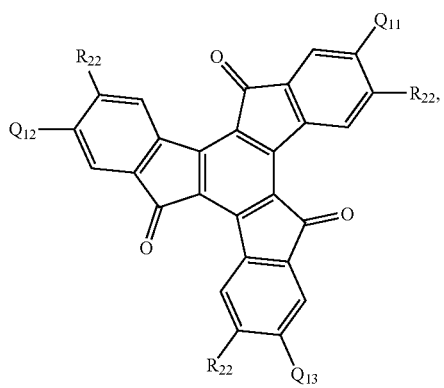

wherein
each of $Q_{11}$, $Q_{12}$ and $Q_{13}$ independently represents:
  hydrogen;
  -$E_1$;
  -LK-$E_1$;
  -LK-$(E_1)_2$;
  $C_1$-$C_{12}$ alkyl optionally substituted with one or more —$NR_{19}R_{20}$, —O-L and/or —S-L;
  $C_1$-$C_{12}$ haloalkyl;
  $C_4$-$C_8$ cycloalkenyl;
  $C_2$-$C_{12}$ alkynyl;
  phenyl or —N($R_{19}$)-phenyl, each of which being optionally substituted with one or more $C_1$-$C_6$ alkyl, halogen, nitrile, alkyloxy, —COOR$_{19}$, and/or $C_2$-$C_{12}$ alkylcarboxyl;
  benzoyl, naphthoyl, phenyloxycarbonyl, or naphtyloxycarbonyl, each of which being optionally substituted by one or more $C_1$-$C_{20}$ alkyl, $C_1$-$C_4$ haloalkyl, —SR$_{19}$, —OR$_{19}$, —NR$_{19}$R$_{20}$, halogen, phenyl, —COOR$_{19}$, —CONR$_{19}$R$_{20}$, —CN, —NO$_2$ and/or $C_3$-$C_{10}$ cycloalkyl, wherein the $C_3$-$C_{10}$ cycloalkyl may be interrupted by —O—, —(C=O)— or —N(R$_{19}$)—;
  —NR$_{16}$R$_{17}$; and/or
  thiophene carbonyl or pyrrolidinyl, each of which being optionally substituted with one or more $C_1$-$C_6$ alkyl, halogen, nitrile, alkyloxy, —COOR$_{19}$, and/or $C_2$-$C_{12}$ alkylcarboxyl,
each $R_{22}$ independently represents:
  hydrogen;
  $C_1$-$C_{12}$ alkyl optionally substituted with one or more —$NR_{19}R_{20}$, —O-L and/or —S-L;
  $C_1$-$C_{12}$ haloalkyl;
  $C_4$-$C_8$ cycloalkenyl;
  $C_2$-$C_{12}$ alkynyl;
  phenyl or —N($R_{19}$)-phenyl, each of which being optionally substituted with one or more $C_1$-$C_6$ alkyl, halogen, nitrile, alkyloxy, —COOR$_{19}$, and/or $C_2$-$C_{12}$ alkylcarboxyl; or
  benzoyl, naphthoyl, phenyloxycarbonyl, or naphtyloxycarbonyl, each of which being optionally substituted by one or more $C_1$-$C_{20}$ alkyl, $C_1$-$C_4$ haloalkyl, —SR$_{19}$, —OR$_{19}$, —NR$_{19}$R$_{20}$, halogen, phenyl, —COOR$_{19}$, —CONR$_{19}$R$_{20}$, —CN, —NO$_2$ and/or $C_3$-$C_{10}$ cycloalkyl, wherein the $C_3$-$C_{10}$ cycloalkyl is interrupted by —O—, —(C=O)— or —N(R$_{19}$)—,
wherein $R_{16}$, $R_{17}$, $R_{19}$, $R_{20}$, $R_{21}$, L, -LK-, -$E_1$, =$E_2$, —$R_4$ and —$R_5$ are as defined above,
provided that the compound comprises at least one oxime ester or acyl group, and provided that when $R_{21}$ is attached to a nitrogen atom and $R_{21}$ is -$E_1$, -$E_1$ is not —CR$_6$=N—O—(C=O)—R$_7$.

In more specific embodiments of the above compounds, -LK-$E_1$ represents:

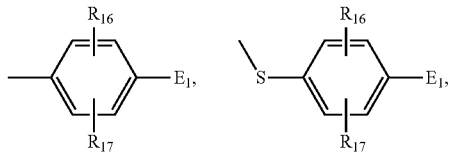

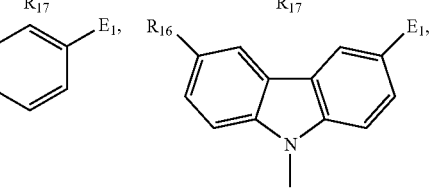

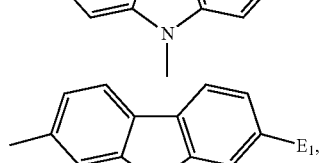

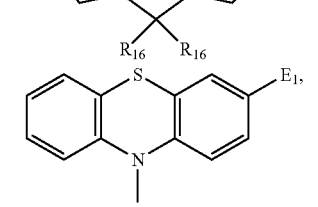

and -LK-$(E_1)_2$ represents:

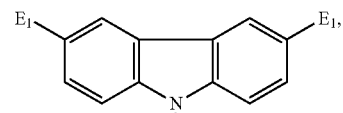

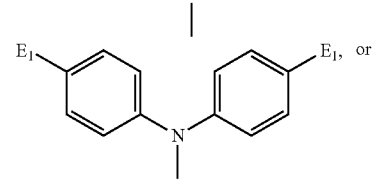

-continued

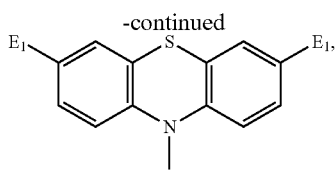

wherein $R_{16}$ and $R_{17}$ are as defined above and wherein $R_{18}$ is hydrogen or $C_1$-$C_{12}$ alkyl optionally substituted with one or more —O-L and/or —S-L, L being as defined above.

It should also be noted that in other embodiments, the $E_1$ group(s) may be attached at other positions of the linkers shown above.

For more certainty, above two $R_{21}$ attached to the same carbon atom represent =O or =$E_2$" means, for example, than Formula 1 above would represents compounds of the formula:

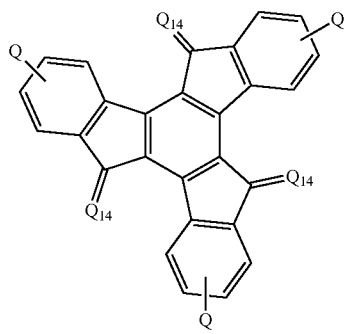

wherein =$Q_{14}$ is =O or =$E_2$. It should be noted that among formulas 1, 1', 2, 2', 3 and 3' above, only formulas 1 and 1' have pairs of $R_{21}$ groups attached to a common carbon atom that can become $Q_4$.

In other embodiments of the above formulas 1, 1', 2, 2', 3 and 3', the compound comprises one or more oxime ester group, but no acyl groups.

In other embodiments of the above formulas 1, 1', 2, 2', 3 and 3', the compound comprises one or more, acyl groups, but not oxime ester group.

In embodiments of the above formulas 1, 1', 2, 2', 3 and 3':
  each Q, $Q_1$, $Q_2$, and $Q_3$, when present, represents one -$E_1$ of formula —$CR_6$=N—O—(C=O)—$R_7$, wherein $R_6$ represents $C_1$-$C_{12}$ alkyl optionally substituted with —O-L, wherein L is $C_1$-$C_6$ alkyl, and $R_7$ represents $C_1$-$C_{12}$ alkyl;

all $R_{22}$, when present, represent hydrogen; and
all $R_{21}$, when present, represent hydrogen or $C_1$-$C_{12}$ alkyl.

In other embodiments of the above formulas 1, 1', 2, 2', 3 and 3':
  each Q, $Q_{11}$, $Q_{12}$, and $Q_{13}$, when present, represents one -LK-$E_1$, wherein $E_1$ is of formula —$CR_6$=N—O—(C=O)—$R_7$, wherein $R_6$ represents $C_1$-$C_{12}$ alkyl optionally substituted with —O-L, wherein L is $C_1$-$C_6$ alkyl, and $R_7$ represents $C_1$-$C_{12}$ alkyl;
  all $R_{22}$, when present, represent hydrogen;
  all $R_{21}$, when present, represent hydrogen or $C_1$-$C_{12}$ alkyl; and
  LK represents

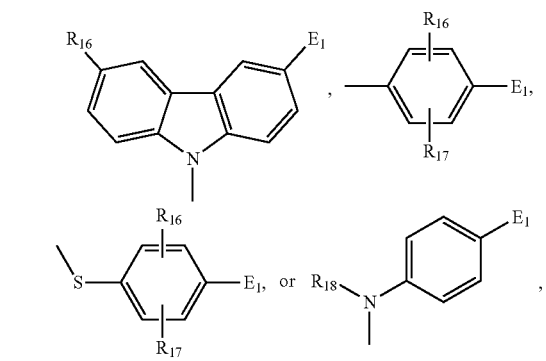

wherein $R_{16}$ is hydrogen or benzoyl substituted with $C_1$-$C_6$ alkyl, $R_{17}$ represents hydrogen and $R_{16}$ represents $C_1$-$C_{12}$ alkyl.

In other embodiments of the above formulas 1 and 1', each of $Q_{11}$, $Q_{12}$, and $Q_{13}$, when present, represents hydrogen, each of Q and $R_{22}$, when present, represents one —N($R_{19}$)-phenyl wherein $R_{19}$ represents $C_1$-$C_{12}$ alkyl, and every pair of $R_{21}$ attached to a common carbon atom represent =$E_2$ wherein $R_7$ represents $C_1$-$C_{12}$ alkyl.

In embodiments of the above formulas 1, 1', 2, 2', 3 and 3':
  each Q, $Q_1$, $Q_2$, and $Q_3$, when present, represents one -LK-$E_1$ or -$E_1$, wherein $E_1$ is of formula —C(=O)—$R_{30}$, wherein $R_{30}$ represents $C_1$-$C_{12}$ linear alkyl, phenyl, phenyl substituted with alkyl or alkyloxy, or thiophenyl;
  all $R_{22}$, when present, represent hydrogen;
  all $R_{21}$, when present, represent $C_1$-$C_{12}$ alkyl, and
  LK represents 2-phenylene or 4-phenylene.

In embodiments, the compound is of formula:

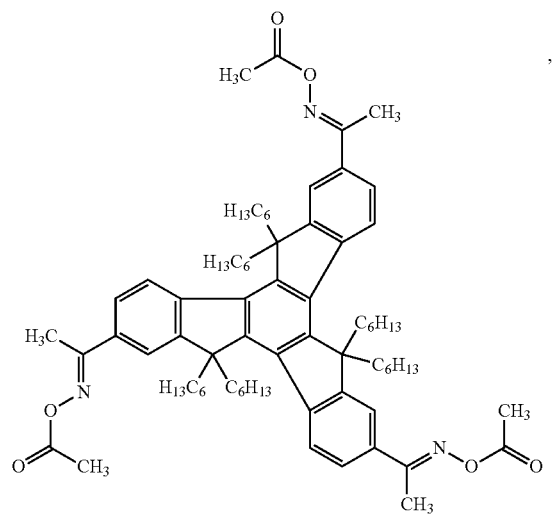

,

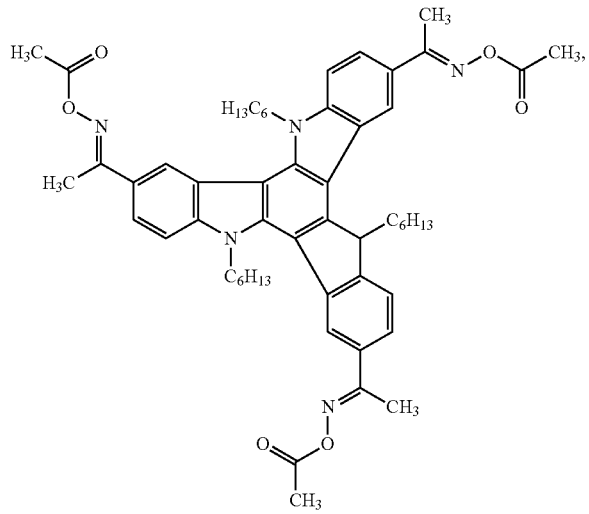

77
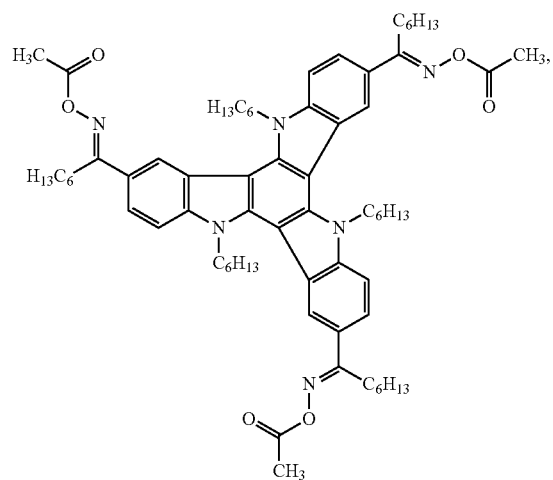
78
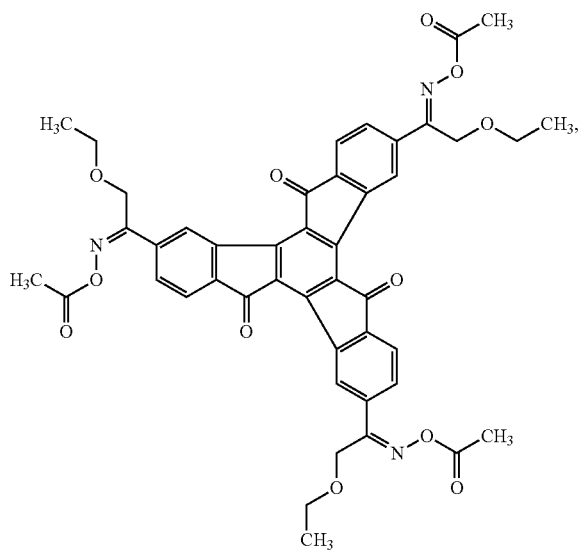
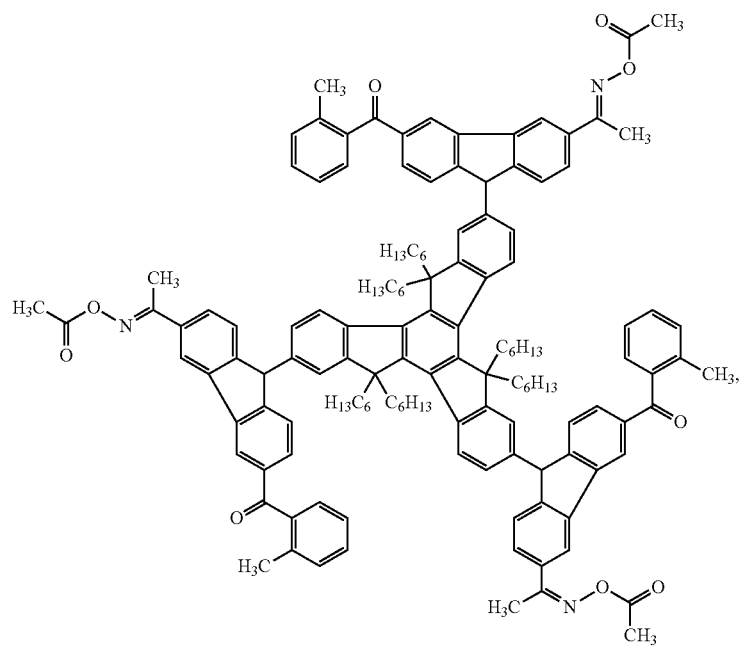

-continued
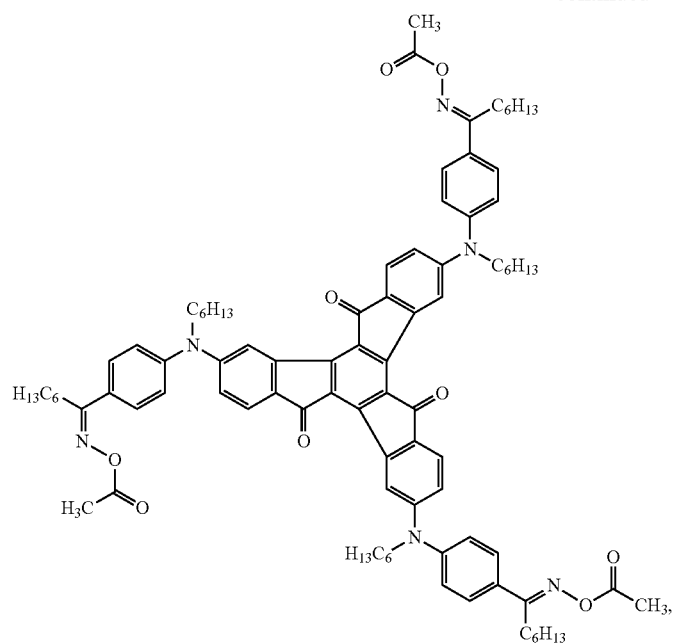
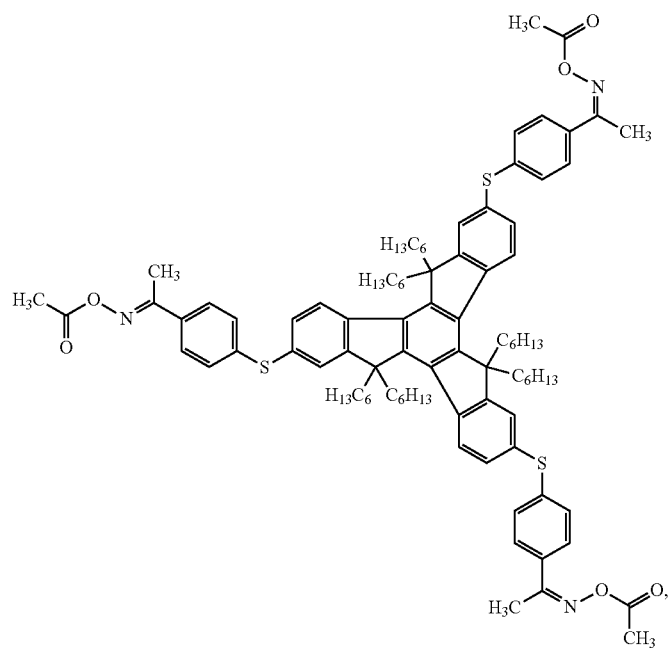

-continued
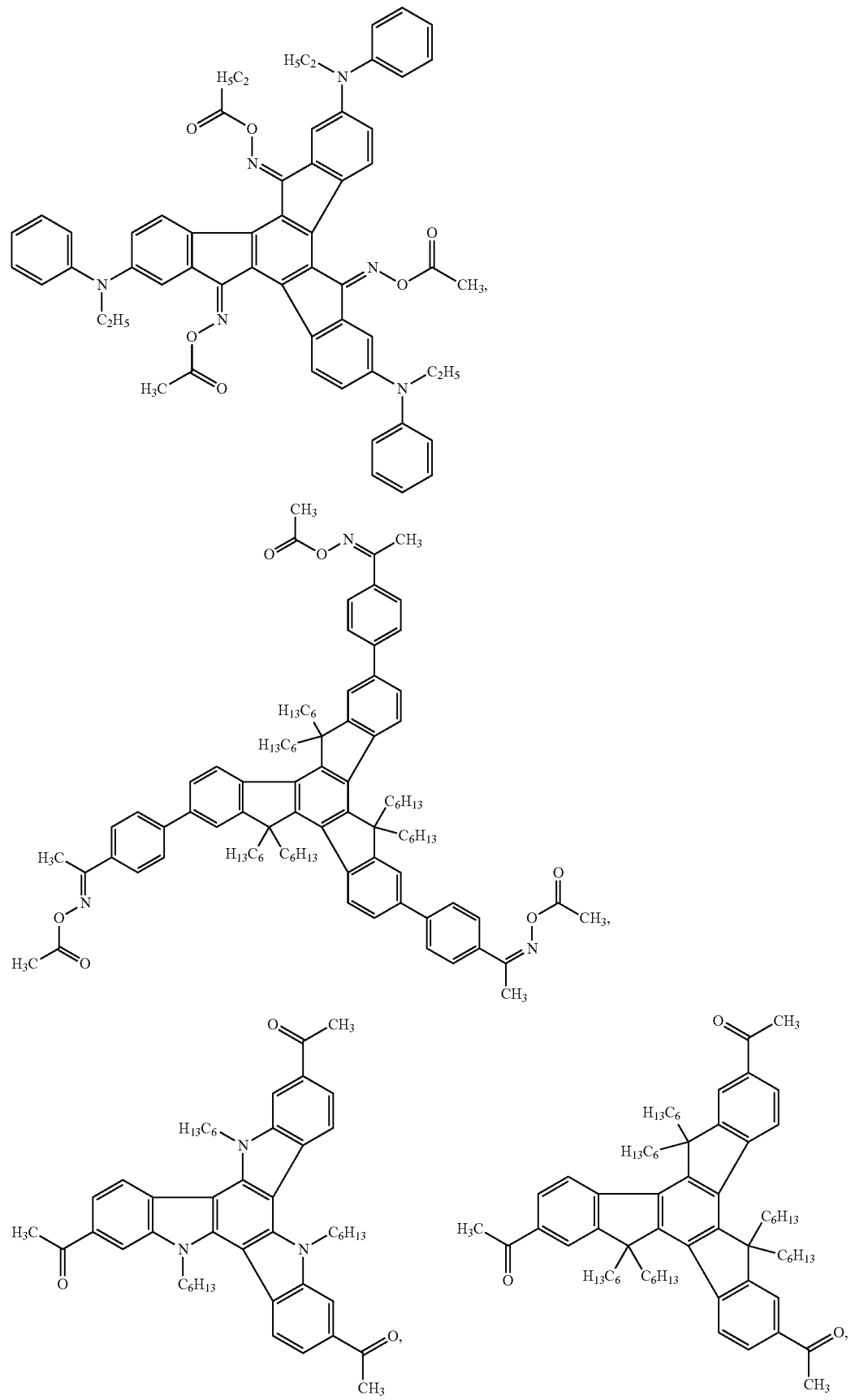

-continued
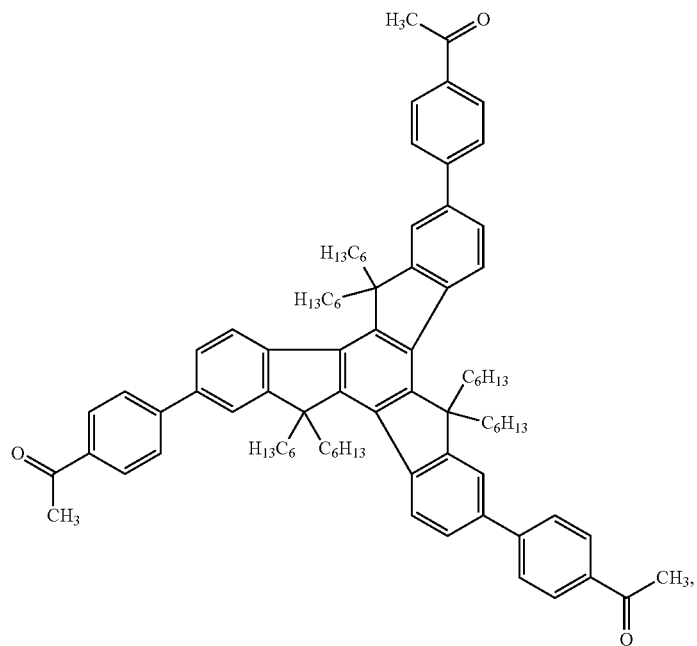
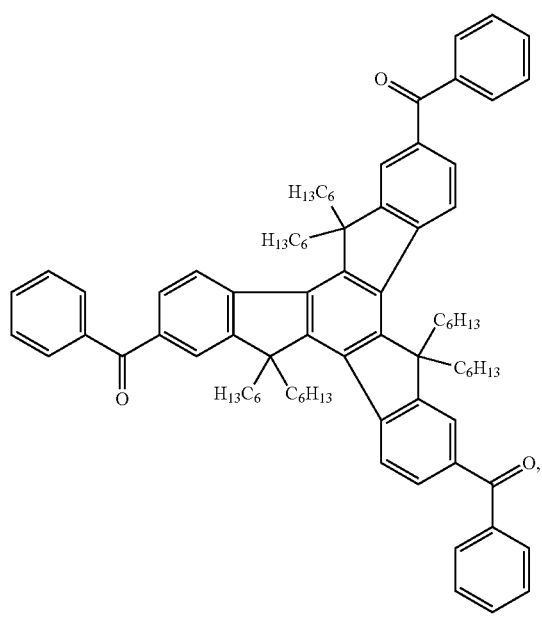

-continued
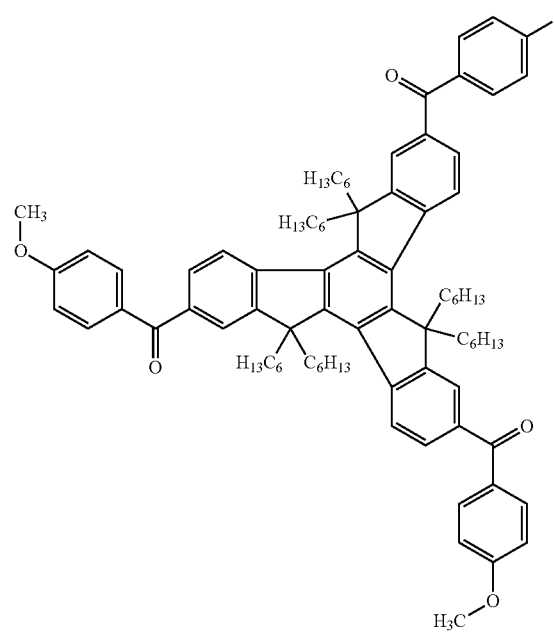
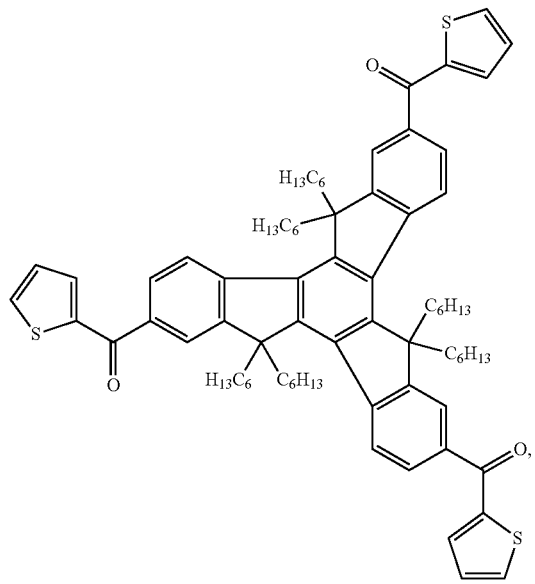
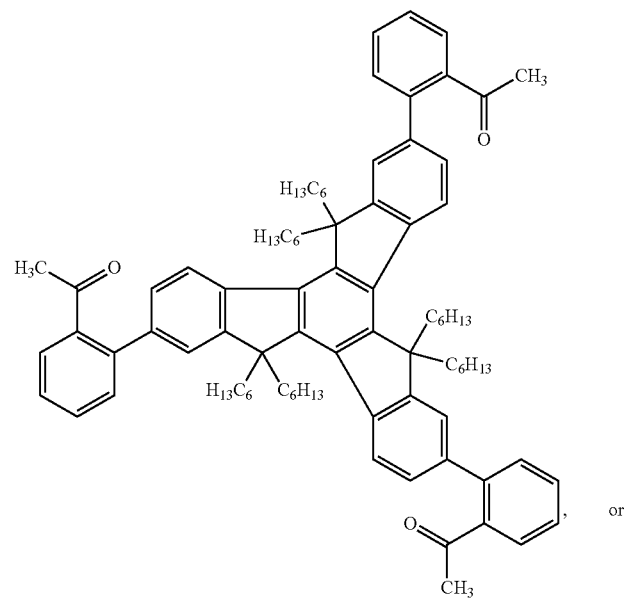, or

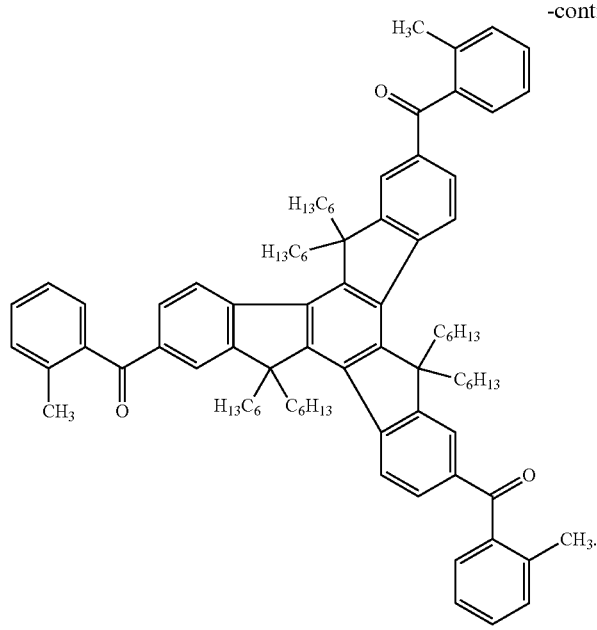

-continued

Uses of the Compounds of the Invention

The compounds of the invention are useful as photoinitiators. They absorb UV light and then emit free radicals. As such, they are useful in photosensitive or photopolymerizable compositions. Such compositions typically comprise, in addition to the compound of the invention, a free radical polymerizable compound. Such free radical polymerizable compound will typically be an ethylenic unsaturated bond-containing polymerizable compound. These compositions also often comprise other components, which are known to the skilled person who will select them depending on the intended use of the polymerizable composition.

Photosensitive or photopolymerizable compositions and polymerizable compounds for use therein are well known to the skilled person. Non-limiting examples of such compositions include photosetting or photocuring inks (including inks for inkjet printing (for example UV curable inkjet ink), gravure, and flexo printing), photosensitive printing plates, color filter resists, black matrix resin, lithographic printing plates, and a variety of photoresists, including dry film resists. The compounds of the invention are also useful as photoinitiators in compositions for oxygen scavenging films.

The compounds of the invention can replace photoinitiators used in photosensitive or photopolymerizable compositions of the prior art.

In particular, the compounds of the invention can be used in color filter resists such as those described in Kura et al., "New Oxime Ester Photoinitiators for Color Filter Resists", Radtech Report, May/June 2004, p 30-35.

They can also be used in the photopolymerizable compositions described at pages 7-61 of WO 2006/018405 and at pages 22-65 of WO 02/100903. They can also be used in the composition described in U.S. Pat. No. 6,949,678.

It is noted, for example, that such photopolymerizable compositions, in addition to the compound of the invention and a polymerizable compound, can include further known photoinitiators and other additives such as thermal inhibitors, copper compounds, wax-like substances, an oxygen-impermeable layer, light stabilizers, amines to accelerate photopolymerization, chain transfer agents, photosensitizers, cross-linking agents, co-initiators, photoreducable dyes, flow improvers, adhesion promoters, surfactants, optical brighteners, pigments, dyes, wetting agent, leveling assistants, dispersants, aggregation preventers, antioxidants, fillers, microspheres, glass fibers, binders, etc.

The photopolymerizable compositions can be used for various purposes, for example as printing ink, e.g. screen printing inks, inkjet printing inks, inks for offset- or flexo printing, as a clear finish, as a white or colored finish, for example for wood or metal, as powder coating, as a coating material, inter alias for paper, wood, metal or plastic, as a daylight-curable coating for the marking of buildings and roadmarking, for photographic reproduction techniques, for holographic recording materials, for image recording techniques or to produce printing plates which can be developed with organic solvents or with aqueous alkalis, for producing masks for screen printing, as dental filling compositions, as adhesives, as pressure-sensitive adhesives, as laminating resins, as etch resists, solder resists, electroplating resists, or permanent resists, both liquid and dry films, as photostructurable dielectric, for printed circuit boards and electronic circuits, as resists to manufacture color filters for a variety of display applications or to generate structures in the manufacturing process of plasma-display panels and electroluminescence displays, (as for example described in U.S. Pat. No. 5,853,446; EP 863,534; JP 09-244230-A; JP 10-62980-A; JP 08-171863-A; U.S. Pat. No. 5,840,465; EP 855,731; JP 05-271576-A; and JP 05-67405-A) for the production of holographic data storage (HDS) material, for the production of optical switches, optical lattices (interference lattice), light circuits, for producing three-dimensional articles by mass curing (UV curing in transparent moulds) or by the stereolithography technique, as is described, for example, in U.S. Pat. No. 4,575,330, to produce composite materials (for example styrenic polyesters, which may, if desired, contain glass fibers and/or other fibers and other auxiliaries) and other thick-layered compositions, for coating or sealing electronic components and integrated circuits, or as coatings for optical fibers, or for producing optical lenses, e.g. contact lenses or Fresnel lenses. The compositions according to the invention are further suitable for the production of medical equipment, auxiliaries or implants. Further, the compositions according to the invention are suitable for the preparation of gels with thermotropic properties, as for example described in DE 19700064 and EP 678,534.

The photoinitiators may additionally be employed as initiators for emulsion polymerizations, pearl polymerizations or suspension polymerizations, as polymerization initiators for fixing ordered states of liquid-crystalline monomers and oligomers, or as initiators for fixing dyes on organic materials. They can also be used for the polymerization of radiation-curable powder coatings. They further find application in negative resist compositions, suitable for the production of printing forms for relief printing, planographic printing, photogravure or of screen printing forms, for the production of relief copies, for example for the production of texts in Braille, for the production of stamps, for use in chemical milling or as a microresist in the production of integrated circuits. The compositions further may be used as photopatternable dielectric layer or coating, encapsulating material and isolating coating in the production of computer chips, printed boards and other electric or electronic components. The possible layer supports, and the processing conditions of the coating substrates, are just as varied.

These compositions can also be photosensitive thermosetting resin compositions that can be used to form a solder resist pattern. These can be useful as materials for the production of printed circuit boards, the precision fabrication of metallic articles, the etching of glass and stone articles, the relief of plastic articles, and the preparation of printing plates. The solder resist is a substance which is used during the soldering of a given part to a printed circuit board for the purpose of preventing molten solder from adhering to irrelevant portions and protecting circuits.

They are suitable for the production of color filters or color mosaic systems, such as described, for example, in EP 320, 264. Color filters usually are employed in the manufacturing of LCD's, projection systems and image sensors. The color filters can be used, for example, for display and image scanner in television receivers, video monitors or computers, in flat panel display technology etc.

The photosensitive compositions can further be used for manufacturing spacers, which control a cell gap of the liquid crystal part in liquid crystal display panels. The photosensitive compositions are also suitable for manufacturing microlens arrays used in liquid crystal display panels, image sensors and the like. These are also suitable for photolithographic steps used in the production process of plasma display panels (PDP), particularly for the imaging forming process of barrier rib, phosphor layer and electrodes. The compositions also find application for the production of one- or more-layered materials for the image recording or image reproduction (copies, reprography), which may be mono- or polychromatic. Furthermore the materials are suitable for color proofing systems. The compounds of the invention are also suitable as photoinitiators in the holographic data storage application. The photoinitiators are suitable for the preparation of optical articles (for example optical waveguides) or holographic recording media e.g. comprising a polymer and an organic photoinitiator. As already mentioned above, the photoinitiators are suitable also for producing printing plates. Also of interest is the use of the novel photoinitiators for curing shaped articles made from composite compositions. The compounds according to the invention can be used for the production of holographies, waveguides, optical switches wherein advantage is taken of the development of a difference in the index of refraction between irradiated and un-irradiated areas.

The compounds of the invention can also be used in the photosensitive resin compositions described in US 2010/0210749 and in the curable compositions, photopolymerizable compositions, color filters and the like described in US 2009/0023085, for example at paras [0130]-[0342] and at paras [0407]-[0607].

The compounds of the invention can also be used in the photosensitive compositions described in U.S. Pat. No. 7,556,910 and the photopolymerizable compositions of U.S. Pat. No. 6,051,367.

Thus, an aspect of the present invention is related to the use of the compounds as photoinitiators in color filter resist compositions. More specifically, the color filter resist compositions may, in embodiments, comprise:
from about 1 to about 5% by weight of the compound of the invention or a mixture thereof;
an alkaline soluble polymer;
a reactive oligomer;
a pigment; and
one or more optional additives.

Thus, another aspect of the present invention is related to the use of the invented compounds in the coating composition for production of lithographic offset printing plates, which can be digitally imaged with laser light having emission wavelength between 350 and 410 nm. More specifically, such coating compositions may, in embodiments, comprise:
from about 1 to about 5% by weight of the compound of the invention or a mixture thereof;
a polymeric binder resin;
a reactive oligomer;
one or more colorants; and
one or more optional film forming additives This coating composition can be coated on an anodized aluminum substrate having a coating weight between 0.8 and 3.0 gram per square meter.

In many embodiments, the compounds of the invention are relatively easy to make. For example, some of them are easily purified by crystallization, avoiding thus the need for flash chromatography. Also, many of them are soluble in one or more alcohols, which are relatively environmentally friendly solvents. In addition, many of them are colorless, which makes them useful in a wide range of application. Others are lightly colored and are more useful, for example, in black matrix resins and other applications where color is not an issue. Also, many compounds of the invention do not discolor upon use.

Herein, unless otherwise noted, "alkyl" refers to a univalent saturated linear or branched $C_{1-12}$ hydrocarbyl radical of formula $—C_nH_{2n+1}$. Similarly, "alkenyl" and "alkynyl" refer to linear or branched $C_{1-12}$ unsaturated (with double and triple bond(s), respectively) univalent hydrocarbyl radicals.

Herein, unless otherwise noted, "alkylene" refers to a bivalent saturated linear or branched $C_{1-12}$ hydrocarbyl radical of formula $—C_nH_{2n}—$. Similarly, "alkenylene" and "alkynylene" refer to linear or branched $C_{1-12}$ unsaturated (with double and triple bond(s), respectively) bivalent hydrocarbyl radicals.

Herein, unless otherwise noted, "aryl" and "arylene" refers respectively to univalent and bivalent aromatic radicals comprising between 1 and four aromatic rings. The rings can be fused or attached together through a covalent bond.

Herein, "about" has it ordinary meaning. In embodiments, it can mean plus or minus 5% of the numerical value it qualifies.

Herein, "comprising" is an open-ended term meaning "including, but not being limited to".

Other objects, advantages and features of the present invention will become more apparent upon reading of the following non-restrictive description of specific embodiments thereof, given by way of example only with reference to the accompanying drawings.

DESCRIPTION OF ILLUSTRATIVE EMBODIMENTS

Figure 1:
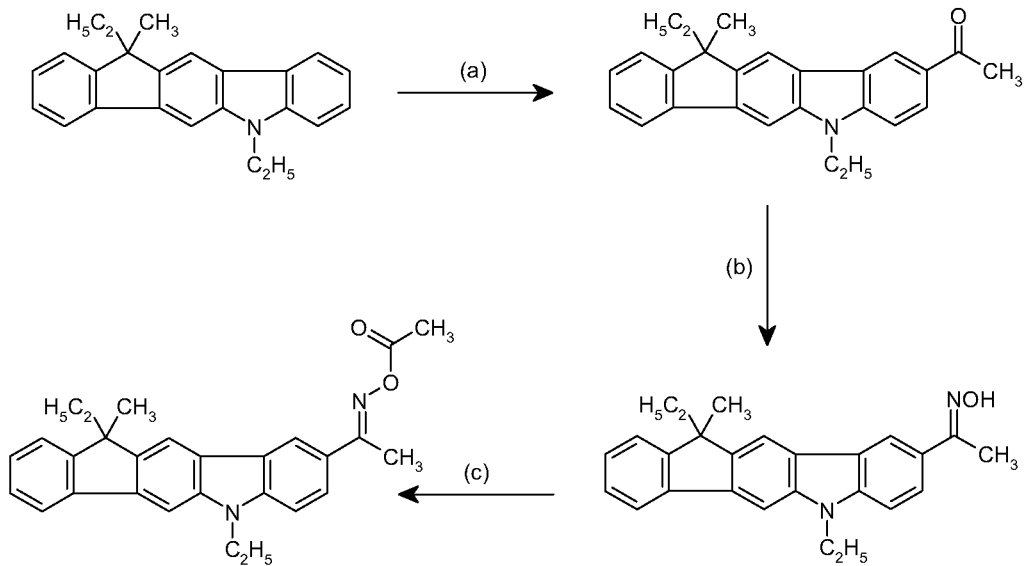
FIG. 1 shows the reaction scheme for the production of 3-acetyloxime-O-acetate-6,12-diethyl-12-methyl-6,12-dihydro-6-aza-indeno[1,2-b]fluorene.

The present invention is illustrated in further details by the following non-limiting examples.

GLOSSARY

The following have been used in the Examples below:

| Structure | Description |
|---|---|
| 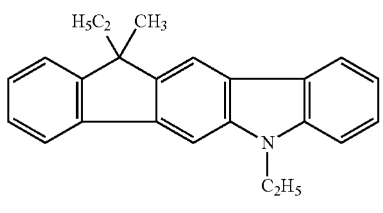 | 6,12-Diethyl-12-methyl-6,12-dihydro-6-aza-indeno[1,2-b]fluorene (99%); available from Mylan Group, Travinh City, Vietnam. |
| 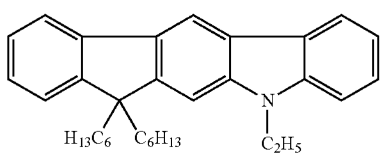 | 10-Ethyl-12,12-dihexyl-10,12-dihydro-10-aza-indeno[2,1-b]fluorene (99%); available from Mylan Group, Travinh City, Vietnam. |
| 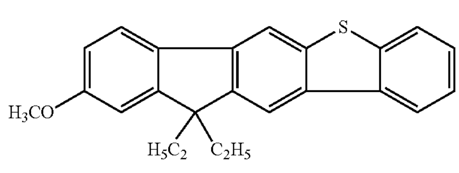 | 2-Methoxy-12,12-diethyl-6,12-dihydro-6-thia-indeno[1,2-b]fluorene (99%); available from Mylan Group, Travinh City, Vietnam. |
| 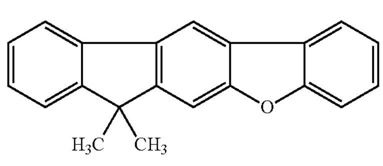 [SMILES: CC1(C)c2ccccc2-c2cc3c(cc21)oc1ccccc13] | 12,12-Dimethyl-10,12-dihydro-10-oxo-indeno[2,1-b]fluorene (98%); available from Mylan Group, Vietnam. |

| Structure | Description |
|---|---|
| 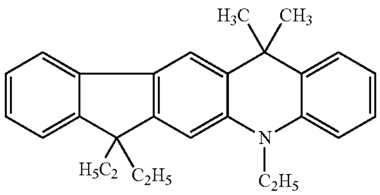 | 11,13,13-triethyl-6,6-dimethyl-11,13-dihydro-6H-11-aza-indeno[2,1-b]anthracene (98%); available from Mylan Group, Travinh City, Vietnam. |
| 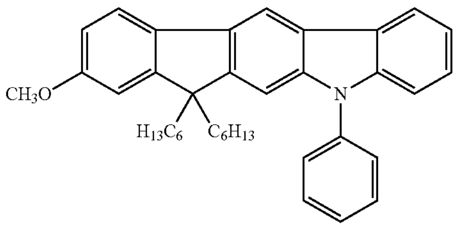 | 2-Methoxy-10-phenyl-12,12-dihexyl-10,12-dihydro-10-aza-indeno[2,1-b]fluorene (99%); available from Mylan Group, Travinh City, Vietnam. |
| 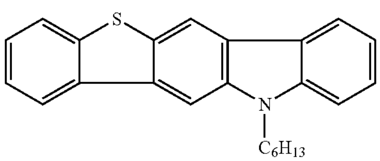 | 6-Hexyl-12-thia-6-aza-indeno[1,2-b]fluorene (99%); available from Mylan Group, Travinh City, Vietnam. |
| 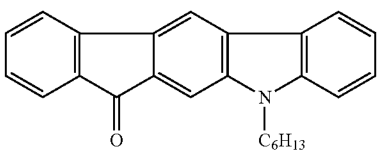 | 10-Hexyl-10H-10-aza-indeno[2,1-b]fluoren-12-one (99%); available from Mylan Group, Travinh City, Vietnam. |
| 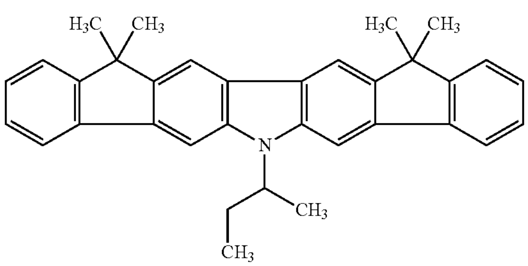 [SMILES: CCC(C)n1c2cc3c(cc2c2cc4c(cc21)-c1ccccc1C4(C)C)C(C)(C)c1ccccc1-3] | 1,1'-Dimethyl-bisindeno[3,2-b:2',3'-h]-9-sec-butyl carbazole (99%); available from Mylan Group, Travinh City, Vietnam. |

Basic green 4 (BG4): Colorant available from Spectra Colors, USA

BYK 307: Polyethylene glycol modified polysiloxane surfactant, available from BYK Chemie, USA TRUXE-6H: 5,5'',10,10'',15,15''-Hexahexyltruxene (98%), available from American Dye Source, Inc., Canada.

TRUXA-3H: 5,10,15-Trihexyl-10,15-dihydro-5H-5,10,15-triazadiindeno[1,2-a;1',2'-c]fluorene (98%), available from American Dye Source, Inc., Canada.

TRUXE-3Br: 2,7,12-Tribromo-5,5,10,10,15,15-hexahexyltruxene, available from American Dye Source, Inc., Canada.

TRUXE-3F: 4,9,14-Trifluoro truxenone (98%), available from American Dye Source, Inc., Canada TRUX-2Br: 2,2-Dibromo-5-fluoroindan-1-one (97%), available from American Dye Source, Inc., Canada Silane: γ-Methacryloxypropyl triethoxysilane, available from Sigma Aldrich, Canada BR07-001: Alkaline soluble polymeric binder resin (MW=37,000 g/mole) available from American Dye Source, Inc., Canada and having the following formula:

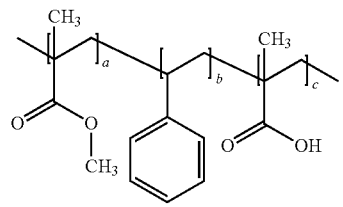

(a = 1.45, b = 0.25 and c = 0.30).

UR07-015: Reactive oligomer, available from American Dye Source, Inc., Canada and having the following formula:

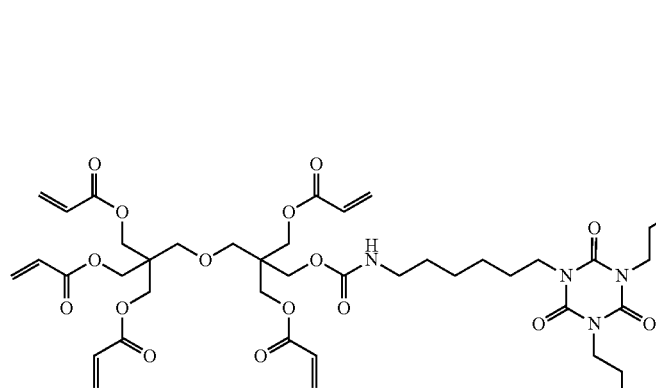
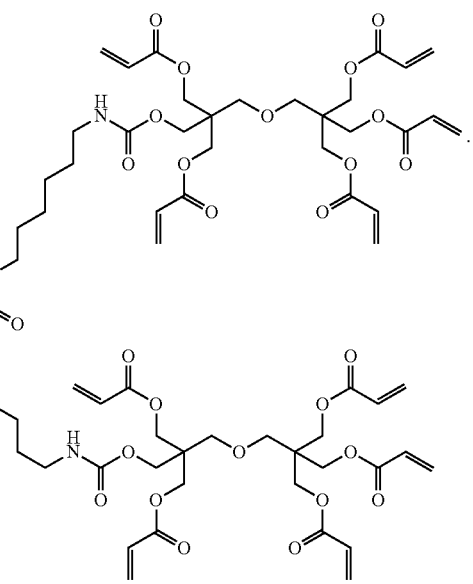

AC07-001: Acetal copolymer dispersant (MW=47,000 g/mole), available from American Dye Source, Inc., Canada and having the following formula:

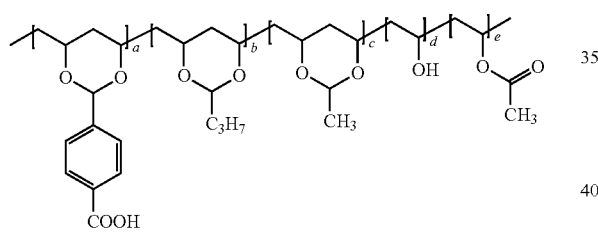

(a = 0.30, b = 0.50, c = 0.15, d = 0.03 and 0.02).

AC12-001: Acetal copolymer comprising cyclohexenyl pendant group (a=0.5, b=0.48 and c=0.02), available from Mylan Group, Travinh, Vietnam.

Irgacure OXE-02: Photoinitiator available from BASF, Germany and having the following formula:

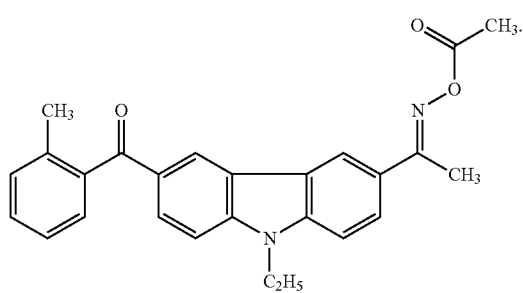 [SMILES: CCn1c2ccc(C(=O)c3ccccc3C)cc2c2cc(/C(C)=N/OC(C)=O)ccc21]

BR10-010: Polymeric particle, 20% dispersed in isopropanol/water mixture (80/20) (Particle size=150 nm; polydispersity=0.08), available from America Dye Source, Inc., Canada and having the following formula:

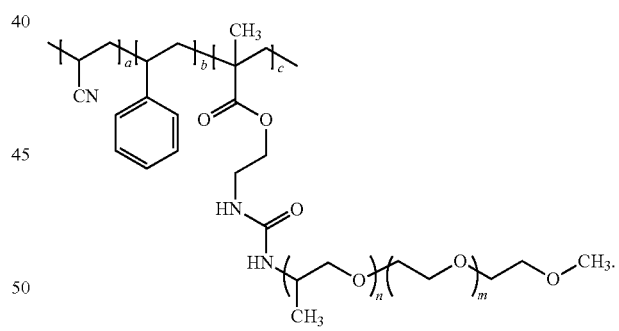

(a = 0.83, b = 0.10 and c = 0.07; n = 29 and m = 6)

UR07-009: Reactive oligomer (60% in 1,3-dioxolane solution), available from American Dye Source, Inc., Canada and having the following formula:

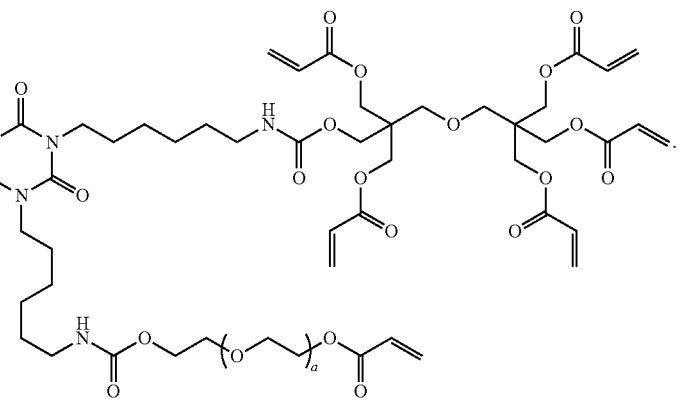

(a = 7)

COBALT: Cobalt (II) oleate salt, available from Sigma Aldrich, Ontario, Canada.
ADD-2204: 2,4,6-Trimethylbenzoyl-diphenyl-phosphineoxide, available from Aceto Corporation, New York, USA.
ADD-9984: N-vinylcaprolactam, available from Sigma Adrich, Ontario, Canada.
ADD-9991: 1,6-hexanediol diacrylate, available from Sigma Adrich, Ontario, Canada.
ADD-9992: 2-phenoxyethyl acrylate, available from TCI America, USA.
ADD-9995: Propoxylated neopentyl glycol diacrylate, available from Sartomer, USA.
ADD-2614: 3-Methacryloxypropyltrimethoxysilane, available from Polysciences, USA.
POL-0138: Aliphatic Polyester Urethane Acrylate, available from Mylan Group, Travinh, Vietnam.
POL-1001: Aromatic monoacrylate oligomer, available from Mylan Group, Travinh, Vietnam.
POL-0137: Stabilizer for radically curable inks, available from Mylan Group, Travinh, Vietnam.
600-B307: Silicone surface additive, available from Mylan Group, Travinh, Vietnam.
COL-1829: Pigment Blue 15:4-25% dispersed in ADD-9995, available from Mylan Group, Travinh, Vietnam.
ADD-9993: Trimethylcyclohexane acrylate, available from Sigma Aldrich, Ontario, Canada.
Yellow-150: Pigment yellow dispersion comprising 7.5 g of CI Pigment Yellow 150 (available from Hangzhou Multicolor Chemical Company, China), 2.5 g of AC07-001 and 40 g of cyclohexanone. The mixture was dispersed for 24 hours using a ball mill. It was filtered with a 5 μm pore filter and cyclohexanone was added to give 15% solid weight.
Red-254: Pigment red dispersion comprising 7.5 g of CI Pigment Red 254 (Hostapern Red D2G 70 LV 2647, available from Clarian, Germany), 2.5 g of AC07-001 and 40 g of cyclohexanone. The mixture was dispersed for 24 hours by using a ball mill. It was filtered with a 5 μm pore filter and cyclohexanone was added to give 15% solid weight.
Green-36: Pigment green dispersion comprising 7.5 g of CI Pigment Green 36 (Heliogen Green K9360, available from BASF, Germany), 2.5 g of AC07-001 and 40 g cyclohexanone. The mixture was dispersed for 24 hours by using a ball mill. It was filtered with a 5 μm pore filter and cyclohexanone was added to give 15% solid weight.
Blue-15: Pigment blue dispersion comprising 7.5 g of CI Pigment Blue 15:6 (Hangzhou Multicolor Chemical Company, China), 2.5 g of AC07-001, and 40 g of cyclohexanone. The mixture was dispersed for 24 hours by using a ball mill. It was filtered with a 5 μm pore filter and cyclohexanone was added to give 15% solid weight.
Black-250: Carbon black dispersion comprising 7.5 g of carbon black (Special Black 250, available from Degussa, USA), 7.5 g of AC07-001 and 40 g of cyclohexanone. The mixture was dispersed for 24 hours by using a ball mill. It was filtered with a 5 μm pore filter and cyclohexanone was added to give 15% solid weight.
Resist vehicle: A resist vehicle was prepared by dissolving 6.0 g of BR07-001, 6.0 g of UR07-015, 1.0 g of Silane in 102 g of cyclohexanone.

Syntheses and Characterization of Compounds of the Invention

Example 1.1

3-Acetyloxime-O-acetate-6,12-diethyl-12-methyl-6,12-dihydro-6-aza-indeno[1,2-b]fluorene The synthesis of 3-acetyloxime-O-acetate-6,12-diethyl-12-methyl-6,12-dihydro-6-aza-indeno[1,2-b]fluorene was performed according to the reaction scheme shown in FIG. 1.

(a) Synthesis of 3-acetyl-6,12-diethyl-12-methyl-6,12-dihydro-6-aza-indeno[1,2-b]fluorene Aluminum chloride (3.43 g, 25.6 mmol) was slowly added into a dichloromethane solution (80 mL) in which were dissolved 6,12-diethyl-12-methyl-6,12-dihydro-6-aza-indeno[1,2-b]fluorene (5.95 g, 20.0 mmol) and acetyl chloride (1.83 mL, 25.7 mmol) at 0° C. under nitrogen atmosphere. After stirring at room temperature overnight, the reaction mixture was poured into ice-water. The product was extracted twice with dichloromethane. The combined organic layer was washed with brine, and dried over MgSO$_4$. The dichloromethane was removed under high vacuum and the product thus obtained was used for the next step without further purification.

(b) Synthesis of 3-acetyloxime-6,12-diethyl-12-methyl-6,12-dihydro-6-aza-indeno[1,2-b]fluorene 3-Acetyl-6,12-diethyl-12-methyl-6,12-dihydro-6-aza-indeno[1,2-b]fluorene (3.39 g, 10.0 mmol) was added into a solution mixture containing 100 mL of 1,3-dioxane, sodium acetate (1.06 g, 13.0 mmol), hydroxylammonium chloride (0.83 g, 12.0 mmol) and water (60 mL). The reaction mixture was refluxed overnight, cooled to room temperature, and then poured into water. The product was extracted with ethyl acetate. The combined organic layer was washed twice with water, dried over MgSO$_4$, and concentrated to give a residue, which was further dried in a vacuum oven at 40° C. The product thus obtained was used for the next step without further purification (3.22 g, 92% yield).

(c) Synthesis of 3-acetyloxime-O-acetate-6,12-diethyl-12-methyl-6,12-dihydro-6-aza-indeno[1,2-b]fluorene Triethylamine (1.7 mL, 12.2 mmol) and acetyl chloride (915 μL, 12.8 mmol) were slowly added into 100 mL of a tetrahydrofuran solution containing 3-acetyloxime-6,12-diethyl-12-methyl-6,12-dihydro-6-aza-indeno[1,2-b]fluorene (3.54 g, 10.0 mmol) at 0° C. under nitrogen atmosphere. After 3 hours stirring at room temperature, the reaction mixture was poured in water. The product was extracted with ethyl acetate. The combined organic layer was washed twice with water, dried with MgSO$_4$, and concentrated by vacuum evaporation to give a residue, which was purified by flash chromatography on silica gel with ethyl acetate and hexane as eluents. The solvent was removed using vacuum evaporation to give a white powder product with 32% yield and 99% purity.

Example 1.2

Figure 2:
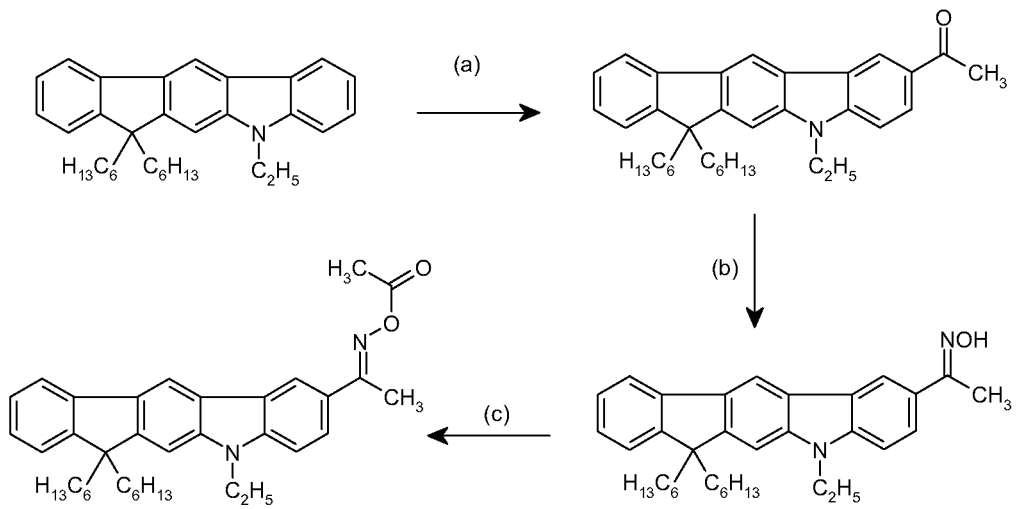
FIG. 2 shows the reaction scheme for the production of 7-acetyloxime-O-acetate-10-ethyl-12,12-dihexyl-10,12-dihydro-10-aza-indeno[2,1-b]fluorene.

7-Acetyloxime-O-acetate-10-ethyl-12,12-dihexyl-10,12-dihydro-10-aza-indeno[2,1-b]fluorene The synthesis of 7-acetyloxime-O-acetate-10-ethyl-12,12-dihexyl-10,12-dihydro-10-aza-indeno[2,1-b]fluorene was performed according to the reaction scheme shown in FIG. 2.

(a) Synthesis of 7-acetyl-10-ethyl-12,12-dihexyl-10,12-dihydro-10-aza-indeno[2,1-b]fluorene Aluminum chloride (3.43 g, 25.6 mmol) was slowly added into a dichloromethane solution (80 mL) in which were dissolved 10-ethyl-12,12-dihexyl-10,12-dihydro-10-aza-indeno[2,1-b]fluorene (5.95 g, 20.0 mmol) and acetyl chloride (1.83 mL, 25.7 mmol) at 0° C. under nitrogen atmosphere. After stirring at room temperature overnight, the reaction mixture was poured into ice-water. The product was extracted twice with dichloromethane. The combined organic layer was washed with brine, and dried over MgSO$_4$. The dichloromethane was removed under high vacuum and the product thus obtained was used for the next step without further purification.

(b) Synthesis of 7-acetyloxime-10-ethyl-12,12-dihexyl-10,12-dihydro-10-aza-indeno[2,1-b]-fluorene 7-Acetyl-10-ethyl-12,12-dihexyl-10,12-dihydro-10-aza-indeno[2,1-b]fluorene (3.39 g, 10.0 mmol) was added into a solution mixture containing 100 mL of 1,3-dioxane, sodium acetate (1.06 g, 13.0 mmol), hydroxylammonium chloride (0.83 g, 12.0 mmol) and water (60 mL). The reaction mixture was refluxed overnight, cooled to room temperature, and then poured into water. The product was extracted with ethyl acetate. The combined organic layer was washed twice with water, dried over MgSO$_4$, and concentrated to give a residue, which was further dried in a vacuum oven at 40° C. The product thus obtained was used for the next step without further purification (3.22 g, 92% yield).

(c) Synthesis of 6-acetyloxime-O-acetate-1,1-dihexyl indeno-[2,3-b]-9-ethyl carbazole Triethylamine (1.7 mL, 12.2 mmol) was slowly added into 100 mL of a tetrahydrofuran solution containing 7-acetyloxime-10-ethyl-12,12-dihexyl-10,12-dihydro-10-aza-indeno[2,1-b]fluorene (3.54 g, 10.0 mmol) and acetyl chloride (915 μL, 12.8 mmol) at 0° C. under nitrogen atmosphere. After 3 hours stirring at room temperature, the reaction mixture was poured in water. The product was extracted with ethyl acetate. The combined organic layer was washed twice with water, dried with MgSO$_4$, and concentrated by vacuum evaporation to give a residue, which was purified by flash chromatography on silica gel with ethyl acetate and hexane as eluent. The solvent was removed using vacuum evaporation to give a white powder product with 32% yield and 99% purity.

Example 1.3

Figure 3:
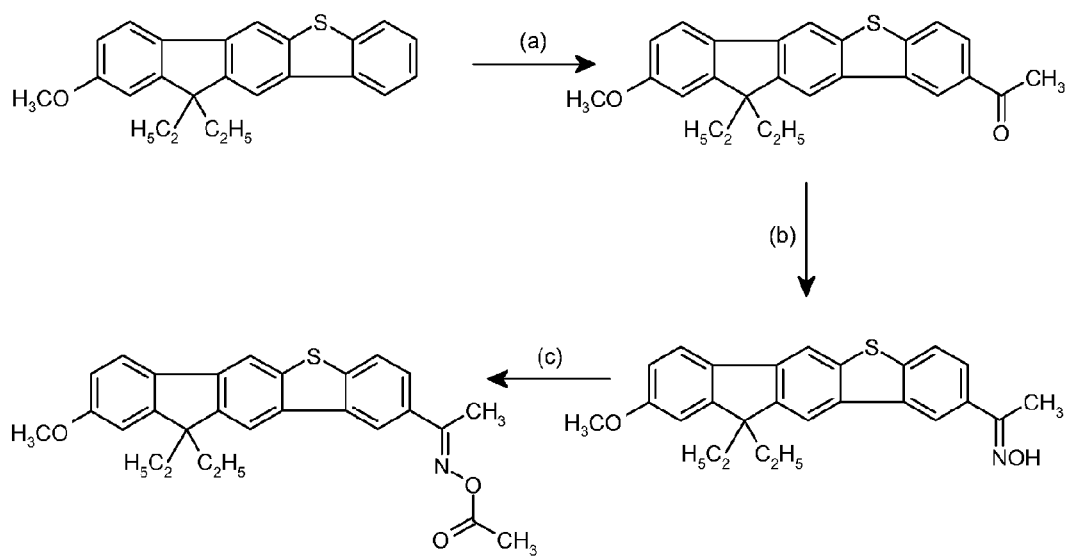
FIG. 3 shows the reaction scheme for the production of 9-acetyloxime-O-acetate-2-methoxy-12,12-diethyl-6,12-dihydro-6-thia-indeno[1,2-b]fluorene.

9-Acetyloxime-O-acetate-2-methoxy-12,12-diethyl-6,12-dihydro-6-thia-indeno[1,2-b]fluorene The synthesis of 9-acetyloxime-O-acetate-2-methoxy-12,12-diethyl-6,12-dihydro-6-thia-indeno[1,2-b]fluorene was performed according to the reaction scheme shown in FIG. 3.

(a) Synthesis of 9-acetyl-2-methoxy-12,12-diethyl-6,12-dihydro-6-thia-indeno[1,2-b]fluorene Aluminum chloride (3.43 g, 25.6 mmol) was slowly added into a dichloromethane solution (100 mL) in which were dissolved 2-methoxy-12,12-diethyl-6,12-dihydro-6-thia-indeno[1,2-b]fluorene (6.60 g, 20.0 mmol) and acetyl chloride (1.83 mL, 25.7 mmol) at 0° C. under nitrogen atmosphere. After stirring at room temperature overnight, the reaction mixture was poured into ice-water. The product was extracted twice with dichloromethane. The combined organic layer was washed with brine, and dried over MgSO$_4$. Dichloromethane was removed under high vacuum and the product thus obtained was used for the next step without further purification.

(b) Synthesis of 9-acetyloxime-2-methoxy-12,12-diethyl-6,12-dihydro-6-thia-indeno[1,2-b]fluorene 9-Acetyl-2-methoxy-12,12-diethyl-6,12-dihydro-6-thia-indeno[1,2-b]fluorene (3.56 g, 10.0 mmol) was added into a solution mixture containing 100 mL of 1,3-dioxane, sodium acetate (1.06 g, 13.0 mmol), hydroxylammonium chloride (0.83 g, 12.0 mmol) and water (60 mL). The reaction mixture was refluxed overnight, cooled to room temperature, and then poured into water. The product was extracted with ethyl acetate. The combined organic layer was washed twice with water, dried over MgSO$_4$, and concentrated to give a residue, which was further dried in a vacuum oven at 40° C. The product thus obtained was used for the next step without further purification.

(c) Synthesis of 9-acetyloxime-O-acetate-2-methoxy-12,12-diethyl-6,12-dihydro-6-thia-indeno[1,2-b]fluorene Triethylamine (1.7 mL, 12.2 mmol) was slowly added into 100 mL of a tetrahydrofuran solution containing 9-acetyloxime-2-methoxy-12,12-diethyl-6,12-dihydro-6-thia-indeno[1,2-b]fluorene (3.87 g, 10.0 mmol) and acetyl chloride (915 µL, 12.8 mmol) at 0° C. under nitrogen atmosphere. After 3 hours stirring at room temperature, the reaction mixture was poured in water. The product was extracted with ethyl acetate. The combined organic layer was washed twice with water, dried with $MgSO_4$, and concentrated to give a residue, which was purified by flash chromatography using ethyl acetate-hexane as eluent. The solvent was removed using vacuum evaporations to give a white powder product with 32% yield and 99% purity.

Example 1.4

Figure 4:
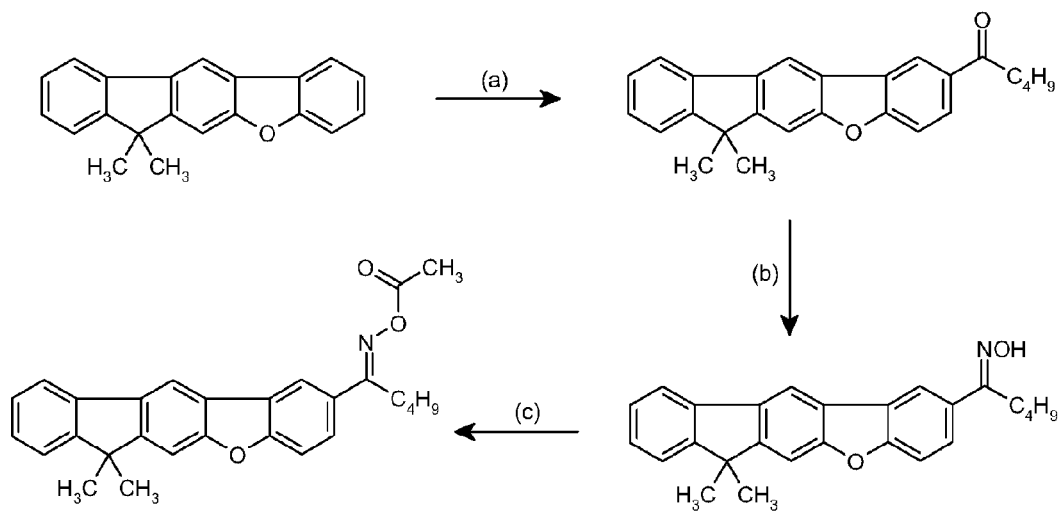
FIG. 4 shows the reaction scheme for the production of 7-acetyloxime-O-acetate-12,12-dimethyl-10,12-dihydro-10-oxo-indeno[2,1-b]fluorene.

7-Acetyloxime-O-acetate-12,12-dimethyl-10,12-dihydro-10-oxo-indeno[1,2-b]fluorene The synthesis of 7-acetyloxime-O-acetate-12,12-dimethyl-10,12-dihydro-10-oxo-indeno[2,1-b]fluorene was performed according to the scheme shown in FIG. 4.

(a) Synthesis of 7-butyryl-12,12-dimethyl-10,12-dihydro-10-oxo-indeno[2,1-b]fluorene Aluminum chloride (3.43 g, 25.6 mmol) was slowly added into a dichloromethane solution (80 mL) in which were dissolved 12,12-dimethyl-10,12-dihydro-10-oxo-indeno[2,1-b]fluorene (5.68 g, 20.0 mmol) and acetyl chloride (1.83 mL, 25.7 mmol) at 0° C. under nitrogen atmosphere. After stirring at room temperature overnight, the reaction mixture was poured into ice-water. The product was extracted twice with dichloromethane. The combined organic layer was washed with brine, and dried over $MgSO_4$. Dichloromethane was removed under high vacuum and the product thus obtained was used for the next step without further purification.

(b) Synthesis of 7-butyryloxime-12,12-dimethyl-10,12-dihydro-10-oxo-indeno[2,1-b]fluorene 7-Butyryl-12,12-dimethyl-10,12-dihydro-10-oxo-indeno[2,1-b]fluorene (3.26 g, 10.0 mmol) was added into a solution mixture containing 100 mL of 1,3-dioxane, sodium acetate (1.06 g, 13.0 mmol), hydroxylammonium chloride (0.83 g, 12.0 mmol) and water (60 mL). The reaction mixture was refluxed overnight, cooled to room temperature, and then poured into water. The product was extracted with ethyl acetate. The combined organic layer was washed twice with water, dried over $MgSO_4$, and concentrated to give a residue, which was further dried in a vacuum oven at 40° C. The product thus obtained was used for the next step without further purification.

(c) Synthesis of 7-butyryloxime-O-acetate-12,12-dimethyl-10,12-dihydro-10-oxo-indeno[2,1-b]fluorene Triethylamine (1.7 mL, 12.2 mmol) was slowly added into a tetrahydrofuran solution (100 mL) containing 7-butyryloxime-12,12-dimethyl-10,12-dihydro-10-oxo-indeno[1,2-b]fluorene (3.41 g, 10.0 mmol) and acetyl chloride (915 µL, 12.8 mmol) at 0° C. under nitrogen atmosphere. After 3 hours stirring at room temperature, the reaction mixture was poured in water. The product was extracted with ethyl acetate. The combined organic layer was washed twice with water, dried with $MgSO_4$, and concentrated by vacuum evaporation to give a residue, which was purified by flash chromatography on silica gel with ethyl acetate and hexane as eluents. The solvent was removed using vacuum evaporation to give a white powder product with 37% yield and 99% purity.

Example 1.5

Figure 5:
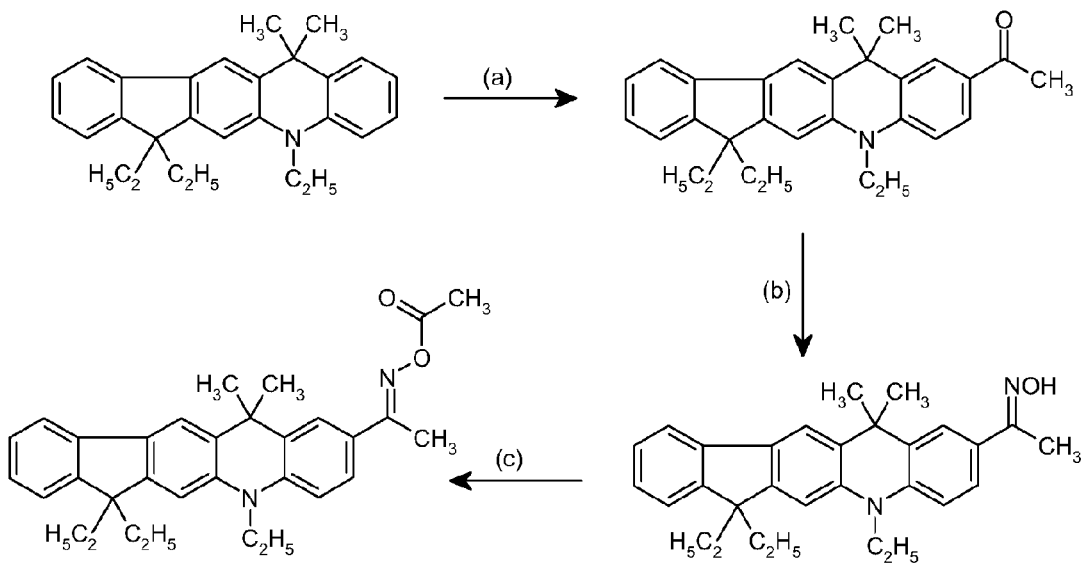
FIG. 5 shows the reaction scheme for the production of 8-acetyloxime-O-acetate-11,13,13-triethyl-6,6-dimethyl-11,13-dihydro-6H-11-aza-indeno[2,1-b]anthracene.

8-Acetyloxime-O-acetate-11,13,13-triethyl-6,6-dimethyl-11,13-dihydro-6H-11-aza-indeno[2,1-b]anthracene The synthesis of 8-acetyloxime-O-acetate-11,13,13-triethyl-6,6-dimethyl-11,13-dihydro-6H-11-aza-indeno[2,1-b]anthracene was performed according to the scheme shown in FIG. 5.

(a) Synthesis of 8-acetyl-11,13,13-triethyl-6,6-dimethyl-11,13-dihydro-6H-11-aza-indeno[2,1-b]anthracene Aluminum chloride (3.43 g, 25.6 mmol) was slowly added into a dichloromethane solution (80 mL) in which were dissolved 11,13,13-triethyl-6,6-dimethyl-11,13-dihydro-6H-11-aza-indeno[2,1-b]anthracene (6.80 g, 20.0 mmol) and acetyl chloride (1.83 mL, 25.7 mmol) at 0° C. under nitrogen atmosphere. After stirring at room temperature overnight, the reaction mixture was poured into ice-water. The product was extracted twice with dichloromethane. The combined organic layer was washed with brine, and dried over $MgSO_4$. Dichloromethane was removed under high vacuum and the product thus obtained was used for the next step without further purification.

(b) Synthesis of 8-acetyloxime-11,13,13-triethyl-6,6-dimethyl-11,13-dihydro-6H-11-aza-indeno[2,1-b]anthracene 8-Acetyl-11,13,13-triethyl-6,6-dimethyl-11,13-dihydro-6H-11-aza-indeno[2,1-b]anthracene (3.82 g, 10.0 mmol) was added into a solution mixture containing 100 mL of 1,3-dioxane, sodium acetate (1.06 g, 13.0 mmol), hydroxylammonium chloride (0.83 g, 12.0 mmol) and water (60 mL). The reaction mixture was refluxed overnight, cooled to room temperature, and then poured into water. The product was extracted with ethyl acetate. The combined organic layer was washed twice with water, dried over $MgSO_4$, and concentrated to give a residue, which was further dried in a vacuum oven at 40° C. The product thus obtained was used for the next step without further purification.

(c) Synthesis of 8-acetyloxime-O-acetate-11,13,13-triethyl-6,6-dimethyl-11,13-dihydro-6H-11-aza-indeno[2,1-b]anthracene Triethylamine (1.7 mL, 12.2 mmol) was slowly added into 100 mL of a tetrahydrofuran solution containing 8-acetyloxime-11,13,13-triethyl-6,6-dimethyl-11,13-dihydro-6H-11-aza-indeno[1,2-b]anthracene (3.97 g, 10.0 mmol) and acetyl chloride (915 µL, 12.8 mmol) at 0° C. under nitrogen atmosphere. After 3 hours stirring at room temperature, the reaction mixture was poured in water. The product was extracted with ethyl acetate. The combined organic layer was washed twice with water, dried with $MgSO_4$, and concentrated by vacuum evaporation to give a residue, which was purified by flash chromatography on silica gel with ethyl acetate and hexane as eluents. The solvent was removed using vacuum evaporation to give a white powder product with 46% yield and 99% purity.

Example 1.6

Figure 6:
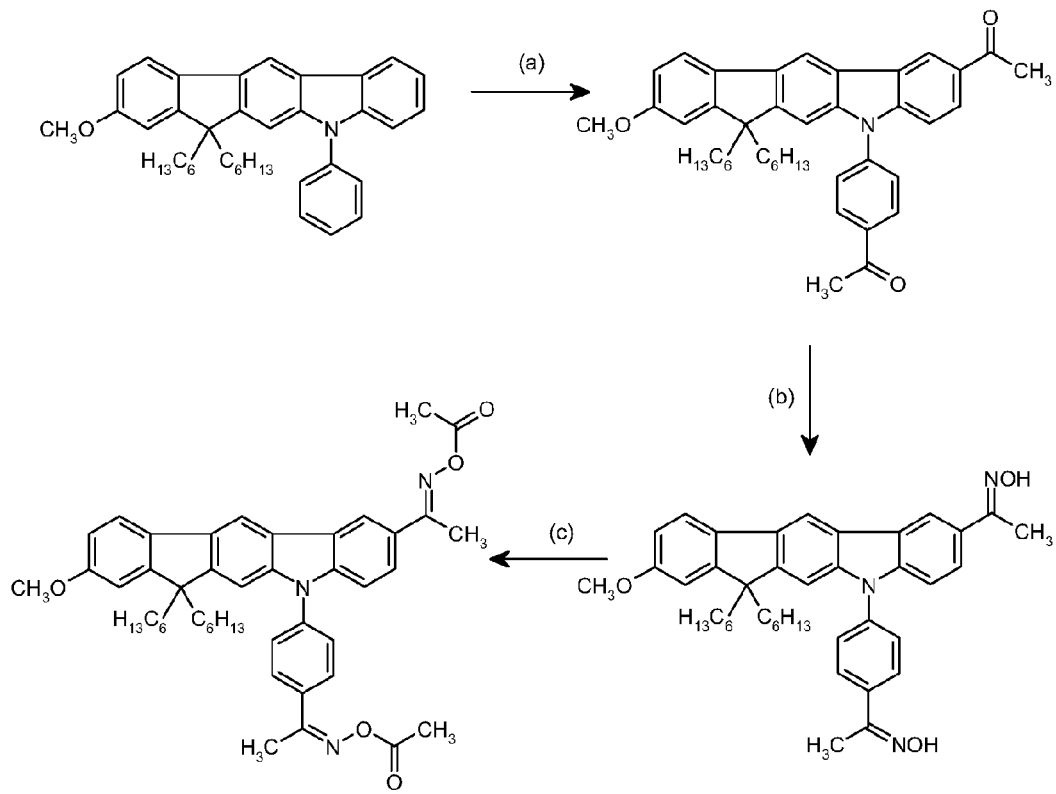
FIG. 6 shows the reaction scheme for the production of 10-(4-acetyloxime-O-acetate phenyl)-7-acetyloxime-O-acetate-2-methoxy-12,12-dihexyl-10,12-dihydro-10-aza-indeno[2,1-b]fluorene.

10-(4-acetyloxime-O-acetate phenyl)-7-acetyloxime-O-acetate-2-methoxy-12,12-dihexyl-10,12-dihydro-10-aza-indeno[2,1-b]fluorene The synthesis of 10-(4-acetyloxime-O-acetate phenyl)-7-acetyloxime-O-acetate-2-methoxy-12,12-dihexyl-10,12-dihydro-10-aza-indeno[2,1-b]fluorene was performed according to the scheme shown in FIG. 6.

(a) Synthesis of 10-(4-acetyl phenyl)-7-acetyl-2-methoxy-12,12-dihexyl-10,12-dihydro-10-aza-indeno[2,1-b]fluorene Aluminum chloride (8.00 g, 60.0 mmol) was slowly added into a dichloromethane solution (120 mL) in which were dissolved 2-methoxy-10-phenyl-12,12-dihexyl-10,12-dihydro-10-aza-indeno[2,1-b]fluorene (7.47 g, 20.0 mmol) and acetyl chloride (3.56 mL, 50.0 mmol) at 0° C. under nitrogen atmosphere. After stirring at room temperature overnight, the reaction mixture was cooled to room temperature and poured into ice-water. The product was extracted twice with dichloromethane. The combined organic layer was washed with brine, and dried over $MgSO_4$. Dichloromethane was removed under high vacuum and the product thus obtained was used for the next step without further purification.

(b) Synthesis of 10-(4-acetyloxime phenyl)-7-acetyloxime-2-methoxy-12,12-dihexyl-10,12-dihydro-10-aza-indeno[2,1-b]fluorene 10-(4-acetylphenyl)-7-acetyl-2-methoxy-12,12-dihexyl-10,12-dihydro-10-aza-indeno[2,1-b]fluorene (4.58 g, 10.0 mmol) was added into a solution mixture containing 120 mL of 1,3-dioxane, sodium acetate (2.46 g, 30.0 mmol), hydroxylammonium chloride (2.08 g, 30.0 mmol) and water (80 mL). The reaction mixture was refluxed overnight, cooled to room temperature, and then poured into water. The product was extracted with ethyl acetate. The combined organic layer was washed twice with water, dried over $MgSO_4$, and concentrated to give a residue, which was further dried in a vacuum oven at 40° C. The product thus obtained was used for the next step without further purification.

(c) Synthesis of 10-(4-acetyloxime-O-acetate phenyl)-7-acetyloxime-O-acetate-2-methoxy-12,12-dihexyl-10,12-dihydro-10-aza-indeno[2,1-b]fluorene Triethylamine (4.18 mL, 30.0 mmol) was slowly added into 100 mL of tetrahydrofuran solution containing 10-(4-acetyloxime phenyl)-7-acetyloxime-2-methoxy-12,12-dihexyl-10,12-dihydro-10-aza-indeno[2,1-b]fluorene (4.88 g, 10.0 mmol) and acetyl chloride (2.13 mL, 30.0 mmol) at 0° C. under nitrogen atmosphere. After 5 hours stirring at room temperature, the reaction mixture was poured in water. The product was extracted with ethyl acetate. The combined organic layer was washed twice with water, dried with $MgSO_4$, and concentrated by vacuum evaporation to give a residue, which was purified by flash chromatography on silica gel with ethyl acetate and hexane as eluents. The solvent was removed using vacuum evaporation to give a white powder product with 56% yield and 99% purity.

Example 1.7

Figure 7:
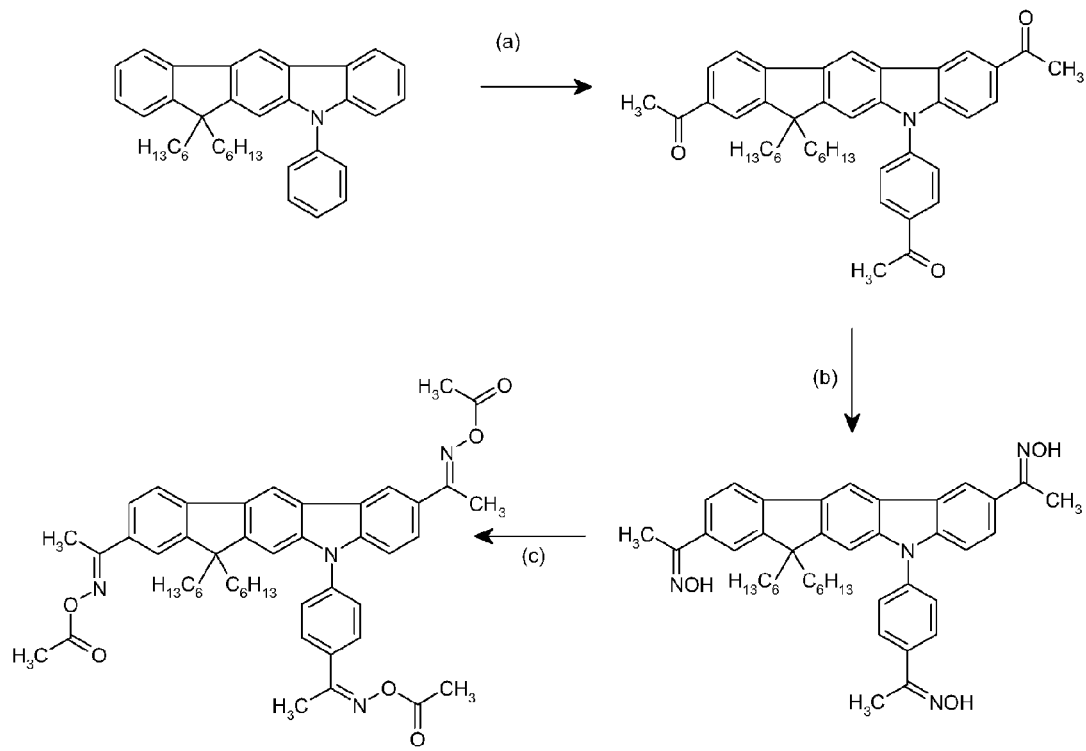
FIG. 7 shows the reaction scheme for the production of 10-(4-acetyloxime-O-acetate phenyl)-2,7-diacetyloxime-O-acetate-12,12-dihexyl-10,12-dihydro-10-aza-indeno[2,1-b]fluorene.

10-(4-acetyloxime-O-acetate phenyl)-2,7-diacetyloxime-O-acetate-12,12-dihexyl-10,12-dihydro-10-aza-indeno[2,1-b]fluorene The synthesis of 10-(4-acetyloxime-O-acetate phenyl)-2,7-diacetyloxime-O-acetate-12,12-dihexyl-10,12-dihydro-10-aza-indeno[2,1-b]fluorene was performed according to the scheme shown in FIG. 7.

(a) Synthesis of 10-(4-acetyl phenyl)-2,7-diacetyl-12,12-dihexyl-10,12-dihydro-10-aza-indeno[2,1-b]fluorene Aluminum chloride (12.0 g, 90.0 mmol) was slowly added into a dichloromethane solution (120 mL) in which were dissolved 10-ethyl-12,12-dihexyl-10,12-dihydro-10-aza-indeno[2,1-b]fluorine (7.20 g, 20.0 mmol) and acetyl chloride (6.40 mL, 90.0 mmol) at 0° C. under nitrogen atmosphere. After refluxing overnight, the reaction mixture was cooled to room temperature and poured into ice-water. The product was extracted twice with dichloromethane. The combined organic layer was washed with brine, and dried over $MgSO_4$. Dichloromethane was removed under high vacuum and the product thus obtained was used for the next step without further purification.

(b) Synthesis of 10-(4-acetyloxime phenyl)-2,7-diacetyloxime-12,12-dihexyl-10,12-dihydro-10-aza-indeno[2,1-b]fluorene 10-(4-acetylphenyl)-2,7-diacetyl-12,12-dihexyl-10,12-dihydro-10-aza-indeno[2,1-b]fluorene (4.86 g, 10.0 mmol) was added into a solution mixture containing 150 mL of 1,3-dioxane, sodium acetate (4.92 g, 60.0 mmol), hydroxylammonium chloride (4.17 g, 60.0 mmol) and water (100 mL). The reaction mixture was refluxed overnight, cooled to room temperature, and then poured into water. The product was extracted with ethyl acetate. The combined organic layer was washed twice with water, dried over $MgSO_4$, and concentrated to give a residue, which was further dried in a vacuum oven at 40° C. The product thus obtained was used for the next step without further purification.

(c) Synthesis of 10-(4-acetyloxime-O-acetate phenyl)-2,7-diacetyloxime-O-acetate-12,12-dihexyl-10,2-dihydro-10-aza-indeno[2,1-b]fluorene Triethylamine (8.36 mL, 60.0 mmol) was slowly added into 100 mL of a tetrahydrofuran solution containing 10-(4-acetyloxime phenyl)-2,7-diacetyloxime-12,12-dihexyl-10,12-dihydro-10-aza-indeno[2,1-b]fluorene (5.31 g, 10.0 mmol) and acetyl chloride (4.27 mL, 60.0 mmol) at 0° C. under nitrogen atmosphere. After 3 hours stirring at room temperature, the reaction mixture was poured in water. The product was extracted with ethyl acetate. The combined organic layer was washed twice with water, dried with $MgSO_4$, and concentrated by vacuum evaporation to give a residue, which was purified by flash chromatography on silica gel with ethyl acetate and hexane as eluents. The solvent was removed using vacuum evaporation to give a white powder product with 45% yield and 99% purity.

Example 1.8

3,9-Diacetyloxime-O-acetate-6-hexyl-6H-12-thia-6-aza-indeno[1,2-b]fluorene

Figure 8:
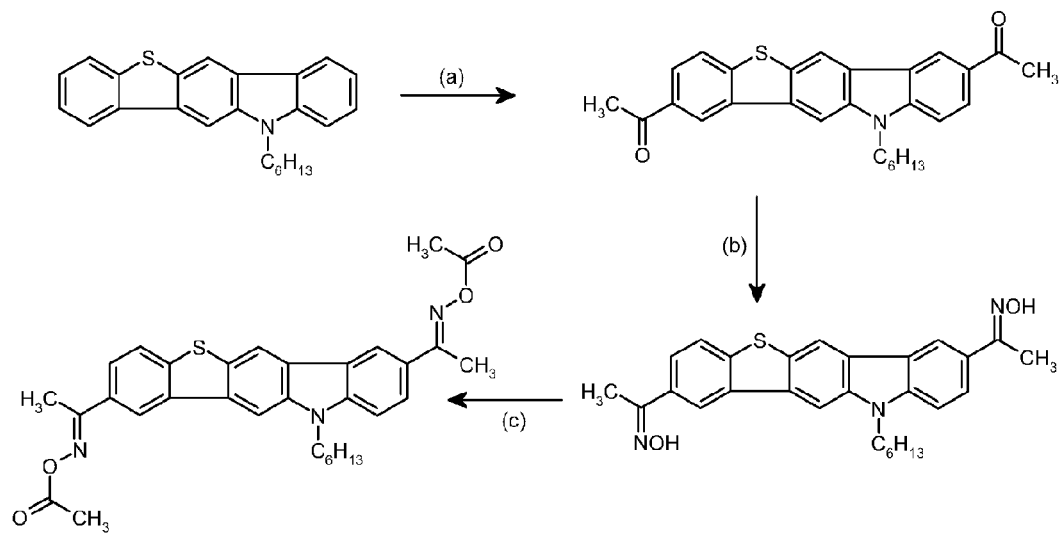
FIG. 8 shows the reaction scheme for the production of 3,9-diacetyloxime-O-acetate-6-hexyl-6H-12-thia-6-aza-indeno[1,2-b]fluorene.

The synthesis of 3,9-diacetyloxime-O-acetate-6-hexyl-6H-12-thia-6-aza-indeno[1,2-b]fluorene was performed according to the scheme shown in FIG. 8.

(a) Synthesis of 3,9-Diacetyl-6-hexyl-6H-12-thia-6-aza-indeno[1,2-b]fluorene Aluminum chloride (8.00 g, 60.0 mmol) was slowly added into a dichloromethane solution (120 mL) in which were dissolved 6-hexyl-6H-12-thia-6-aza-indeno[1,2-b]fluorene (5.75 g, 20.0 mmol) and acetyl chloride (3.56 mL, 50.0 mmol) at 0° C. under nitrogen atmosphere. After stirring at room temperature overnight, the reaction mixture was cooled to room temperature and poured into ice-water. The product was extracted twice with dichloromethane. The combined organic layer was washed with brine, and dried over $MgSO_4$. Dichloromethane was removed under high vacuum and the product thus obtained was used for the next step without further purification.

(b) Synthesis of 3,9-Diacetyloxime-6-hexyl-6H-12-thia-6-aza-indeno[1,2-b]fluorene 3,9-Diacetyl-6-hexyl-6H-12-thia-6-aza-indeno[1,2-b]fluorene (3.71 g, 10.0 mmol) was added into a solution mixture containing 120 mL of 1,3-dioxane, sodium acetate (3.28 g, 40.0 mmol), hydroxylammonium chloride (2.78 g, 40.0 mmol) and water (80 mL). The reaction mixture was refluxed overnight, cooled to room temperature, and then poured into water. The product was extracted with ethyl acetate. The combined organic layer was washed twice with water, dried over $MgSO_4$, and concentrated to give a residue, which was further dried in a vacuum oven at 40° C. The product thus obtained was used for the next step without further purification.

(c) Synthesis of 3,9-Diacetyloxime-O-acetate-6-hexyl-6H-12-thia-6-aza-indeno[1,2-b]fluorene Triethylamine (5.78 mL, 40.0 mmol) was slowly added into 100 mL of a tetrahydrofuran solution containing 3,9-diacetyloxime-6-hexyl-6H-12-thia-6-aza-indeno[1,2-b]fluorene (4.01 g, 10.0 mmol) and acetyl chloride (3.45 mL, 40.0 mmol) at 0° C. under nitrogen atmosphere. After 3 hours stirring at room temperature, the reaction mixture was poured in water. The product was extracted with ethyl acetate. The combined organic layer was washed twice with water, dried with $MgSO_4$, and concentrated by vacuum evaporation to give a residue, which was purified by flash chromatography on silica gel with ethyl acetate and hexane as eluents. The solvent was removed using vacuum evaporation to give a white powder product with 68% yield and 99% purity.

Example 1.9

10-Hexyl-10H-10-aza-indeno[2,1-b]fluoren-12-O-acetyloxime

Figure 9:
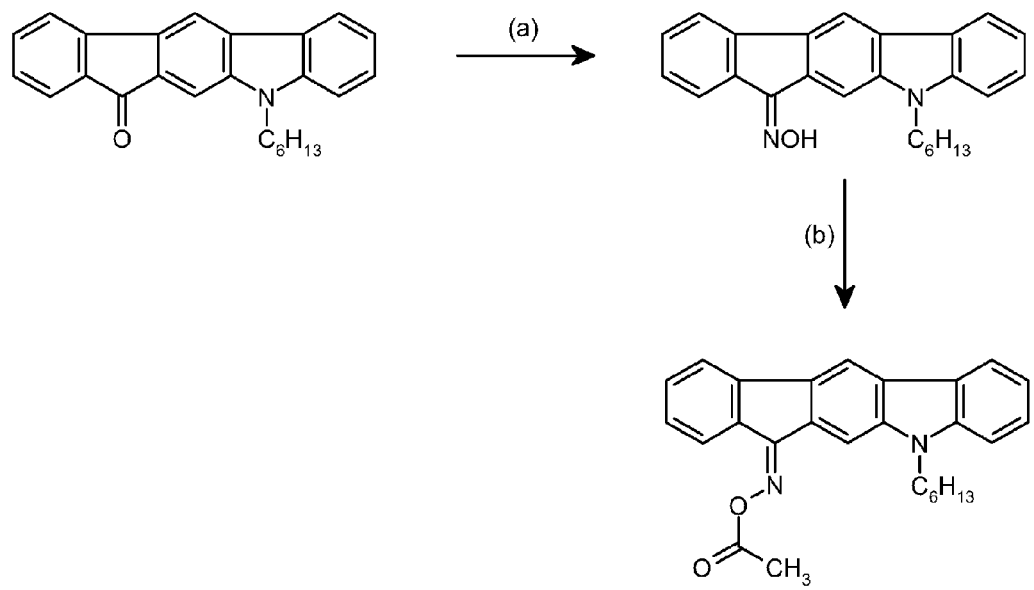
FIG. 9 the reaction scheme for the production of 10-hexyl-10H-10-aza-indeno[2,1-b]fluoren-12-O-acetyloxime.

The synthesis of 10-hexyl-10H-10-aza-indeno[2,1-b]fluoren-12-O-acetyloxime was performed according to the scheme shown in FIG. 9.

(a) Synthesis of 10-hexyl-10H-10-aza-indeno[2,1-b]fluoren-12-oxime

10-Hexyl-10H-10-aza-indeno[2,1-b]fluoren-12-one (2.83 g, 10.0 mmol) and hydroxylammonium chloride (3.35 g, 40.0 mmol) were dissolved in 120 mL of 1,3-dioxane. Pyridine (3.96, 50 mmol) was added into the solution via a syringe. The reaction mixture was stirred overnight. The solvent was removed by vacuum evaporation and then poured into water. The product was extracted with ethyl acetate. The combined organic layer was washed twice with water and brine, dried over $MgSO_4$, and concentrated to give a residue, which was further dried in a vacuum oven at 40° C. The product thus obtained was used for the next step without further purification.

(b) Synthesis of 10-hexyl-10H-10-aza-indeno[2,1-b]fluoren-12-O-acetyloxime

Triethylamine (3.40 mL, 24.4 mmol) was slowly added into 80 mL of a tetrahydrofuran solution containing 10-hexyl-10H-10-aza-indeno[2,1-b]fluoren-12-oxime (2.98 g, 10.0 mmol) and acetyl chloride (1.83 mL, 25.6 mmol) at 0° C. under nitrogen atmosphere. After 3 hours stirring at room temperature, the reaction mixture was poured in water. The product was extracted with ethyl acetate. The combined organic layer was washed twice with water, dried with $MgSO_4$, and concentrated by vacuum evaporation to give a residue, which was purified by flash chromatography on silica gel with ethyl acetate and hexane as eluents. The solvent was removed using vacuum evaporation to give a white powder product with 86% yield and 99% purity.

Example 1.10

Figure 10:
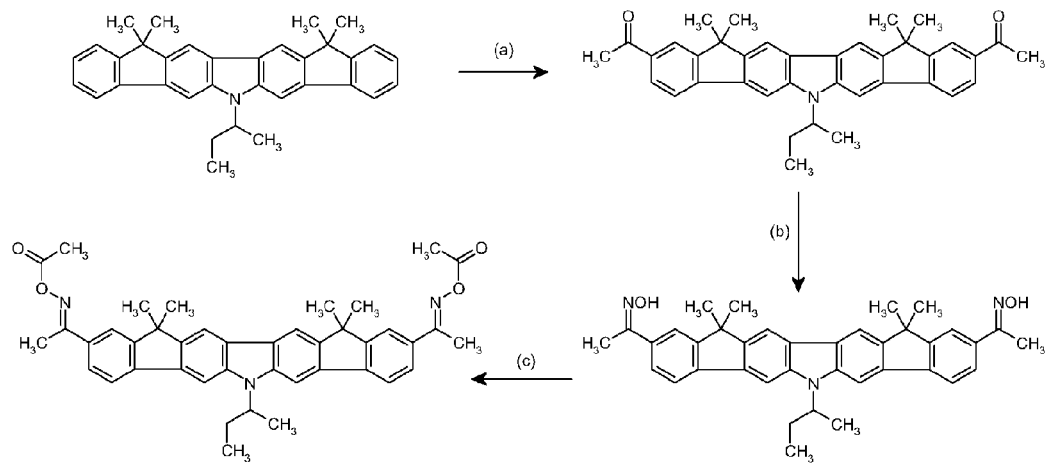
FIG. 10 the reaction scheme for the production of 7,7'-acetyloxime-O-acetate-1,1'-dimethyl-bisindeno[3,2-b:2',3'-h]-9-sec-butyl carbazole.

7,7'-Acetyloxime-O-acetate-1,1'-Dimethyl-bisindeno[3,2-b:2',3'-h]-9-sec-butyl carbazole The synthesis of 7,7'-acetyloxime-O-acetate-1,1'-Dimethyl-bisindeno[3,2-b:2',3'-h]-9-sec-butyl carbazole was performed according to the scheme shown in FIG. 10.

(a) Synthesis of 7,7'-acetyl-1,1'-Dimethyl-bisindeno[3,2-b:2',3'-h]-9-sec-butyl carbazole Aluminum chloride (8.00 g, 60.0 mmol) was slowly added into a dichloromethane solution (150 mL) in which were dissolved 1,1'-dimethyl-bisindeno[3,2-b:2',3'-h]-9-sec-butyl carbazole (9.12 g, 20.0 mmol) and acetyl chloride (3.56 mL, 50.0 mmol) at 0° C. under nitrogen atmosphere. After stirring at room temperature overnight, the reaction mixture was cooled to room temperature and poured into ice-water. The product was extracted twice with dichloromethane. The combined organic layer was washed with brine, and dried over $MgSO_4$. Dichloromethane was removed under high vacuum and the product thus obtained was used for the next step without further purification.

(b) Synthesis of 7,7'-Acetyloxime-1,1'-dimethyl-bisindeno[3,2-b:2',3'-h]-9-sec-butyl carbazole 7,7'-Acetyl-1,1'-dimethyl-bisindeno[3,2-b:2',3'-h]-9-sec-butyl carbazole (5.40 g, 10.0 mmol) was added into a solution mixture containing 120 mL of 1,3-dioxane, sodium acetate (2.46 g, 30.0 mmol), hydroxylammonium chloride (2.08 g, 30.0 mmol) and water (80 mL). The reaction mixture was stirred at room temperature overnight, cooled to room temperature, and then poured into water. The product was extracted with ethyl acetate. The combined organic layer was washed twice with water, dried over MgSO$_4$, and concentrated to give a residue, which was further dried in a vacuum oven at 40° C. The product thus obtained was used for the next step without further purification.

(c) Synthesis of 7,7'-Acetyloxime-O-acetate-1,1'-dimethyl-bisindeno[3,2-b:2',3'-h]-9-sec-butyl carbazole Triethylamine (4.18 mL, 30.0 mmol) was slowly added into 100 mL of a tetrahydrofuran solution containing 7,7'-acetyloxime-1,1'-dimethyl-bisindeno[3,2-b:2',3'-h]-9-sec-butyl carbazole (5.70 g, 10.0 mmol) and acetyl chloride (2.13 mL, 30.0 mmol) at 0° C. under nitrogen atmosphere. After 5 hours stirring at room temperature, the reaction mixture was poured in water. The product was extracted with ethyl acetate. The combined organic layer was washed twice with water, dried with MgSO$_4$, and concentrated by vacuum evaporation to give a residue, which was purified by flash chromatography on silica gel with ethyl acetate and hexane as eluents. The solvent was removed using vacuum evaporation to give a white powder product with 76% yield and 99% purity.

Examples 1.11 and Followings

The syntheses of the photoinitiators of Examples 1.11 and following were performed in a flame dried glass wares, which were equipped with mechanical stirrer, water condenser, heating mental, nitrogen gas inlet and temperature controller. The obtained products and intermediates were characterized by FTIR spectrophotometer (Perkin Elmer, Model Spectrum 100), NMR (Nicolet 500 MHz), UV-Vis Spectrophotometer (Perkin Elmer, Model Lambda 25), DSC (TA Instruments, Model Q2000), TGA (TA Instrument, Model Q500), and HPLC (Waters, Model Breeze 2).

Example 1.11

2,7,12 Triacetyloxime-O-acetate-5,5',10,10',15,15'-hexahexyltruxene

The synthesis of 2,7,12 Triacetyloxime-O-acetate-5,5',10,10',15,15'-hexahexyltruxene was performed as follows.

(a) Synthesis of 2,7,12-triacetyloxime-5,5',10,10',15,15'-hexahexyltruxene 2,7,12-Triacetyl-5,5',10,10',15,15'-hexahexyltruxene (prepared according to Example 1.16 below) was dissolved in 180 mL of dioxane in a 500 mL flask. Sodium acetate (283 mg) and hydroxylamine HCl (256 mg) were dissolved in 60 mL of water in a 100 mL flask. This solution was added to the triacetylhexahexyltruxene solution, which was then heated at reflux overnight. Most of the dioxane was removed under low pressure (the product precipitated), then 300 mL of water were added. The suspension was stirred for 30 minutes at room temperature, and then filtered to afford 950 mg (91%) of a yellowish powder.

H$^1$NMR (500 MHz, CDCl$_3$) δ: 8.51-8.46 (m, 3H); 8.12-8.07 (m, 3H); 7.84-7.79 (m, 3H); 3.05-2.92 (m, 6H); 2.70-2.60 (m, 9H); 2.65-2.57 (m, 6H); 2.32-2.17 (m, 36H); 1.05-0.82 (m, 18H); 0.65-0.49 (m, 12H).

(b) Synthesis of 2,7,12-triacetyloxime-O-acetate-5,5',10,10',15,15'-hexahexyltruxene 2,7,12-Triacetyloxime-5,5',10,10',15,15'-hexahexyltruxene was dissolved in 60 mL of THF in a flame dried 100 mL flask under N$_2$. The solution was cooled down to 0° C. in an ice bath. Triethylamine (225 uL) was added, and then acetyl chloride (120 uL) was slowly added. A white precipitate formed. The reaction was monitored with TLC using 15% EtOAc in hexane. After 2 hours at room temperature, the reaction mixture was extracted using EtOAc and water, dried over MgSO$_4$, carefully dried under vacuum, and then suspended in methanol. This suspension was sonicated for 30 minutes and then filtered to afford 235 mg (32%, HPLC purity+99%) of a white powder.

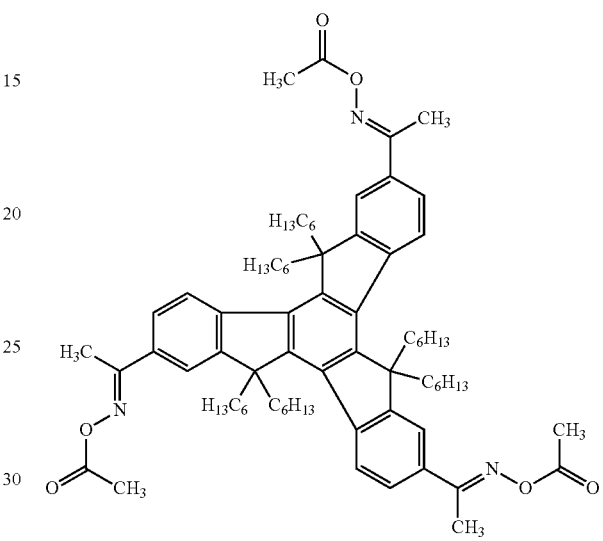

H$^1$NMR (500 MHz, CDCl$_3$) δ 8.42 (d, J=8.5 Hz, 3H); 7.88 (dd, J$^1$=1.7 Hz, J$^2$=8.4 Hz, 3H); 7.82 (d, J=1.7 Hz, 3H); 2.97-2.91 (m, 6H); 2.54 (s, 9H); 2.35 (s, 9H); 2.18-2.11 (m, 6H); 0.98-0.80 (m, 36H); 0.62 (t, J=7.2 Hz, 18H); 0.52-0.45 (m, 12H).

Example 1.12

3,8,13-Triacetyl-5,10,15-trihexyl-10,15-dihydro-5H-5,10,15-triazadiindeno[1,2-a;1',2'-c]fluorene trioxime tri-O-acetate (2E)

The synthesis of 3,8,13-triacetyl-5,10,15-trihexyl-10,15-dihydro-5H-5,10,15-triazadiindeno[1,2-a;1',2'-c]fluorene trioxime tri-O-acetate was performed as follows.

(a) Synthesis of 3,8,13-triacetyl-5,10,15-trihexyl-10,15-dihydro-5H-5,10,15-triazadiindeno[1,2-a;1',2'-c]-fluorene trioxime 3,8,13-Triacetyl-5,10,15-trihexyl-10,15-dihydro-5H-5,10,15-triazadiindeno[1,2-a;1',2'-c]fluorine (800 g, 1.10 mmol, from Example 1.17 below) was dissolved in 1,4-dioxane (120 mL) under nitrogen. The reaction mixture was gently heated to dissolve the solid. A solution of sodium acetate (285 mg, 4.32 mmol) and hydroxyl ammonium chloride (255 mg, 3.67 mmol) in water (40 ml) was added to the reaction mixture, which was then refluxed for 24 h. The reaction was monitored by TLC using ethyl acetate (20%) and hexane (80%) as eluent. After the reaction was completed, the product was precipitated in cold water (200 mL). A beige solid product was obtained by vacuum filtration, copiously washed with water and dried under vacuum at 30° C. until constant weight (790 mg, 93% yield).

(b) Synthesis of 3,8,13-triacetyl-5,10,15-trihexyl-10,15-dihydro-5H-5,10,15-triazadiindeno[1,2-a;1',2'-c]-fluorene trioxime tri-O-acetate Acetyl chloride (167 μL, 2.34 mmol) was slowly added into a tetrahydrofuran solution (500 mL) containing 3,8,13-triacetyl-5,10,15-trihexyl-10,15-dihydro-5H-5,10,15-triazadiindeno[1,2-a;1',2'-c]fluorene trioxime (500 mg, 0.65 mmol) and triethylamine (312 μL, 2.24 mmol). The reaction mixture was stirred overnight. Then solvent was evaporated under reduced pressure to give a dark brown oil. It was purified by column chromatography using silica gel mobile phase and a mixture of ethyl acetate and hexanes as eluent. The solvent was evaporated under vacuum to give a pale brown solid (207 mg, 40%). The melting point and decomposition temperature were determined by differential scanning calorimeter and thermal gravimetric analysis to be around 124° C. and 260° C., respectively.

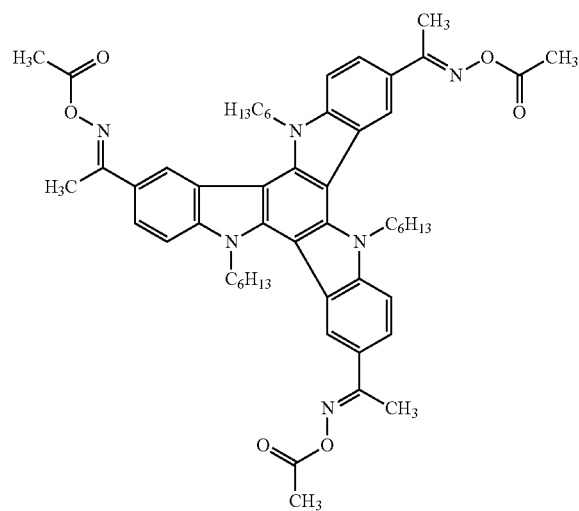

$^1$H NMR (500 MHz, CDCl$_3$) δ 8.71 (s, 3H), 7.88 (d, J=8.6 Hz, 3H), 7.66 (d, J=8.6 Hz, 3H), 4.98 (t, J=7.5 Hz, 6H), 2.60 (s, 9H), 2.36 (s, 9H), 1.95 (p, J=6.6 Hz, 6H), 1.20-1.11 (m, 18H), 0.76 (t, J=7.1 Hz, 9H).

Example 1.13

4,9,13-triethoxyacetyloxime-O-triacetatetruxenone

Figure 11:
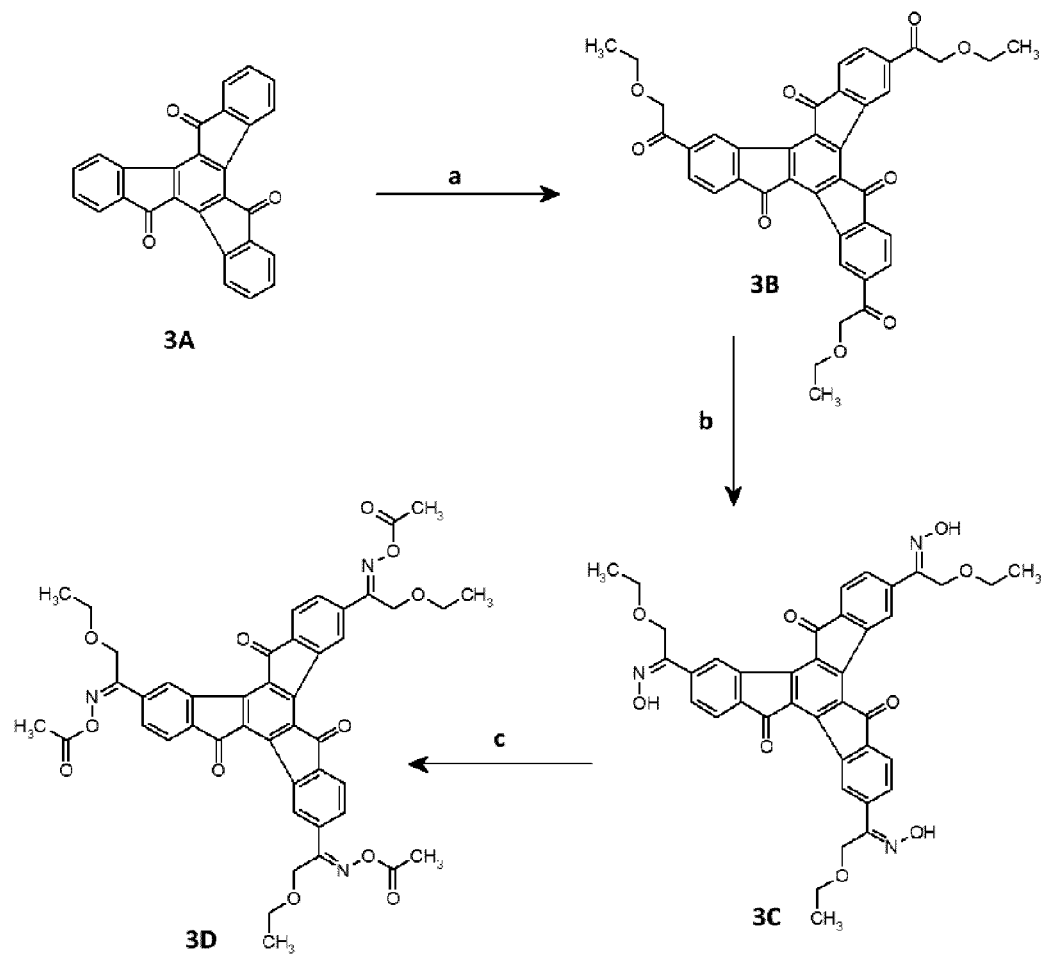
FIG. 11 shows the reaction scheme for the production of 4,9,13-triethoxyacetyloxime-O-triacetatetruxenone.

The synthesis of 4,9,13-triethoxyacetyloxime-O-triacetatetruxenone was performed according to the scheme shown in FIG. 11.

(a) Synthesis of 4,9,13-triethoxyacetyltruxenone (3B)

Aluminum trichloride (1.47 g, 11.02 mmol) was slowly added into a solution containing dichloromethane (10 mL) and truxenone (3A, 1.29 g, 3.35 mmol). The solution turned dark red. Then, ethoxyacetyl chloride (1.81 g, 14.75 mmol) was added dropwise over a period of 2 minutes. The reaction was continued for 36 hours. Then, the reaction mixture was quickly filtered, and concentrated under vacuum to obtain a sticky product. Anhydrous ethanol (15 mL) was added to form a slurry, which was placed in a sonic bath for 30 minutes. The solid product was filtered, copiously washed with ethanol and dried under high vacuum at 30° C. overnight to afford a pale yellow solid (1.83 g, 85% yield).

(b) Synthesis of 4,9,13-triethoxyacetyloximetruxenone (3C)

4,9,13-Triethoxyacetyltruxenone (707 mg, 1.10 mmol) was dissolved in 1,4-dioxane (120 mL) under nitrogen. The reaction mixture was gently heated to dissolve of the solid. A solution of sodium acetate (285 mg, 4.32 mmol) and hydroxylammonium chloride (255 mg, 3.67 mmol) in water (40 ml) was added to the reaction mixture, which was then refluxed for 24 h. The reaction was monitored by TLC using ethyl acetate (20%) and hexane (80%) as eluent. After the reaction was completed, the product was precipitated in cold water (200 mL). A beige solid product was obtained by vacuum filtration, copiously washed with water and dried under vacuum at 30° C. until constant weight (680 mg, 90% yield).

(c) Synthesis of 4,9,13-triethoxyacetyloxime-O-triacetatetmenone (3D)

Acetyl chloride (167 μL, 2.34 mmol) was slowly added into tetrahydrofuran solution (500 mL) containing 4,9,13-triethoxyacetyloximetruxenone (447 mg, 0.65 mmol) and triethylamine (312 μL, 2.24 mmol). The reaction mixture was stirred overnight. Then, the solvent was evaporated under reduced pressure to give a dark brown oil. It was purified by column chromatography using a silica gel mobile phase and a mixture of ethyl acetate and hexanes as eluent. The solvent was evaporated under vacuum to give a pale solid product (158 mg, 30%).

Example 1.14

3,8,13-trihexanoyl-5,10,15-trihexyl-10,15-dihydro-5H-5,10,15-triazadiindeno[1,2-a;1',2'-c]fluorene trioxime tri-O-acetate The synthesis of 3,8,13-trihexanoyl-5,10,15-trihexyl-10,15-dihydro-5H-5,10,15-triazadiindeno[1,2-a;1',2'-c]fluorene trioxime tri-O-acetate (shown below) was performed similarly to Example 1.11 with the exception that acetyl chloride was replaced with hexanoyl chloride in step (b).

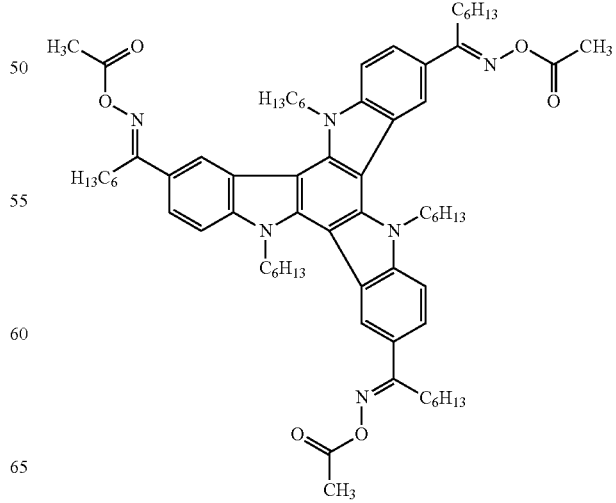

3,8,13-Trihexanoyl-5,10,15-trihexyl-10,15-dihydro-5H-5,10,15-triazadiindeno[1,2-a; 1',2'-c]fluorene trioxime tri-O-acetate was obtained as a white solid product with a 28% overall yield.

$^1$H NMR (500 MHz, CDCl$_3$) δ: 8.69 (s, 3H), 7.83 (d, J=8.4 Hz, 3H), 7.67 (d, J=8.7 Hz, 3H), 5.00 (t, J=7.1 Hz, 6H), 3.05 (t, J=7.8 Hz, 6H), 2.35 (s, 9H), 1.95 (p, J=7.1 Hz, 6H), 1.72 (p, J=7.6 Hz, 6H), 1.50-1.44 (m, 6H), 1.41 (p, J=7.4 Hz, 6H), 1.25-1.13 (m, 18H), 0.94 (t, J=7.3 Hz, 9H), 0.76 (t, J=7.1 Hz, 9H).

Figure 12:
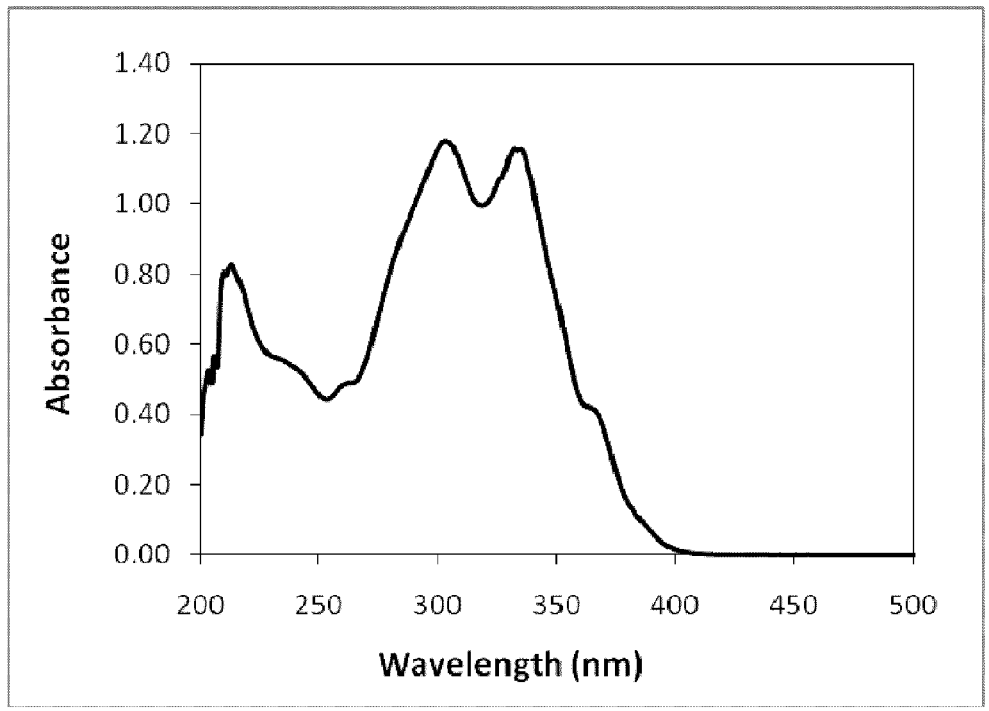
FIG. 12 shows the UV-Vis spectrum of 3,8,13-triacetyl-5,10,15-trihexyl-10,15-dihydro-5H-5,10,15-triazadiindeno[1,2-a;1',2'-c]fluorene trioxime tri-O-acetate.

The UV-Vis spectrum of 3,8,13-Triacetyl-5,10,15-trihexyl-10,15-dihydro-5H-5,10,15-triazadiindeno[1,2-a;1',2'-c]fluorene trioxime tri-O-acetate is shown in FIG. 12. This spectrum shows strong absorption bands between 300 and 400 nm. More particularly, the spectrum shows a strong absorption at 365 nm followed by a sharp decline. This enhances sensitivity, while avoiding color interference.

Example 1.15

2,7,12-Tri(4-acetylphenyl)-5,5,10,10,15,15-hexahexyl-10,15-dihydro-5H-diindeno[1,2-a;1',2'-c]fluorene trioxime tri-O-acetate (a) Synthesis of 2,7,12-Tri(4-acetylphenyl)-5,5,10,10,15,15-hexahexyl-10,15-dihydro-5H-diindeno[1,2-a;1',2'-c]fluorene trioxime In a 100 mL 3-necks flask, 2,7,12-tri(4-acetylphenyl)-5,5',10,10',15,15'-hexahexyltruxene (6 g) was dissolved in dioxane (50 mL) under nitrogen. A solution of hydroxylammonium chloride (346 mg) and sodium acetate (329 mg) in water (15 mL) was added to this solution. The reaction mixture was refluxed for 12 h. The reaction was monitored by TLC using 5% ethyl acetate in toluene. The solvent was evaporated under reduced pressure. Then water (250 mL) was added and the compound was filtered off to afford a sticky solid. The product was purified by recrystallization in methanol and left at −20° C. overnight. The compound (shown below) was filtered to afford 4 g (65%) of a white powder.

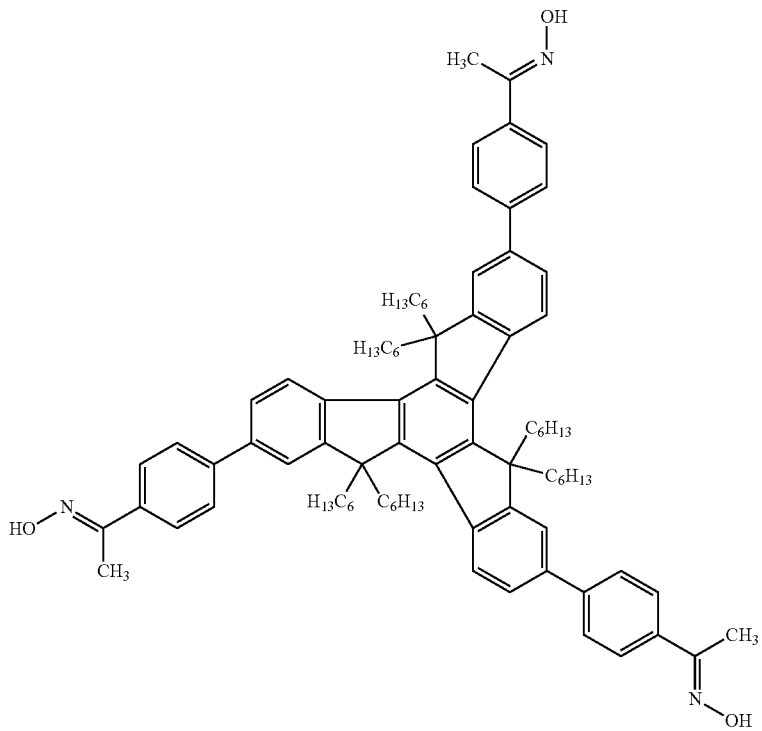

$^1$H NMR (500 MHz, CDCl$_3$) δ 8.52-8.50 (m, 3H); 8.03-7.94 (m, 6H); 7.91-7.85 (m, 6H); 7.79-7.73 (m, 6H); 3.05 (s, 6H); 2.71 (s, 9H); 2.22 (s, 6H); 0.96-0.90 (m, 36H); 0.63-0.61 (m, 30H).

(b) 2,7,12-Tri(4-acetylphenyl)-5,5,10,10,15,15-hexahexyl-10,15-dihydro-5H-diindeno[1,2-a;1',2'-c]fluorene trioxime tri-O-acetate In a flame dried 1 L 3-neck flask was added dry tetrahydrofuran and 2,7,12-Tri(4-acetylphenyl)-5,5,10,10,15,15-hexahexyl-10,15-dihydro-5H-diindeno[1,2-a;1',2'-c]fluorene trioxime (3 g) under nitrogen. The reaction was allowed to cool down to 0° C. in an ice bath before the addition of triethylamine (1.1 mL). The reaction was stirred for 5 min before the slow addition of acetyl chloride (0.591 mL). The reaction was stirred 2 h at 0° C. and monitored on TLC using 5% ethyl acetate in toluene as eluent. The reaction mixture was extracted in ethyl acetate and water, dried over magnesium sulphate and the solvent evaporated under reduced pressure. Then methanol (500 mL) was added to the crude product and the solution was heated and filtered. The crude product was dissolved in 2-propanol, the solution was heated, and left at −20° C. for 1 h then filtered to afford 2 g (60%) of a white powder.

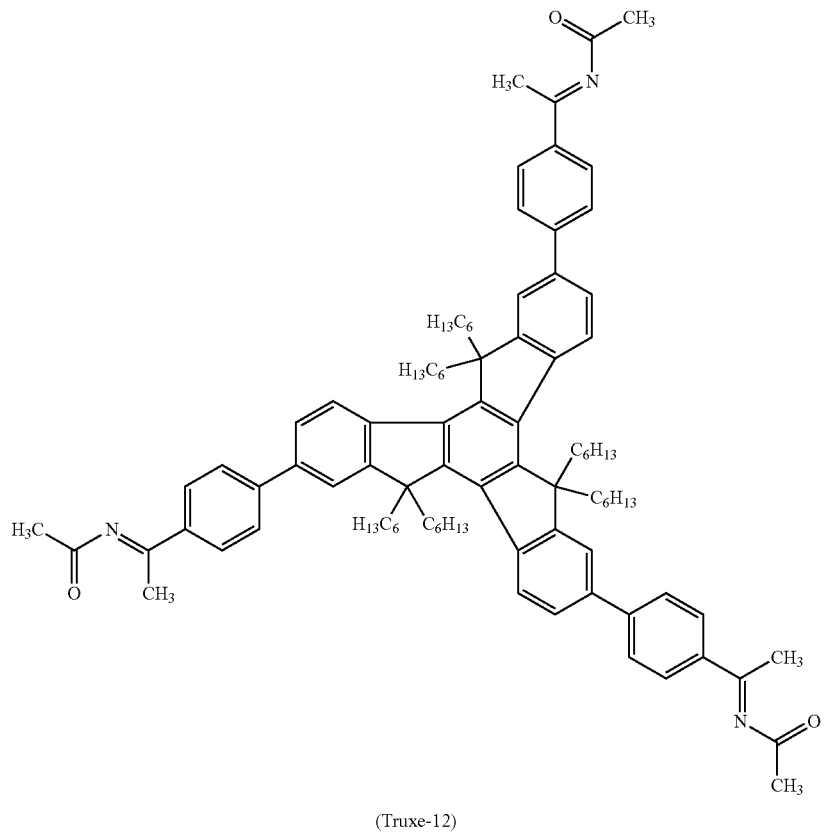

(Truxe-12)

$^1$H NMR (500 MHz, CDCl$_3$) δ 8.48 (d, J=8.4 Hz, 3H); 7.94 (d, J=8.6 Hz, 6H); 7.84 (d, J=8.6 Hz, 6H); 7.74-7.72 (m, 6H); 3.08-3.01 (m, 6H); 2.50 (s, 9H); 2.34 (s, 9H) 2.24-2.15 (m, 6H); 1.03-0.85 (m, 36H); 0.64-0.58 (m, 30H).

UV-Vis (THF): 338 nm. DSC: 124° C. IR (KBr): 2955, 2924, 2855, 1772, 1603, 1478, 1364, 1318, 1199, 984, 933, 890, 830, 808.

Figure 13:
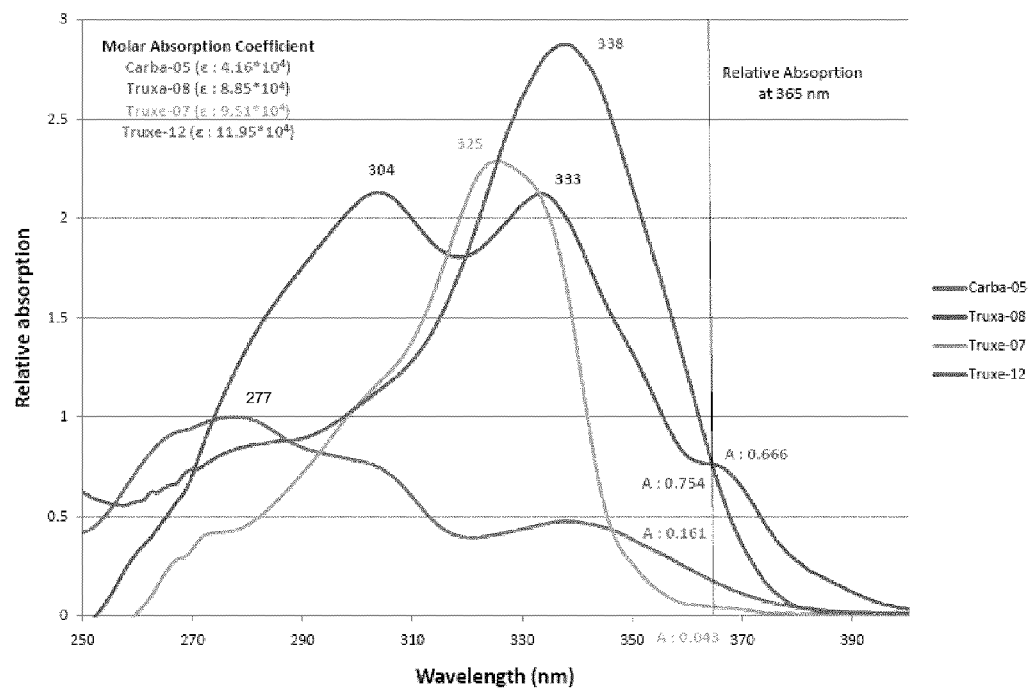
FIG. 13 shows the UV-Vis spectra of Carba-05, Truxe-08, Truxe-07 and Truxe-12.
Figure 14:
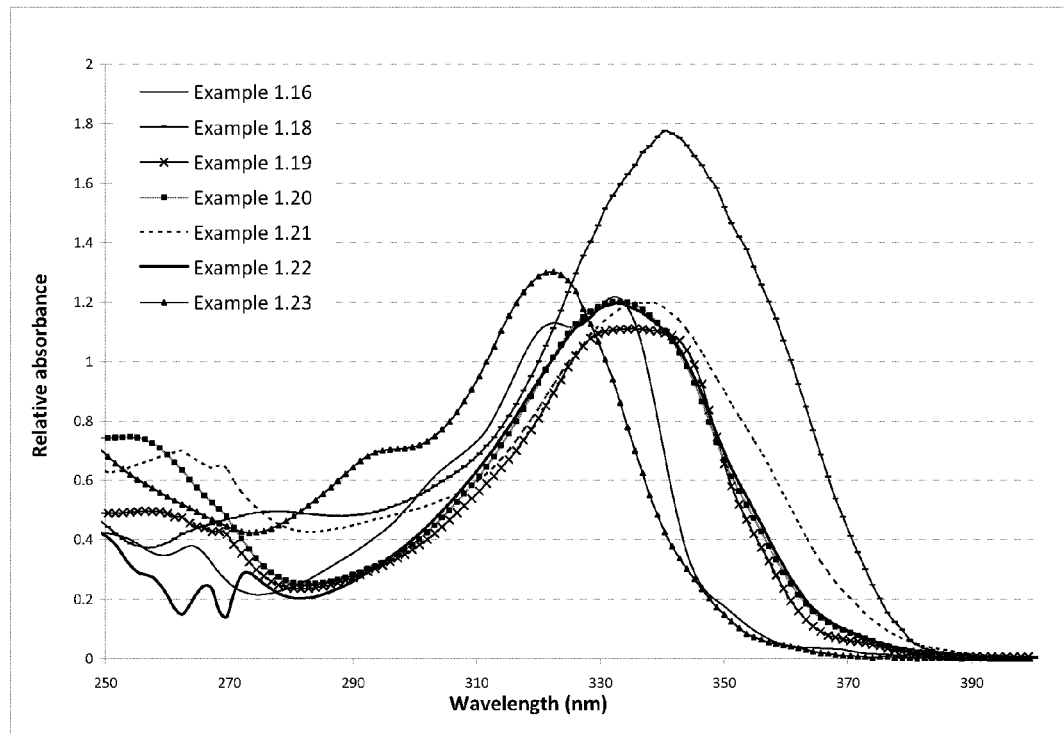
FIG. 14 shows the relative UV-Vis absorbance of Truxe-04 (INDENO 332), Truxe-13 (INDENO 336), Truxe-14 (INDENO 332B), Truxe-15 (INDENO 338) and Truxe-16 (INDENO 333)

FIG. 13 shows the UV spectra of Carba-05 (which is Irgacure OXE-02 from BASF), Truxe-08 and Truxe-07 (from above), and Truxe-12 (from Example 1.15). The spectra have been normalized so that the maximum absorption of Carba-05 is 1. In this figure, Carba-05 is the curve with a maximum absorption at 277 nm and a relative absorption at 365 nm or 0.161. Truxe-08 has two absorption peaks at 304 and 333 nm with a relative absorption at 365 nm of 0.754. Truxe-07 has one absorption peak at 325 nm and a relative absorption at 365 nm of 0.043. Finally, Truxe-12 has an absorption peak at 338 nm and a relative absorption at 365 nm of 0.666. It should be noted that Truxe-12 has a higher absorption than OXE-02.

Example 1.16

2,7,12-triacetyl-5,5',10,10',15,15'-hexahexyltruxene (INDENO 332)

The synthesis of 2,7,12-triacetyl-5,5',10,10',15,15'-hexahexyltruxene was effected by dissolving 4.3 grams of 5,5',10,10',15,15'-hexahexyltruxene in a 250 mL flame dried flask containing 50 mL of dichloromethane under N$_2$. Acetyl chloride (1.83 mL) was added, and then aluminum chloride (3.27 g) was slowly added over a period of 15 minutes. The reaction mixture was stirred at room temperature overnight. The reaction was monitored by TLC using 2.5% EtOAc in toluene as eluent. An extraction was performed using dichloromethane and water. The mixture was then dried over magnesium sulfate. The crude product was carefully dried under high vacuum, precipitated in methanol and then filtered to afford an off white powder (5.5 g, 72%).

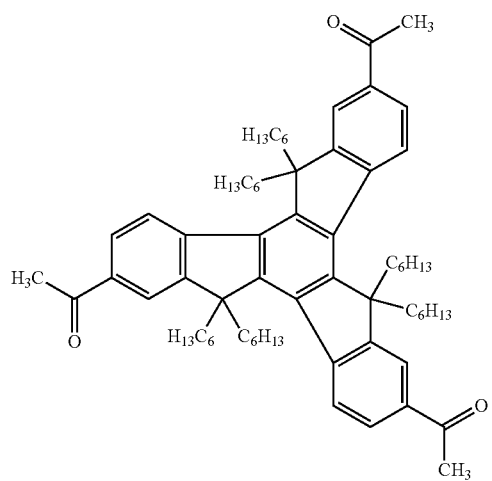

H$^1$NMR (500 MHz, CDCl$_3$) δ 8.49 (d, J=8.4 Hz, 3H); 8.12 (d, J=1.7 Hz, 3H); 8.07 (dd, J1=1.7, J2=8.3 Hz, 3H); 3.00 2.94 (m, 6H); 2.76 (s, 9H); 2.25 2.19 (m, 6H); 0.98 0.79 (m, 36H); 0.61 (t, J=7.1, 18H); 0.52 0.44 (m, 12H).

The maximum absorption peak and absorption coefficient of 2,7,12-triacetyl-5,5',10,10',15,15'-hexahexyltruxene in tetrahydrofuran solution are 332 nm and $8.66 \times 10^4$ L/mol·cm, respectively. The melting point was measured to be 217° C. by DSC.

Example 1.17

3,8,13-triacetyl-5,10,15-trihexyl-10,15-dihydro-5H-5,10,15-triazadiindeno[1,2-a;1',2'-c]-fluorene (INDENO 336)

The synthesis of 3,8,13-triacetyl-5,10,15-trihexyl-10,15-dihydro-5H-5,10,15-triazadiindeno[1,2-a;1',2'-c]-fluorene was done by slowly adding aluminum trichloride (1.47 g, 11.02 mmol) into a solution containing dichloromethane (10 mL) and 5,10,15-trihexyl-10,15-dihydro-5H-5,10,15-triazadiindeno[1,2-a;1',2'-c]fluorene (2 g, 3.35 mmol). The solution turned dark red. Then, acetyl chloride (750 μL, 14.75 mmol) of was added dropwise over a period of 2 minutes. The reaction was monitored by TLC using a mixture of ethyl acetate (30%) and hexane (70%) as an eluent. After the reaction was completed, the reaction mixture was quickly filtered and concentrated under vacuum to obtain a sticky red product. Anhydrous ethanol (15 mL) was added to form a slurry, which was placed in a sonic bath for 30 minutes. The solid product was filtered, copiously washed with ethanol and dried under high vacuum at 30° C. overnight to afford a pale red solid (1.93 g, 80% yield).

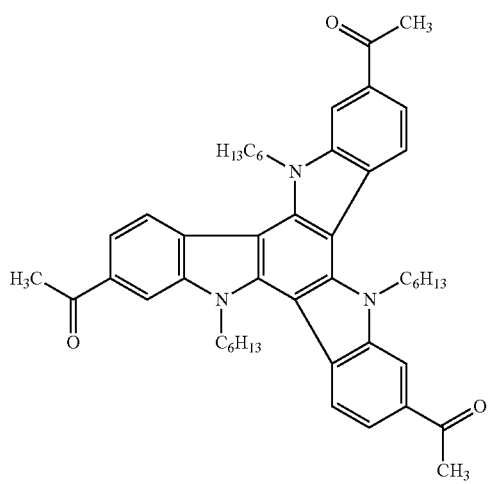

$^1$H NMR (500 MHz, CDCl$_3$) δ 9.02 (s, 3H), 8.13 (d, J=8.6 Hz, 3H), 7.66 (d, J=8.5 Hz, 3H), 5.00 (t, J=7.7 Hz, 6H), 2.80 (s, 9H), 1.99 (p, J=7.6 Hz, 6H), 1.33 (p, J=7.3 Hz, 6H), 1.26-1.17 (m, 12H), 0.78 (t, J=7.1 Hz, 9H).

The maximum absorption peak and absorption coefficient of 3,8,13-triacetyl-5,10,15-trihexyl-10,15-dihydro-5H-5,10,15-triazadiindeno[1,2-a;1',2'-c]fluorene in tetrahydrofuran solution are 336 nm and $7.40 \times 10^4$ L mol$^{-1}$ cm$^{-1}$, respectively.

Example 1.18

2,7,12-tri(4-acetylphenyl)-5,5',10,10',15,15'-hexahexyltruxene

TRUXE 03 (8.5 g), 4-acetylphenylboronic acid (4.2 g) and toluene (500 mL) were introduced in a 500 mL flask, flushed with nitrogen. Potassium carbonate (28 g) dissolved in water (100 mL) was added to this mixture. The reaction mixture was bubbled with nitrogen for 30 min. Then, palladium acetate (52 mg) and triphenylphosphine (62 mg) were added to the solution. The reaction mixture was heated at reflux for 2 days before adding 4-acetylphenylboronic acid (4.2 g). The reaction was once again refluxed for 2 days before the final addition of 4-acetylphenylboronic acid (4.2 g). The reaction was then refluxed for 4 days. The reaction was monitored using 100% toluene as eluent. The reaction mixture was washed three times with water, dried over magnesium sulphate and concentrated under reduced pressure. The mixture was quickly passed over a silica gel pad using 100% toluene as eluent to afford 7 g (75%) of the desired product.

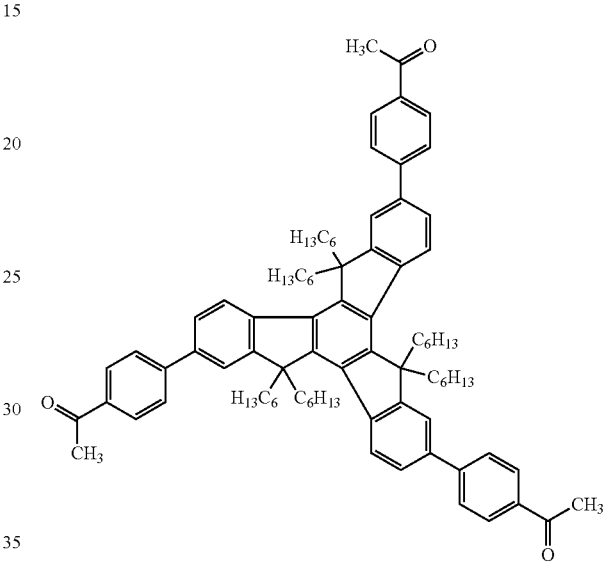

$^1$H NMR (500 MHz, CDCl$_3$) δ 8.50 (d, J=8.3 Hz, 3H); 8.14 (d, J=8.6 Hz, 6H); 7.89 (d, J=8.5 Hz, 6H); 7.77-7.75 (m, 6H); 3.08-3.02 (m, 6H); 2.72 (s, 9H); 2.25-2.19 (m, 6H); 1.05-0.85 (m, 36H); 0.64-0.58 (m, 30H).

The maximum absorption peak and absorption coefficient of 2C in tetrahydrofuran solution are 340 nm and $12.64 \times 10^4$ L mol$^{-1}$ cm$^{-1}$, respectively. The melting point is 85° C.

Example 1.19

2,7,12-tri-(o-toluloyl)-5,5',10,10',15,15'-hexahexyl-truxene (INDENO 337)

5,5',10,10',15,15'-Hexahexyltruxene (1.1 g) was dissolved in 10 mL of CH$_2$Cl$_2$ in a 100 mL flask under N$_2$. o-Toluloyl chloride (638 mg, 3.20 eq) was added, and then aluminium chloride (525 mg, 3.05 eq) was added slowly over a period of 15 minutes. The reaction mixture was stirred at room temperature overnight. The reaction was monitored by TLC using 100% toluene as eluent. If necessary, aluminium chloride (130 mg, 0.76 eq) and o-toluloyl chloride (160 mg, 0.80 eq) were added to the reaction mixture and the reaction was stirred at room temperature overnight. The reaction was quenched by the careful and slow addition of water. An extraction was performed using CH$_2$Cl$_2$ and water. The mixture was then dried over MgSO$_4$. The crude product was purified on a silica gel column using 50% hexanes in toluene to 100% toluene. The resulting thick oil was triturated in methanol and filtered to afford a light yellow powder (720 mg, 46%).

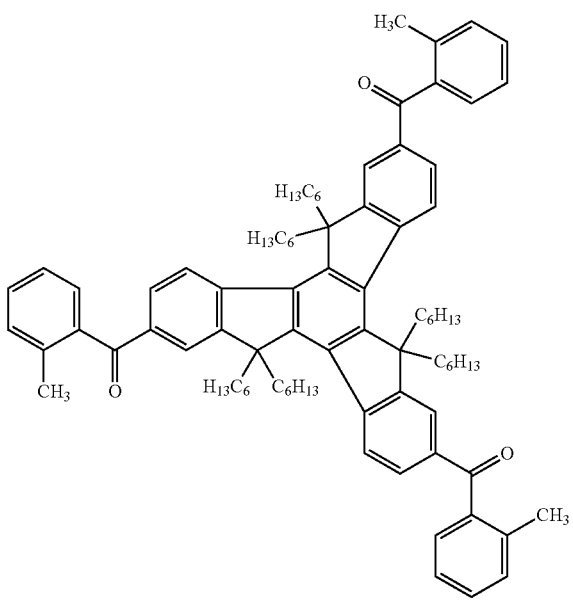

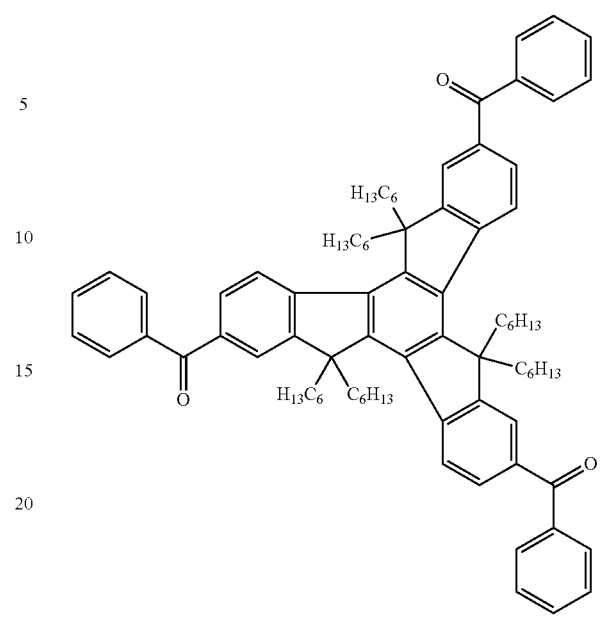

$^1$H NMR (500 MHz, CDCl$_3$) δ 8.42 (d, J=8.4 Hz, 3H), 7.99 (d, J=1.5 Hz, 3H), 7.80 (dd, J$_1$=1.4 Hz, J$_2$=8.3 Hz, 3H), 7.47-7.41 (m, 6H), 7.35 (d, J=7.6 Hz, 3H), 7.31 (t, J=7.4 Hz, 3H), 2.95-2.86 (m, 6H), 2.40 (s, 9H), 2.17-2.09 (m, 6H), 0.97-0.79 (m, 36H), 0.61 (t, J=7.0 Hz, 18H), 0.53-0.44 (m, 12H).

The maximum absorption peak and absorption coefficient of 2,7,12-tri-(o-tuluoyl)-5,5',10,10',15,15'-hexahexyltruxene in tetrahydrofuran solution are 336 nm and 7.90×10$^4$ L mol$^{-1}$ cm$^{-1}$, respectively. The melting point is 125° C.

Example 1.20

2,7,12-Tri-(phenoyl)-5,5',10,10',15,15'-hexahexyltruxene (INDENO 333)

5,5',10,10',15,15'-Hexahexyltruxene (5.0 g) was dissolved in 50 mL of CH$_2$Cl$_2$ in a 100 mL flask under N$_2$. Benzoyl chloride (2.6 g, 3.20 eq) was added, and then aluminium chloride (3.3 g, 3.05 eq) was slowly added over a period of 5 minutes. The reaction mixture was stirred at room temperature for two days. The reaction was monitored by HPLC (peak at 8 min.) and TLC using 100% toluene as eluent. If necessary, aluminium chloride (825 mg, 0.76 eq) and benzoyl chloride (650 mg, 0.80 eq) were added to the reaction mixture and the reaction was stirred at room temperature overnight. The reaction was quenched by the careful and slow addition of water (WARNING: highly exothermic). An extraction was performed using CH$_2$Cl$_2$ and water. The organic layer was washed with a 1M solution of NaHCO$_3$ and then dried over MgSO$_4$. The solution was concentrated under reduced pressure. The resulting tarry solid was triturated in methanol for 1 h and filtered. After filtration, the crude product was recrystallized from 2-propanol to afford 3.3 g (48%, 100%: 6.84 g). Further purification, when desired, was achieved on a silica gel column using 50% hexanes in toluene to 100% toluene (started with 500 mg, recovered 60 mg, 12%).

$^1$H NMR (500 MHz, CDCl$_3$) δ 8.48 (d, J=8.4 Hz, 3H), 7.96 (d, J=1.6 Hz, 3H), 7.93-7.88 (m, 9H), 7.65 (tt, J$_1$=7.5 Hz, J$_2$=1.3 Hz, 3H), 7.55 (t, J=7.7 Hz, 6H), 3.00-2.92 (m, 6H), 2.21-2.13 (m, 6H), 1.00-0.83 (m, 36H), 0.63 (t, J=7.3 Hz, 18H), 0.58-0.50 (m, 12H).

The maximum absorption peak and absorption coefficient of 2,7,12-tri-(phenoyl)-5,5',10,10',15,15'-hexahexyltruxene in tetrahydrofuran solution are 332 nm and 8.55×10$^4$ L mol$^{-1}$ cm$^{-1}$, respectively. The melting point is 155° C.

Example 1.21

2,7,12-tri-(2-thienyloyl)-5,5',10,10',15,15'-hexahexyltruxene 5,5',10,10',15,15'-Hexahexyltruxene (5.0 g) was dissolved in 50 mL of CH$_2$Cl$_2$ in a 100 mL flask under N$_2$. 2-thiophenecarbonyl chloride (2.8 g, 3.20 eq) was added, and then aluminium chloride (3.3 g, 3.05 eq) was slowly added over a period of 5 minutes. The reaction mixture was stirred at room temperature for two days. The reaction was monitored by HPLC (peak at 5 min.) and TLC using 100% toluene as eluent. If necessary, aluminium chloride (825 mg, 0.76 eq) and 2-thiophenecarbonyl chloride (700 mg, 0.80 eq) were added to the reaction mixture and the reaction was stirred at room temperature overnight. The reaction was quenched by the careful and slow addition of water (WARNING: highly exothermic). An extraction was performed using CH$_2$Cl$_2$ and water. The organic layer was washed with a 1M solution of NaHCO$_3$ and then dried over MgSO$_4$. The solution was concentrated under reduced pressure. The resulting tarry solid was triturated in methanol for 1 h and filtered. After filtration, the crude product was recrystallized from 2-propanol to afford 580 mg (8%, 100%: 6.95 g) of a compound suitable for analysis and 1.6 g (23%) of acceptably pure compound. Both fractions showed only one peak by HPLC but the 1.6 g fraction showed a small impurity on TLC.

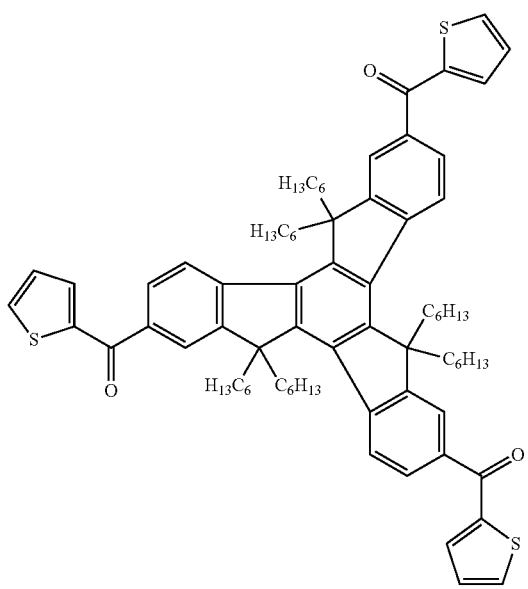

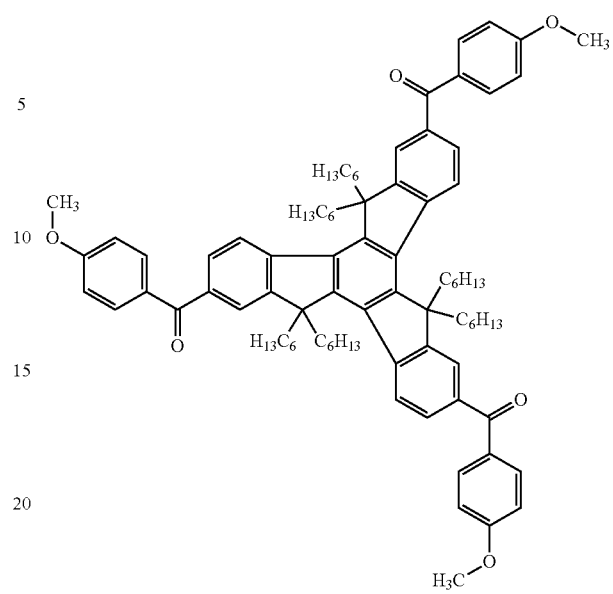

¹H NMR (500 MHz, CDCl₃) δ 8.51 (d, J=8.2 Hz, 3H), 8.03-7.99 (m, 6H), 7.78 (dd, $J_1$=4.9 Hz, $J_2$=1.1 Hz, 3H), 7.77 (dd, $J_1$=3.8 Hz, $J_2$=1.1 Hz, 3H), 7.24 (dd, $J_1$=4.8 Hz, $J_2$=3.8 Hz, 3H), 3.00-2.95 (m, 6H), 2.24-2.17 (m, 6H), 1.01-0.82 (m, 36H), 0.62 (t, J=7.0 Hz, 18H), 0.58-0.49 (m, 12H).

The maximum absorption peak and absorption coefficient of 2,7,12-tri-(2-thienyloyl)-5,5',10,10',15,15'-hexahexyltruxene in tetrahydrofuran solution are 338 nm and 8.53×10⁴ L mol⁻¹ cm⁻¹, respectively. The melting point is 125° C.

Example 1.22

2,7,12-tri-(4-methoxyphenyloyl)-5,5',10,10',15,15'-hexahexyltruxene 5,5',10,10',15,15'-Hexahexyltruxene (5.0 g) was dissolved in 50 mL of CH₂Cl₂ in a 100 mL flask under N₂. 3-methoxybenzyol chloride (3.2 g, 3.20 eq) was added, and then aluminium chloride (3.3 g, 3.05 eq) was slowly added over a period of 5 minutes. The reaction mixture was stirred at room temperature for two days. The reaction was monitored by HPLC (peak at 6 min.) and TLC using 2% ethyl acetate in toluene as eluent. If necessary, aluminium chloride (825 mg, 0.76 eq) and 3-methoxybenzyol chloride (800 mg, 0.80 eq) were added to the reaction mixture and the reaction was stirred at room temperature overnight. The reaction was quenched by the careful and slow addition of water (WARNING: highly exothermic). An extraction was performed using CH₂Cl₂ and water. The organic layer was washed with a 1M solution of NaHCO₃ then dried over MgSO₄. The solution was concentrated under reduced pressure. The resulting tarry solid was triturated in methanol for 1 h and filtered. After filtration, the crude product was recrystallized from 2-propanol to afford 700 mg (9%, 100%: 7.37 g). Further purification, when desired, was achieved on a silica gel column using 100% toluene to 10% ethyl acetate in toluene (recovered 30 mg).

¹H NMR (500 MHz, CDCl₃) δ 8.48 (d, J=8.4 Hz, 3H), 7.95 (d, $J_1$=1.5 Hz, 3H), 7.93 (dd, $J_1$=8.3 Hz, $J_2$=1.6 Hz, 3H), 7.46-7.42 (m, 9H), 7.21-7.18 (m, 3H), 3.91 (s, 9H), 3.00-2.93 (m, 6H), 2.20-2.13 (m, 6H), 1.00-0.82 (m, 36H) 0.63 (t, J=7.0 Hz, 18H), 0.59-0.48 (m, 12H).

The maximum absorption peak and absorption coefficient of 2,7,12-tri-(4-methoxyphenyloyl)-5,5',10,10',15,15'-hexahexyltruxene in tetrahydrofuran solution are 333 nm and 8.55×10⁴ L mol⁻¹ cm⁻¹, respectively. The melting point is 137° C.

Example 1.23

2,7,12 tri-(2-acetylphenyl)-5,5',10,10',15,15'hexahexyltruxene 2,7,12-tribromo-5,5',10,10',15,15'-hexahexyltruxene (1.7 g), 2-acetylphenylboronic acid (0.84 g) and toluene (100 mL) were introduced in a 500 mL flask, flushed with nitrogen. Sodium carbonate (5.6 g) dissolved in water (20 mL) and tetrabutylammonium bromide (100 mg) were added to this mixture. The reaction mixture was bubbled with nitrogen for 30 min. Then, palladium acetate (48 mg) and triphenylphosphine (60 mg) were added to the solution. The reaction mixture was heated at reflux for 2 days. The reaction mixture was washed with water three times, dried over magnesium sulphate and concentrated under reduced pressure. The mixture was quickly passed over a silica gel using 100% toluene, then 1 to 3% acetone in toluene as eluent to afford 500 mg (27%) of the desired product.

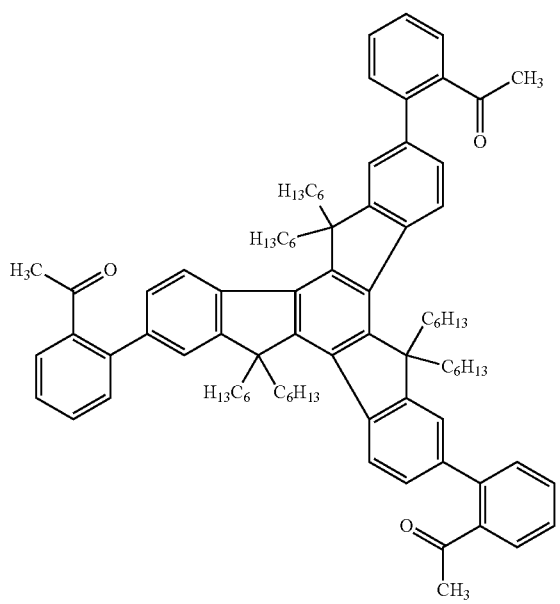

$^1$H NMR (500 MHz, CDCl$_3$) δ 8.42 (d, J=8.2 Hz, 3H), 7.61-7.55 (m, 9H), 7.48-7.45 (m, 6H), 7.42 (dd, J1=8.2 Hz, J2=1.7 Hz, 3H), 3.04-2.96 (m, 6H), 2.15-2.07 (m, 6H), 2.01 (s, 9H), 1.00-0.80 (m, 36H), 0.60 (t, J=7.3 Hz, 18H), 0.58-0.52 (m, 12H).

The maximum absorption peak and absorption coefficient of 2,7,12-tri-(2-acetylphenyl)-5,5',10,10',15,15'-hexahexyl-truxene in tetrahydrofuran solution are 323 nm and 9.20×10$^4$ L mol$^{-1}$ cm$^{-1}$, respectively. The melting point is 136° C.

FIG. 13 shows the relative UV-Vis absorbance of the photoinitiators of Examples 1.16 and 1.18 to 1.23.

Red, Green, Blue and Black Color Filter Resists

Examples 2.1 to 2.10 and Comparative Example 1

Red, green, and blue color filter resists and black matrix with different photoinitiators were prepared by mixing 1.0 part of photoinitiators, 13 parts of resist vehicles, 6.0 parts of the corresponding pigment dispersions, i.e., Red-254, Green-36, Blue-15 and Black-250, respectively, using a high shear mixer for 2 hours. The resulting mixtures were filtered through a 1 μm pore filter. The pigmented solutions were coated on glass using a spin coater, dried at 100° C. for 2 minutes to produce uniform films having a thickness around 3 μm.

The color resist films were exposed using a 250 W super high pressure mercury lamp under air with a dose of 1,000 mJ/cm$^2$ through a 21-gray-scale step target mask (Stouffer Graphic Arts T2115). The exposed films were developed using aqueous potassium hydroxide solution (pH 12), washed copiously with de-ionized water, and then dried at 100° C. for 30 minutes. The results are summarized in the table below.

| Examples | Photoinitiators | Sensitivity (mJ/cm$^2$) | | | |
| --- | --- | --- | --- | --- | --- |
| | | Red | Green | Blue | Black |
| 2.1 | Example 1.1 | 32 | 82 | 90 | 107 |
| 2.2 | Example 1.2 | 32 | 82 | 90 | 107 |
| 2.3 | Example 1.3 | 36 | 89 | 97 | 120 |
| 2.4 | Example 1.4 | 38 | 91 | 105 | 115 |
| 2.5 | Example 1.5 | 28 | 74 | 89 | 107 |
| 2.6 | Example 1.6 | 18 | 42 | 51 | 65 |
| 2.7 | Example 1.7 | 12 | 37 | 42 | 49 |
| 2.8 | Example 1.8 | 18 | 46 | 54 | 67 |
| 2.9 | Example 1.9 | 39 | 94 | 98 | 117 |
| 2.10 | Example 1.10 | 15 | 41 | 49 | 57 |
| Comparative Example 1 | Irgacure OXE-2 | 34 | 86 | 98 | 115 |

In this table, the value reported for the sensitivity is the minimum dose required to fully cure the color resist films. It was calculated from the transmittance of the highest step number remaining after development. It is desirable that the minimum dose (mJ/cm$^2$) required be as small as possible, which indicates a highly sensitive compound. Generally, the more sensitive the photoinitiator, the less time it takes to cure the composition.

It can be seen from the above table that the compounds of the invention are about as sensitive as Irgacure OXE-2 and sometimes even more sensitive.

Examples 2.11 to 2.18 and Comparative Examples (CE) 2 to 5

Red, green, blue and black color resists were prepared by mixing the pigment dispersion, resist vehicle and the photoinitiators of Examples 1.11 and 1.12 using a high shear mixer for 2 hours. The resulting mixture was filtered through a 1 μm pore filter. The pigmented solutions were coated on glass using spin coater, dried at 100° C. for 2 minutes to produce a uniform film having a thickness around 3 μm. For comparison, commercially available photoinitiator, Irgacure OXE-02 was also used.

The color resist films were exposed using a 250 W super high pressure mercury lamp under air with a dose of 1,000 mJ/cm$^2$ through a 21-gray-scale step target mask (Stouffer Graphic Arts T2115). The exposed films were developed using aqueous potassium hydroxide solution (pH 12), copiously washed with de-ionized water, and then dried at 100° C. for 30 minutes. The results are summarized in the table below.

In this table, the value reported for photosensitivity is the minimum dose required to fully cure the color resist films. It was calculated from the transmittance of the highest step number remaining after development. It is desirable that the minimum dose (mJ/cm$^2$) required be as small as possible, which indicates a highly sensitive compound. Generally, the more sensitive the photoinitiator, the less time it takes to cure the composition.

| Ingredients | EXAMPLES (Solid weight in grams) | | | | | | | | | | | |
|---|---|---|---|---|---|---|---|---|---|---|---|---|
| | 2.11 | 2.12 | CE 2 | 2.13 | 2.14 | CE 3 | 2.15 | 2.16 | CE 4 | 2.17 | 2.18 | CE 5 |
| Red-254 | 6.0 | 6.0 | 6.0 | | | | | | | | | |
| Green-30 | | | | 5.0 | 5.0 | 5.0 | | | | | | |
| Yellow-150 | | | | 1.0 | 1.0 | 1.0 | | | | | | |
| Blue-15 | | | | | | | 6.0 | 6.0 | 6.0 | | | |
| Black-250 | | | | | | | | | | 6.0 | 6.0 | 6.0 |
| Resist vehicle | 13.0 | 13.0 | 13.0 | 13.0 | 13.0 | 13.0 | 13.0 | 13.0 | 13.0 | 13.0 | 13.0 | 13.0 |
| Photoinitiator of Example 1.11 | 1.0 | | | 1.0 | | | 1.0 | | | 1.0 | | |
| Photoinitiator of Example 1.12 | | 1.0 | | | 1.0 | | | 1.0 | | | 1.0 | |
| Irgacure® OXE02 | | | 1.0 | | | 1.0 | | | 1.0 | | | 1.0 |
| Sensitivity (mJ/cm$^2$) | 29 | 25 | 34 | 74 | 67 | 86 | 83 | 75 | 98 | 97 | 86 | 115 |

As can be seen from the above, the compounds of the invention tested are, in all cases, more senstive that Irgacure OXE-02

Lithographic Offset Printing Plates

Example 3.1

A coating composition was prepared by mixing 250 g of BR10-010, 67 g of UR07-009, 1.0 g of basic green 4, 33 g of Blue-15, and 5.0 g of photoinitiator from Example 1.7, and 900 g of cyclohexanone solution using a high shear mixer for 5 hours. The resulted solution was filtered through a 5 μm pore filter. It was coated on an anodized aluminum substrate, which was postreated with phosphate fluoride (PF) using a wire-wound rod, then dried in a hot air oven at 100° C. for 5 minutes.

The plate was exposed using a 250 W super high pressure mercury lamp under air with an energy density of 100 mJ/cm$^2$ through a 21-gray-scale step target mask (Stouffer Graphic Arts T2115). The exposed plate was developed with aqueous solution containing 1% soap solution using a Tung Sung 800 processor at 25° C. and 20 seconds dwell time to give a high resolution image.

The developed plate was placed on a Heidelberg 46 press using black ink (Toyo Black) and fountain solution (UF300, available from Mylan Group, Vietnam) and produced 20,000 copies with good quality.

Example 3.2

A printing plate was prepared in a manner similar to that described in Example 3.1 excepted that the photoinitiator from Example 1.10 was used to replace the photoinitiator from Example 1.7.

The plate was exposed using a 250 W super high pressure mercury lamp under air with an energy density of 100 mJ/cm$^2$ through a 21-gray-scale step target mask (Stouffer Graphic Arts T2115). The exposed plate was developed with aqueous solution containing 1% soap solution using a Tung Sung 800 processor at 25° C. and 20 seconds dwell time to give high resolution image.

The developed plate was placed on a Heidelberg 46 press using black ink (Toyo Black) and fountain solution (UF300, available from Mylan Group, Vietnam) and produced 20,000 copies with good quality

Example 3.3

A coating composition was prepared by mixing 250 g of BR10-010, 67 g of UR07-009, 1.0 g of basic green 4, 33 g of Blue-15, and 5.0 g of photoinitiators 1E (Example 1.11) and 900 g of 2-methoxypropanol solution using a high shear mixer for 5 hours. The resulted solution was filtered through a 5 μm pore filter. It was coated on an anodized aluminum substrate, which was postreated with phosphate fluoride (PF) using a wire-wound rod, then dried in a hot air oven at 100° C. for 5 minutes.

The plate was exposed using a 250 W super high pressure mercury lamp under air with an energy density of 100 mJ/cm$^2$ through a 21-gray-scale step target mask (Stouffer Graphic Arts T2115). The exposed plate was developed with aqueous solution containing 1% Mr. Clean soap solution using a Tung Sung 800 processor at 25° C. and 20 seconds dwell time to give high resolution image.

The developed plate was placed on a Heidelberg 46 press using black ink (Toyo Black) and fountain solution (UF300, available from Mylan Group, Vietnam) to produce 20,000 copies with good quality.

Example 3.4

The printing plate was prepared similar to Example 3.3 except that the photoinitiator from Example 1.12 was used instead of that of Example 1.11.

The plate was exposed using a 250 W super high pressure mercury lamp under air with an energy density of 100 mJ/cm$^2$ through a 21-gray-scale step target mask (Stouffer Graphic Arts T2115). The exposed plate was developed with aqueous solution containing 1% Mr. Clean soap solution using a Tung Sung 800 processor at 25° C. and 20 seconds dwell time to give high resolution image.

The developed plate was placed on a Heidelberg 46 press using black ink (Toyo Black) and fountain solution (UF300, available from Mylan Group, Vietnam) to produce 20,000 copies with good quality.

Uv Curable Inkjet Printing Inks

Examples 4.1 to 4.4

Ultra-violet radiation curable inkjet printing inks having the compositions shown in the table below were prepared by using a high shear mixer to form uniform solutions. These solutions were filtered through a 1.0 μm propylene filter. The filtered inks were printed on polyester films with different testing patterns and 300 DPI resolution using the Richol G4 print heads, which were jetted at 50° C. The printed patterns were cured with a UV-LED curing unit (Model: 8 Watt/cm$^2$ Fireline, available from Phoseon Technology, Oregon, USA) at a speed of ten meter per minute. The UV-LED curing unit was placed 5 cm about the printed films. Fully cured printing patterns from inkjet inks comprising the invented photoinitiators were obtained with high resolution and good adhesion to the polyester substrate.

| Ingredients | EXAMPLES (gram) | | | |
|---|---|---|---|---|
| | 4.1 | 4.2 | 4.3 | 4.4 |
| ADD-2204 | 3.50 | 3.50 | 3.50 | 3.50 |
| ADD-9984 | 10.0 | 10.0 | 10.0 | 10.0 |
| ADD-9991 | 10.0 | 10.0 | 10.0 | 10.0 |
| ADD-9992 | 8.00 | 8.00 | 8.00 | 8.00 |
| ADD-9995 | 10.0 | 10.0 | 10.0 | 10.0 |
| ADD-2614 | 10.0 | 10.0 | 10.0 | 10.0 |
| POL-0138 | 2.50 | 2.50 | 2.50 | 2.50 |
| POL-1001 | 10.0 | 10.0 | 10.0 | 10.0 |
| POL-0137 | 1.00 | 1.00 | 1.00 | 1.00 |
| 600-B307 | 1.00 | 1.00 | 1.00 | 1.00 |
| COL-1829 | 8.40 | 8.40 | 8.40 | 8.40 |
| ADD-9993 | 20.6 | 20.6 | 20.6 | 20.6 |
| Photoinitiator of Example 1.16 | 5.00 | 0.00 | 0.00 | 0.00 |
| Photoinitiator of Example 1.17 | 0.00 | 5.00 | 0.00 | 0.00 |
| Photoinitiator of Example 1.21 | 0.00 | 0.00 | 5.00 | 0.00 |
| Photoinitiator of Example 1.18 | 0.00 | 0.00 | 0.00 | 5.00 |
| Total | 100 | 100 | 100 | 100 |
| Viscosity at 25° C. (cPs) | 23.6 | 23.4 | 23.2 | 23.5 |

Oxygen Scavenging Plastic Films

The oxygen scavenging activity of the polymeric films comprising photoinitiators of the invention was demonstrated by monitoring the reduction in oxygen concentration as a result of consumption of oxygen by the prepared film sample. Thus, 1.0 gram of film sample made from acetal copolymer comprising cyclohexane pendant groups (PACH-001), cobalt (II) oleate salt and a photoinitiator was placed in a glass bottle. The glass bottle was sealed with a homemade cap containing an oxygen fluorescent probe. The glass bottle was then flushed with nitrogen gas containing around 21% of oxygen. The bottle was then sealed and activated by exposure to a UV light at 254 nm at room temperature with a dosage of 100 mJ/cm$^2$. The reduction in oxygen concentration over time was monitored using an Oxysense's GEN III 5000 non-invasive oxygen monitoring and permeation system.

Example 4.1

Figure 15:
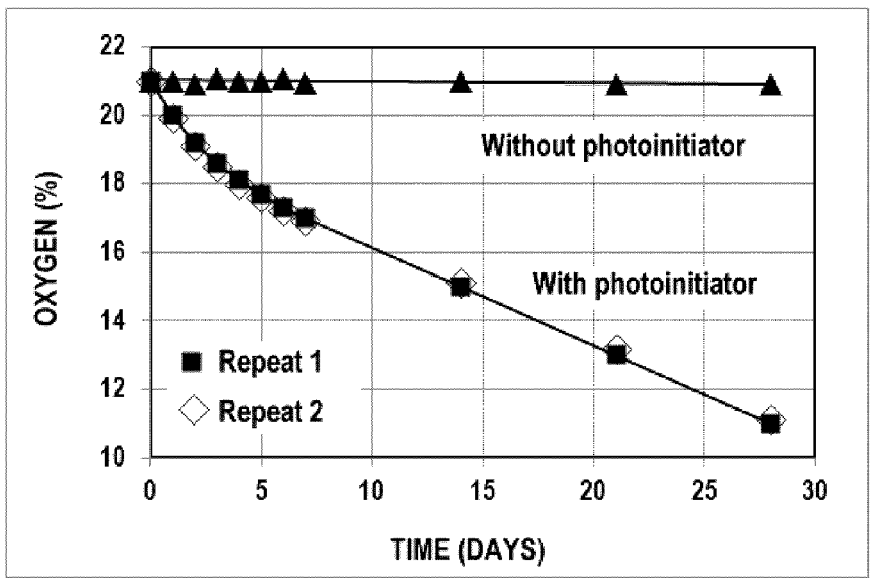
FIG. 15 shows the oxygen consumption of an oxygen scavenging film comprising INDENO 332 as a function of time.

One hundred parts of an acetal copolymer comprising cyclohexane pendant group (PACH-001) was dissolved in 1,3-dioxane to make up a 20% solution. To this solution were added 0.1 parts of cobalt (II) oleate salt and 0.1 parts of the photoinitiator of Example 1.16. When the solution became clear, it was poured onto a flat Teflon surface and the solvent was allowed to evaporate at room temperature. The obtained polymer film was further dried in a vacuum overnight, which gave an optically clear film having a thickness of around 200 μm. This film was used for the subsequent demonstration for oxygen scavenging activity. Results of the reduction of oxygen versus time are shown in FIG. 15

For comparative purposes, a similar PACH-001 film was prepared without the photoinitiator of Example 1.16. The oxygen scavenging activity was also monitored and is also shown in FIG. 15

Example 4.2

Figure 16:
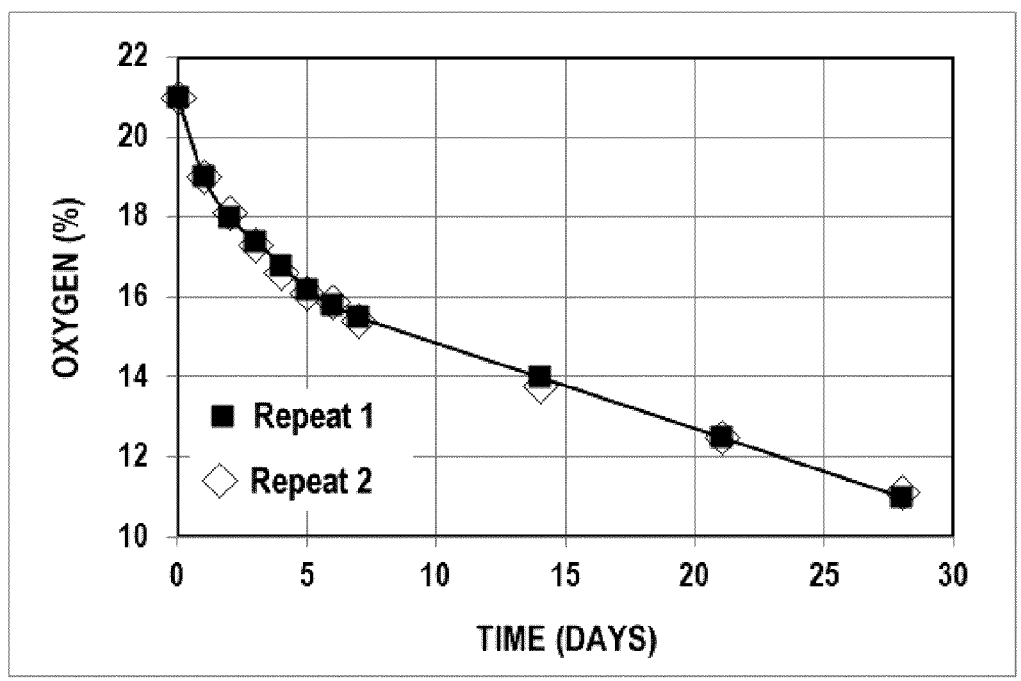
FIG. 16 shows the oxygen consumption of an oxygen scavenging film comprising INDENO 336 of as a function of time.

One hundred parts of PACH-001 was dissolved in a solvent mixture comprising equal amounts of tetrahydrofuran and 2-methoxy propanol to make up a 20% solution. To this solution were added 0.1 parts of cobalt II oleate salt and 0.2 parts of the photoinitiator of Example 1.17. After the solution became clear, it was poured onto a flat Teflon surface and the solvent was allowed to evaporate at room temperature. The obtained polymer film was further dried in a vacuum overnight, which gave an optically clear film having a thickness of around 200 μm. This film was used for the subsequent demonstration for oxygen scavenging activity. Results of the reduction of oxygen versus time are shown in FIG. 16s The results of Examples 4.1 and 4.2 indicate that truxene photoinitiators are very effective in the oxygen scavenging compositions.

The scope of the claims should not be limited by the preferred embodiments set forth in the examples, but should be given the broadest interpretation consistent with the description as a whole.

REFERENCES

The content of the following documents is herein incorporated by reference in their entirety.

Kura et al., "New Oxime Ester Photoinitiators for Color Filter Resists", Radtech Report, May/June 2004, p 30-35;
Odian, "Principles of Polymerization", 4$^{th}$ Edition, Wiley-Interscience;
EP 320,264;
EP 678,534;
EP 855,731;
EP 863,534;
DE 19700064;
JP 05-67405-A;
JP 05-271576-A;
JP 08-171863-A;
JP 09-244230-A;
JP 10-62980-A;
U.S. Pat. No. 3,558,309;
U.S. Pat. No. 4,255,513;
U.S. Pat. No. 4,575,330;
U.S. Pat. No. 4,776,152;
U.S. Pat. No. 5,840,465
U.S. Pat. No. 5,853,446
U.S. Pat. No. 6,051,367;
U.S. Pat. No. 6,949,678;
U.S. Pat. No. 7,449,574;
U.S. Pat. No. 7,556,910;
U.S. Pat. Publication No. 2009/0023085;
U.S. Pat. Publication No. 2010/0210749;

PCT Pat. Publication No. WO 02/100903; and
PCT Pat. Publication No. WO 2006/018405.

The invention claimed is:
1. A compound being:

truxene:

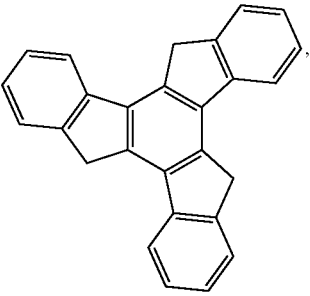

truxenone:

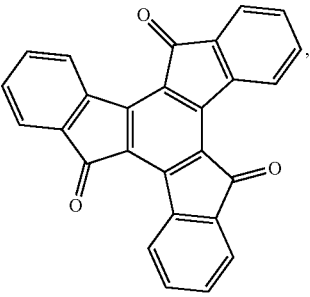

triazatruxene:

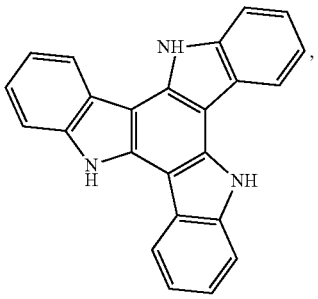

or a derivative thereof,
the truxene, truxenone, triazatruxene, or derivative thereof having attached thereto at least one oxime ester group, either directly -$E_1$ or =$E_2$, or indirectly through a linker -LK-: -LK-$E_1$ or -LK-$(E_1)_2$,
-$E_1$ representing an oxime ester group of formula —$CR_6$=N—O—(C=O)—$R_7$, and
=$E_2$ representing an oxime ester group of formula =N—O—(C=O)—$R_7$,
wherein $R_6$ represents:
hydrogen;
$C_1$-$C_{12}$ alkyl optionally substituted with one or more:
phenyl,
halogen,
—$NR_9R_{10}$,
—O-L, and/or
—S-L;
$C_4$-$C_{10}$ cycloalkyl, $C_2$-$C_{12}$ alkenyl, $C_4$-$C_{10}$ cycloalkenyl, $C_2$-$C_{12}$ alkynyl, or $C_4$-$C_{10}$ cycloalkenyl, each of which being optionally substituted by alkyl and/or —O-L; or phenyl optionally substituted with one or more:
$C_1$-$C_6$ alkyl,
halogen,
nitrile,
alkyloxy,
—$COOR_{10}$, and/or
$C_2$-$C_{12}$ alkylcarboxyl, and
L being hydrogen or $C_1$-$C_6$ alkyl, and
each of $R_9$ and $R_{10}$ is independently hydrogen, $C_1$-$C_{12}$ alkyl; $C_4$-$C_{10}$ cycloalkyl; $C_1$-$C_{12}$ alkenyl; $C_4$-$C_{10}$ cycloalkenyl; $C_2$-$C_{12}$ alkynyl; $C_4$-$C_{10}$ cycloalkynyl; $C_1$-$C_{12}$ haloalkyl; or optionally substituted aryl,
$R_7$ represents alkyl, cycloalkyl, alkenyl, or cycloalkenyl, each of which being optionally substituted with aryl or halogen, or $R_7$ is aryl optionally substituted with alkyl or halogen, and
-LK- is optionally substituted alkylene, cycloalkylene, alkenylene, cycloalkenylene, alkynylene, cycloalkynylene, arylene, —S-arylene, —NH-arylene, or —N(aryl)-arylene, each of which optionally comprising one or more oxygen atom, sulfur atom, nitrogen atom, carbonyl group, carbamate group, carbamide group, and/or ester group.

2. The compound of claim 1, further comprising an acyl group, wherein the acyl group is —C(=O)—$R_{30}$, wherein $R_{30}$ is optionally substituted alkyl, cycloalkyl, alkenyl, cycloalkenyl, alkynyl, cycloalkynyl, or aryl, each of which optionally comprising one or more oxygen atom, sulfur atom, nitrogen atom, carbonyl group, carbamate group, carbamide group, and/or ester group.

3. The compound of claim 2, wherein said alkyl, cycloalkyl, alkenyl, cycloalkenyl, alkynyl, cycloalkynyl, and aryl in $R_{30}$ is substituted with one or more:
polyethylene glycol chain,
$C_1$-$C_{12}$ alkyl optionally substituted with one or more:
—$NR_8R_9$,
—O-L,
—S-L, and/or
phenyl optionally substituted with one or more: $C_1$-$C_6$ alkyl, halogen, nitrile, alkyloxy, $COOR_{10}$, and/or $C_2$-$C_{12}$ alkylcarboxyl;
$C_4$-$C_{10}$ cycloalkyl, $C_2$-$C_{12}$ alkenyl, $C_4$-$C_{10}$ cycloalkenyl, $C_2$-$C_{12}$ alkynyl, $C_4$-$C_{10}$ cycloalkynyl, each of which being optionally substituted by alkyl and/or —O-L, and/or
aryl, such as phenyl, thiophenyl, biphenyl and naphthyl, each of which being optionally substituted with one or more:
$C_1$-$C_6$ alkyl,
halogen,
nitrile,
alkyloxy,
—$COOR_{10}$, and/or
$C_2$-$C_{12}$ alkylcarboxyl,
wherein L is hydrogen or $C_1$-$C_6$ alkyl,
each of $R_9$ and $R_{10}$ is independently hydrogen, $C_1$-$C_{12}$ alkyl; $C_4$-$C_{10}$ cycloalkyl; $C_1$-$C_{12}$ alkenyl; $C_4$-$C_{10}$ cycloalkenyl; $C_2$-$C_{12}$ alkynyl; $C_4$-$C_{10}$ cycloalkynyl; $C_1$-$C_{12}$ haloalkyl; or optionally substituted aryl, and
$R_8$ is independently hydrogen, $C_1$-$C_{12}$ alkyl; $C_4$-$C_{10}$ cycloalkyl; $C_1$-$C_{12}$ alkenyl; $C_4$-$C_{10}$ cycloalkenyl; $C_2$-$C_{12}$ alkynyl; $C_4$-$C_{10}$ cycloalkynyl; $C_1$-$C_{12}$ haloalkyl; or optionally substituted aryl.

4. The compound of claim 2, wherein $R_{30}$ is methyl, 2-methylphenyl, phenyl, thiophenyl, or 4-methoxyphenyl.

5. The compound of claim 1, being of formula:

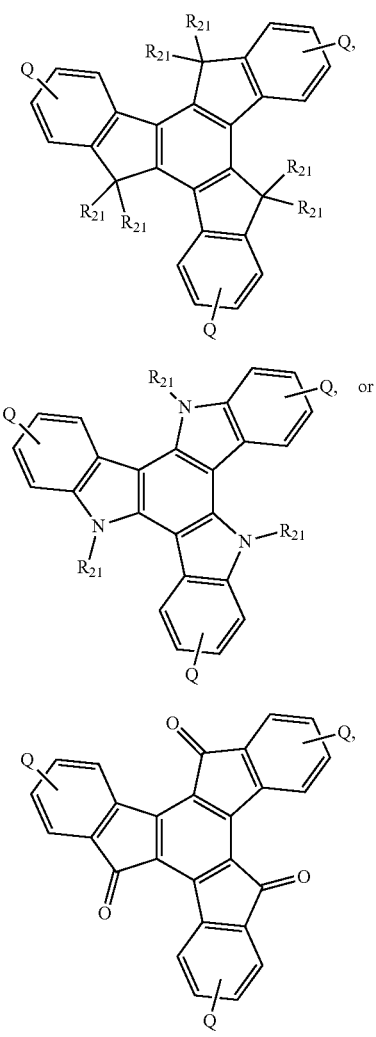

Formula 1

Formula 2

Formula 3 wherein:
each Q independently represents 1 to 4:
  hydrogen;
  -$E_1$;
  -LK-$E_1$;
  -LK-$(E_1)_2$;
  $C_1$-$C_{12}$ alkyl optionally substituted with one or more —$NR_{10}R_{20}$, —O-L and/or —S-L;
  $C_1$-$C_{12}$ haloalkyl;
  $C_4$-$C_8$ cycloalkenyl;
  $C_2$-$C_{12}$ alkynyl;
  phenyl or —N($R_{19}$)-phenyl, each of which being optionally substituted with one or more $C_1$-$C_6$ alkyl, halogen, nitrile, alkyloxy, —$COOR_{19}$, and/or $C_2$-$C_{12}$ alkylcarboxyl;
  benzoyl, naphthoyl, phenyloxycarbonyl, or naphtyloxycarbonyl, each of which being optionally substituted by one or more $C_1$-$C_{20}$ alkyl, $C_1$-$C_4$ haloalkyl, —$SR_{19}$, —$OR_{19}$, —$NR_{19}R_{20}$, halogen, phenyl, —$COOR_{19}$, —$CONR_{19}R_{20}$, —CN, —$NO_2$ and/or $C_3$-$C_{10}$ cycloalkyl, wherein the $C_3$-$C_{10}$ cycloalkyl may be interrupted by —O—, —(C=O)— or —N($R_{19}$)—;
  —$NR_{16}R_{17}$; and/or
  thiophene carbonyl or pyrrolidinyl, each of which being optionally substituted with one or more $C_1$-$C_6$ alkyl, halogen, nitrile, alkyloxy, —$COOR_{19}$, and/or $C_2$-$C_{12}$ alkylcarboxyl, and each $R_{21}$ independently represents:
  hydrogen;
  -$E_1$;
  -LK-$E_1$;
  -LK-$(E_1)_2$;
  $C_1$-$C_{12}$ alkyl optionally substituted with one or more —$NR_{19}R_{20}$, —O-L and/or —S-L;
  $C_4$-$C_8$ cycloalkenyl;
  $C_2$-$C_{12}$ alkynyl; or
  phenyl optionally substituted with one or more $C_1$-$C_6$ alkyl, nitrile, alkyloxy, —$COOR_{16}$, and/or $C_2$-$C_{12}$ alkylcarboxyl, and/or two $R_{21}$ attached to the same carbon atom represent =O or =$E_2$, wherein:
  L represents a hydrogen atom or $C_1$-$C_6$ alkyl,
  $R_{16}$ and $R_{17}$ independently represent:
    hydrogen,
    $C_1$-$C_{12}$ alkyl optionally substituted with one or more —$NR_{19}R_{20}$, —O-L and/or —S-L;
    $C_4$-$C_{10}$ cycloalkyl;
    $C_4$-$C_{10}$ cycloalkenyl;
    $C_2$-$C_{12}$ alkynyl;
    $C_1$-$C_{12}$ haloalkyl; or
    phenyl or benzoyl, each of which optionally substituted with one or more $C_1$-$C_6$ alkyl, halogen, nitrile, alkyloxy, —$COOR_{19}$, and/or $C_2$-$C_{12}$ alkylcarboxyl group, and
  $R_{19}$ and $R_{20}$ independently represent hydrogen, $C_1$-$C_{12}$ alkyl; $C_1$-$C_{12}$ haloalkyl; $C_4$-$C_8$ cycloalkenyl; or $C_2$-$C_{12}$ alkynyl, provided that the compound comprises at least one oxime ester, and provided that when $R_{21}$ is attached to a nitrogen atom and $R_{21}$ is -$E_1$, -$E_1$ is not —$CR_6$=N—O—(C=O)—$R_7$.

6. The compound of claim 5, being of formula:

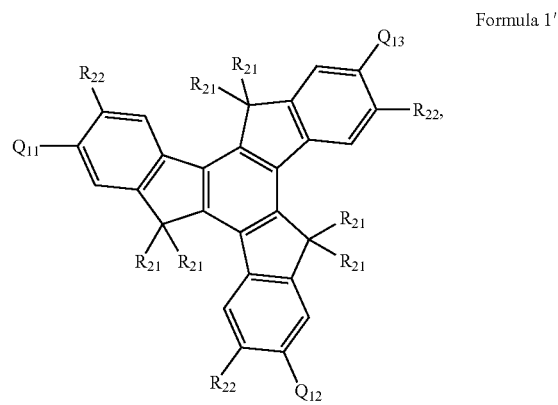

Formula 1'

-continued

Formula 2'

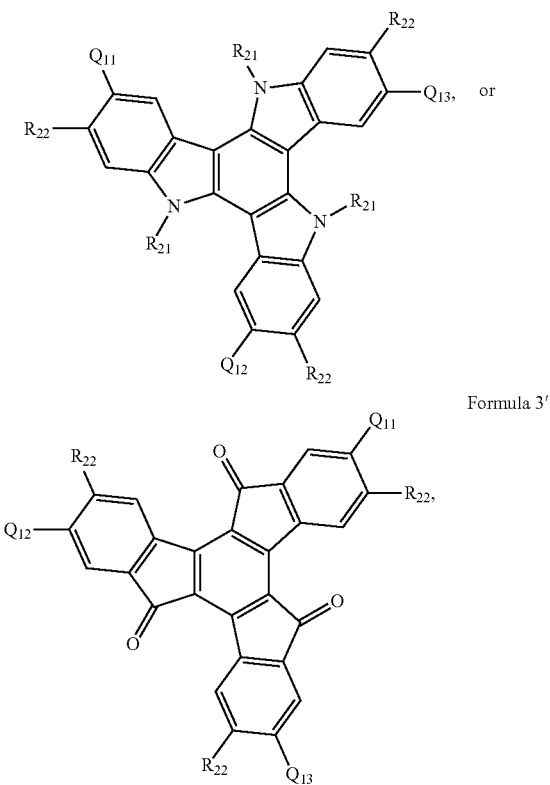

Formula 3' wherein:
each of $Q_{11}$, $Q_{12}$ and $Q_{13}$ independently represent:
hydrogen;
-$E_1$;
-LK-$E_1$;
-LK-$(E_1)_2$;
$C_1$-$C_{12}$ alkyl optionally substituted with one or more —$NR_{19}R_{20}$, —O-L and/or —S-L;
$C_1$-$C_{12}$ haloalkyl;
$C_4$-$C_8$ cycloalkenyl;
$C_2$-$C_{12}$ alkynyl;
phenyl or —N($R_{19}$)-phenyl, each of which being optionally substituted with one or more $C_1$-$C_6$ alkyl, halogen, nitrile, alkyloxy, —COOR$_{19}$, and/or $C_2$-$C_{12}$ alkylcarboxyl;
benzoyl, naphthoyl, phenyloxycarbonyl, or naphtyloxycarbonyl, each of which being optionally substituted by one or more $C_1$-$C_{20}$ alkyl, $C_1$-$C_4$ haloalkyl, —SR$_{19}$, —OR$_{19}$, —NR$_{19}R_{20}$, halogen, phenyl, —COOR$_{19}$, —CONR$_{19}R_{20}$, —CN, —NO$_2$ and/or $C_3$-$C_{10}$ cycloalkyl, wherein the $C_3$-$C_{10}$ cycloalkyl may be interrupted by —O—, —(C=O)— or —N($R_{19}$)—;
—NR$_{16}R_{17}$; or
thiophene carbonyl or pyrrolidinyl, each of which being optionally substituted with one or more $C_1$-$C_6$ alkyl, halogen, nitrile, alkyloxy, —COOR$_{19}$, and/or $C_2$-$C_{12}$ alkylcarboxyl,
each $R_{22}$ independently represents:
hydrogen;
$C_1$-$C_{12}$ alkyl optionally substituted with one or more —NR$_{19}R_{20}$, —O-L and/or —S-L;
$C_1$-$C_{12}$ haloalkyl;
$C_4$-$C_8$ cycloalkenyl;
$C_2$-$C_{12}$ alkynyl;
phenyl or —N($R_{19}$)-phenyl, each of which being optionally substituted with one or more $C_1$-$C_6$ alkyl, halogen, nitrile, alkyloxy, —COOR$_{19}$, and/or $C_2$-$C_{12}$ alkylcarboxyl; or
benzoyl, naphthoyl, phenyloxycarbonyl, or naphtyloxycarbonyl, each of which being optionally substituted by one or more $C_1$-$C_{20}$ alkyl, $C_1$-$C_4$ haloalkyl, —SR$_{19}$, —OR$_{19}$, —NR$_{19}R_{20}$, halogen, phenyl, —COOR$_9$, —CONR$_{19}R_{20}$, —CN, —NO$_2$ and/or $C_3$-$C_{10}$ cycloalkyl, wherein the $C_3$-$C_{10}$ cycloalkyl is interrupted by —O—, —(C=O)— or —N($R_{19}$)—,
wherein $R_{16}$, $R_{17}$, $R_{19}$, $R_{20}$, $R_{21}$, and L are as defined in claim 5,
provided that the compound comprises at least one oxime ester, and
provided that when $R_{21}$ is attached to a nitrogen atom and $R_{21}$ is not -$E_1$.

7. The compound of claim 6, wherein $R_6$ is alkyl optionally substituted with —O—$C_{1-6}$ alkyl.

8. The compound of claim 7, wherein $R_6$ is methyl.

9. The compound of claim 6, $R_7$ represents $C_1$-$C_{12}$ alkyl optionally substituted with phenyl; $C_4$-$C_{10}$ cycloalkyl; or phenyl optionally substituted with $C_1$-$C_6$ alkyl.

10. The compound of claim 9, wherein $R_7$ is methyl.

11. The compound of claim 6, wherein the alkylene, cycloalkylene, alkenylene, cycloalkenylene, alkynylene, cycloalkynylene, arylene, —S-arylene, —NH-arylene, and —N(aryl)-arylene of LK are substituted with one or more:
polyethylene glycol chain,
$C_1$-$C_{12}$ alkyl optionally substituted with one or more:
—NR$_8R_9$,
—O-L,
—S-L, and/or
phenyl optionally substituted with one or more: $C_1$-$C_6$ alkyl, halogen, nitrile, alkyloxy, COOR$_{10}$, and/or $C_2$-$C_{12}$ alkylcarboxyl;
$C_4$-$C_{10}$ cycloalkyl, $C_2$-$C_{12}$ alkenyl, $C_4$-$C_{10}$ cycloalkenyl, $C_2$-$C_{12}$ alkynyl, $C_4$-$C_{10}$ cycloalkynyl, each of which being optionally substituted by alkyl and/or —O-L, and/or
aryl, such as phenyl, biphenyl and naphthyl, or aryloyl, such as benzoyl, each of which being optionally substituted with one or more:
$C_1$-$C_6$ alkyl,
halogen,
nitrile,
alkyloxy,
—COOR$_{10}$, and/or
$C_2$-$C_{12}$ alkylcarboxyl,
wherein L is hydrogen or $C_1$-$C_6$ alkyl,
each of $R_9$ and $R_{10}$ is independently hydrogen, $C_1$-$C_{12}$ alkyl; $C_4$-$C_{10}$ cycloalkyl; $C_1$-$C_{12}$ alkenyl; $C_4$-$C_{10}$ cycloalkenyl; $C_2$-$C_{12}$ alkynyl; $C_4$-$C_{10}$ cycloalkynyl; $C_1$-$C_{12}$ haloalkyl; or optionally substituted aryl, and
$R_8$ is independently hydrogen, $C_1$-$C_{12}$ alkyl; $C_4$-$C_{10}$ cycloalkyl; $C_1$-$C_{12}$ alkenyl; $C_4$-$C_{10}$ cycloalkenyl; $C_2$-$C_{12}$ alkynyl; $C_4$-$C_{10}$ cycloalkynyl; $C_1$-$C_{12}$ haloalkyl; or optionally substituted aryl.

12. The compound of claim 6, wherein -LK-$E_1$ represents:

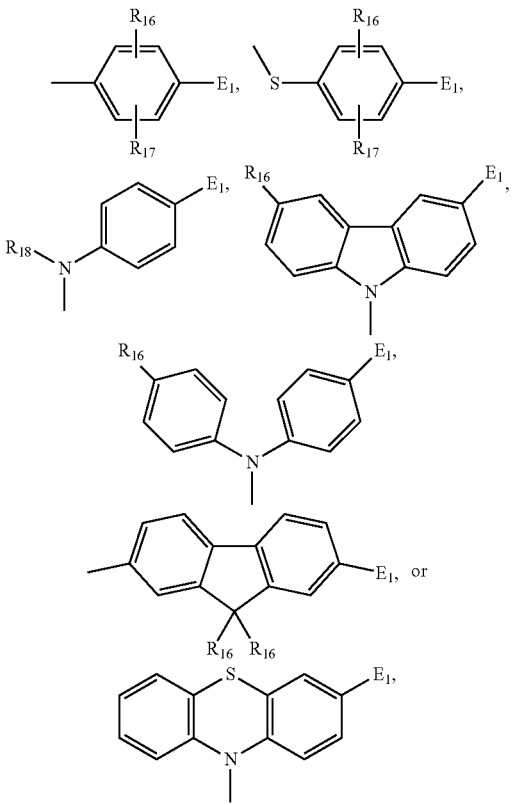

and

-LK-$(E_1)_2$ represents:

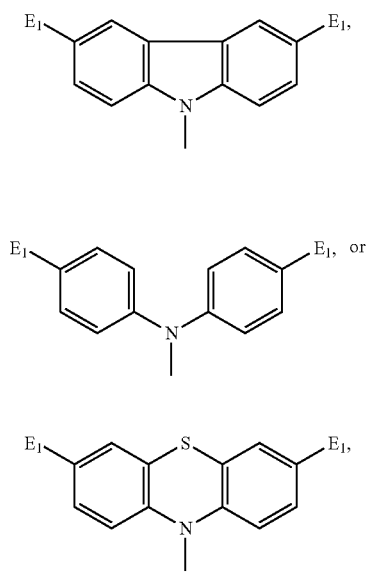

wherein $R_{18}$ is hydrogen or $C_1$-$C_{12}$ alkyl optionally substituted with one or more —O-L and/or —S-L, and wherein L is hydrogen or $C_1$-$C_6$ alkyl, wherein $R_{16}$ and $R_{17}$ independently represent:
- hydrogen,
- $C_1$-$C_{12}$ alkyl optionally substituted with one or more —$NR_{19}R_{20}$, —O-L and/or —S-L;
- $C_4$-$C_{10}$ cycloalkyl;
- $C_4$-$C_{10}$ cycloalkenyl;
- $C_2$-$C_{12}$ alkynyl;
- $C_1$-$C_{12}$ haloalkyl; or
- phenyl or benzoyl, each of which optionally substituted with one or more $C_1$-$C_6$ alkyl, halogen, nitrile, alkyloxy, —$COOR_{19}$, and/or $C_2$-$C_{12}$ alkylcarboxyl group.

13. The compound of claim 6, wherein each $Q_{11}$, $Q_{12}$, and $Q_{13}$, when present, represents one -$E_1$ of formula —$CR_6$=N—O—(C=O)—$R_7$, wherein $R_6$ represents $C_1$-$C_{12}$ alkyl optionally substituted with —O-L, wherein L is $C_1$-$C_6$ alkyl, and $R_7$ represents $C_1$-$C_{12}$ alkyl;

all $R_{22}$, when present, represent hydrogen; and all $R_{21}$, when present, represent hydrogen or $C_1$-$C_{12}$ alkyl.

14. The compound of claim 6, wherein:

each $Q_{11}$, $Q_{12}$, and $Q_{13}$, when present, represents one -LK-$E_1$, wherein $E_1$ is of formula —$CR_6$=N—O—(C=O)—$R_7$, wherein $R_6$ represents $C_1$-$C_{12}$ alkyl optionally substituted with —O-L, wherein L is $C_1$-$C_6$ alkyl, and $R_7$ represents $C_1$-$C_{12}$ alkyl;

all $R_{22}$, when present, represent hydrogen;

all $R_{21}$, when present, represents hydrogen or $C_1$-$C_{12}$ alkyl; and

LK represents

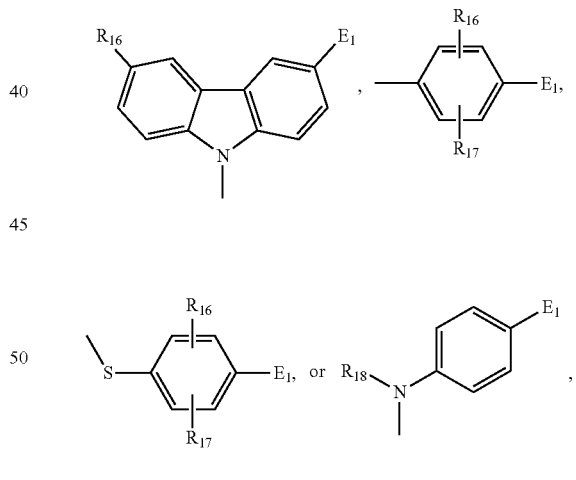

wherein $R_{16}$ is hydrogen or benzoyl substituted with $C_1$-$C_6$ alkyl, $R_{17}$ represents hydrogen and $R_{18}$ represents $C_1$-$C_{12}$ alkyl.

15. The compound of claim 6, wherein each of $Q_{11}$, $Q_{12}$, and $Q_{13}$, when present, represents hydrogen, each $R_{22}$, when present, represents one —$N(R_{19})$-phenyl wherein $R_{19}$ represents $C_1$-$C_{12}$ alkyl, and every pair of $R_{21}$ attached to a common carbon atom represent =$E_2$ wherein $R_7$ represents $C_1$-$C_{12}$ alkyl.

16. The compound of claim 1, being of formula:
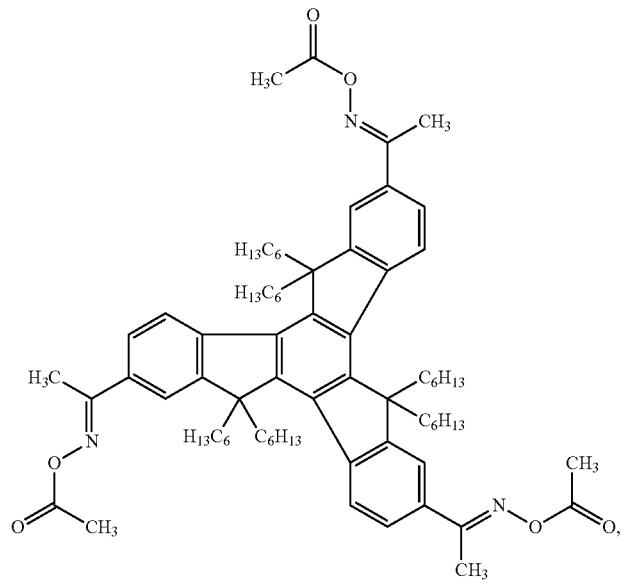
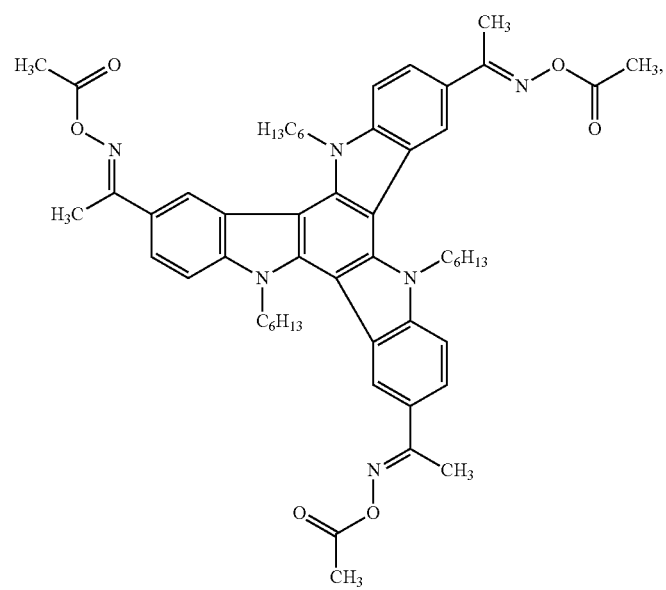

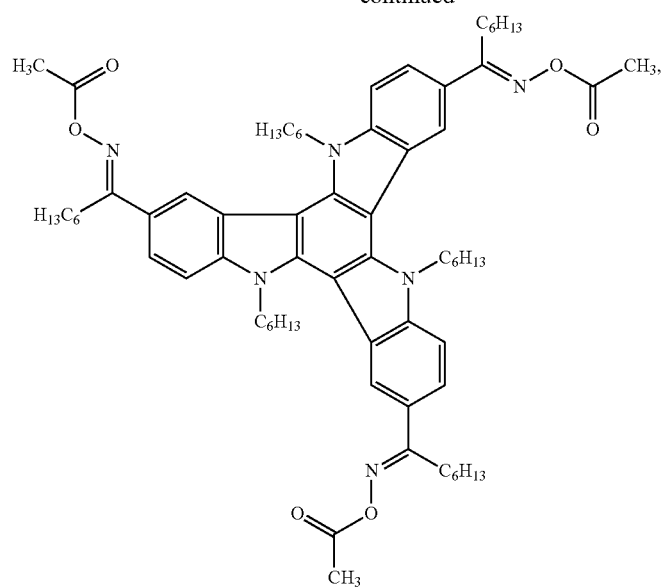
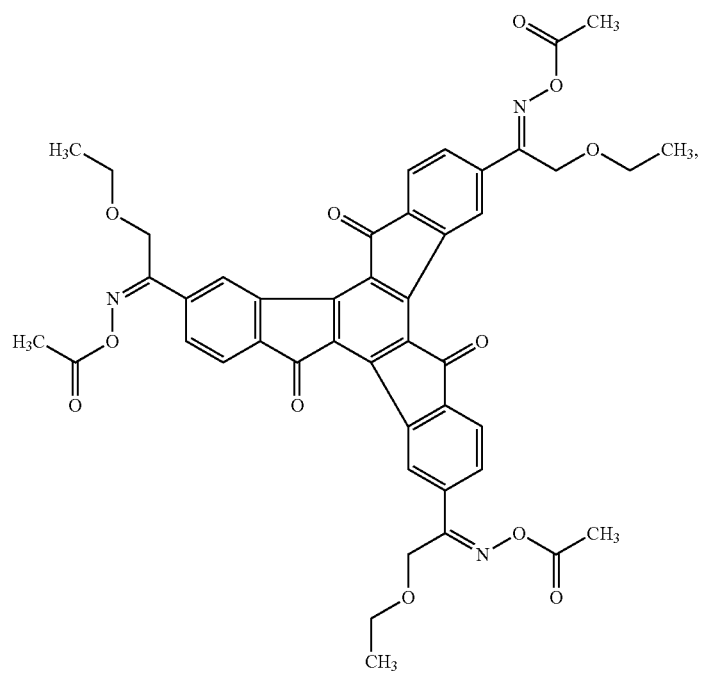

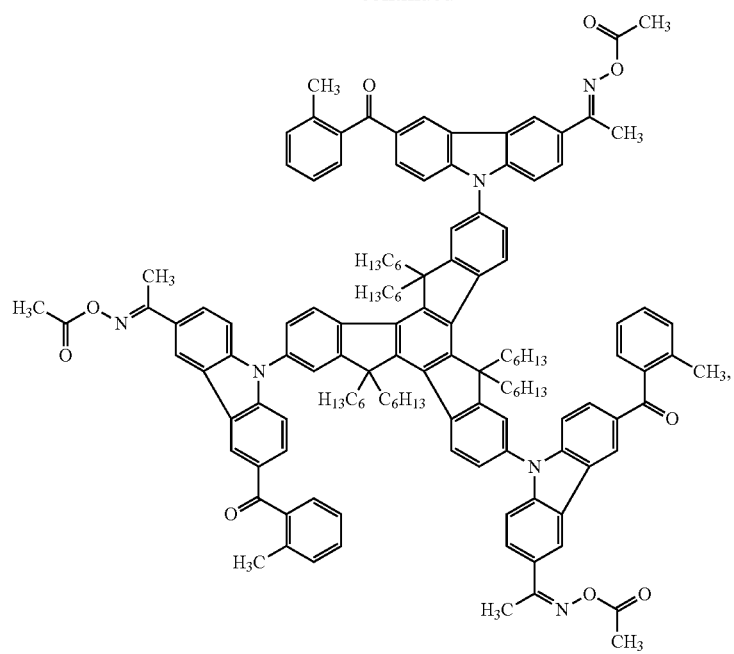
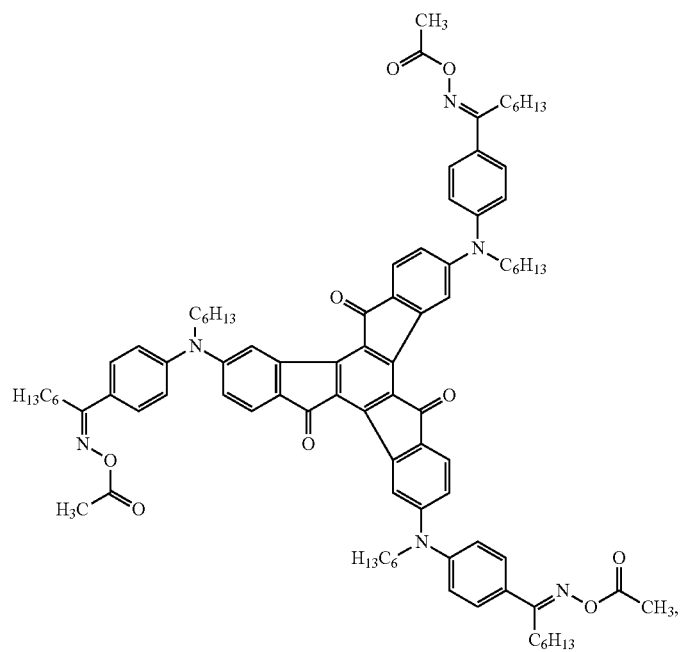

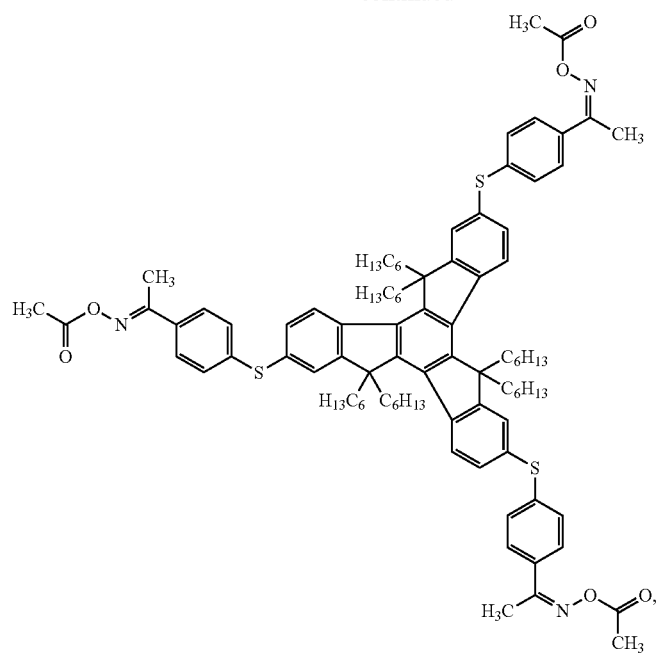
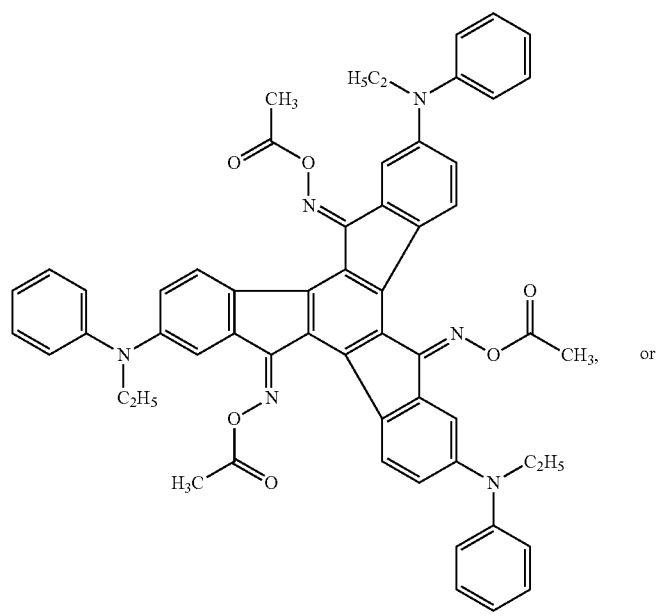
or

-continued
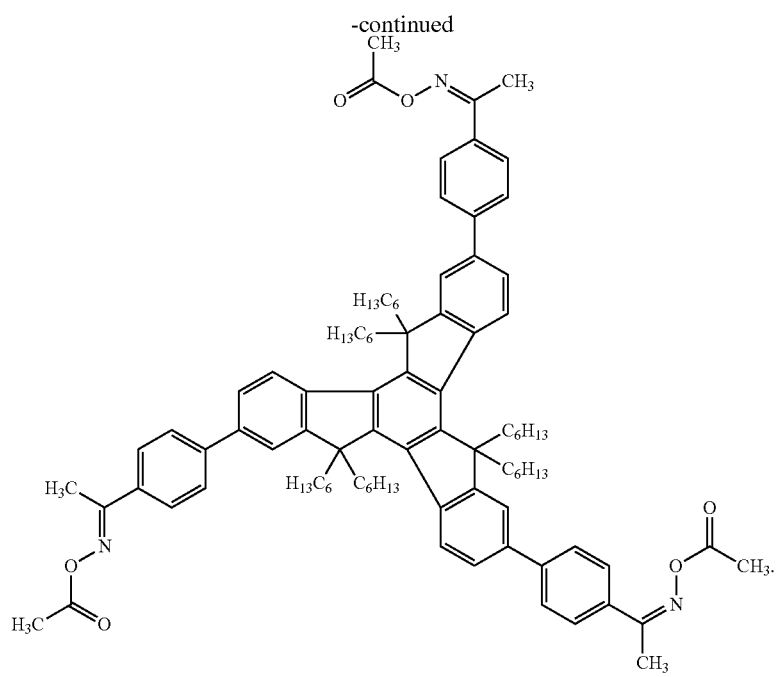
* * * * *